United States Patent
Powell et al.

(10) Patent No.: US 9,585,957 B2
(45) Date of Patent: Mar. 7, 2017

(54) ADENOSINE RECEPTOR AGONISTS AND ANTAGONISTS TO MODULATE T CELL RESPONSES

(75) Inventors: Jonathan D Powell, Baltimore, MD (US); Charles George Drake, Baltimore, MD (US); Paul Zarek, McLean, VA (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 750 days.

(21) Appl. No.: 12/676,741

(22) PCT Filed: Sep. 8, 2008

(86) PCT No.: PCT/US2008/075610
§ 371 (c)(1),
(2), (4) Date: Oct. 6, 2010

(87) PCT Pub. No.: WO2009/033161
PCT Pub. Date: Mar. 12, 2009

(65) Prior Publication Data
US 2011/0027295 A1  Feb. 3, 2011

Related U.S. Application Data

(60) Provisional application No. 60/970,841, filed on Sep. 7, 2007, provisional application No. 60/970,848, filed on Sep. 7, 2007.

(51) Int. Cl.
| | | |
|---|---|---|
| *A61K 39/00* | (2006.01) | |
| *A61P 37/00* | (2006.01) | |
| *A61P 35/00* | (2006.01) | |
| *A61K 45/06* | (2006.01) | |
| *A61K 39/395* | (2006.01) | |

(52) U.S. Cl.
CPC ........ *A61K 45/06* (2013.01); *A61K 39/39558* (2013.01)

(58) Field of Classification Search
None
See application file for complete search history.

(56) References Cited

U.S. PATENT DOCUMENTS 6,326,390 B1 † 12/2001 Leung
7,217,702 B2    5/2007 Beauglehole et al.
2002/0115635 A1 † 8/2002 Fishman
2004/0247713 A1 † 12/2004 Seiberg
2005/0220799 A1 † 10/2005 Sitkovsky

FOREIGN PATENT DOCUMENTS

CH          423800       † 5/1967

OTHER PUBLICATIONS

Ohta et al., A2A adenosine receptor protects tumors from antitumor T cells, PNAS, Aug. 29, 2006, pp. 13132-13137, vol. 103, No. 35.
Shin et al., In vivo costimulatory role of B7-DC in tuning T helper cell 1 and cytotoxic T lymphocyte responses, J. Exp. Med., May 16, 2005, pp. 1531-1541, vol. 201, No. 10.

† cited by third party

*Primary Examiner* — Sean McGarry
(74) *Attorney, Agent, or Firm* — Johns Hopkins Technology Transfer

(57) ABSTRACT

Described are uses of A2a adenosine receptor antagonists and agonists to provide long term modulation of immune responses. A2a receptor antagonists in particular are provided to enhance immune responses by reducing T-cell mediated tolerance to antigenic stimuli and agonists are provided to enhance effectiveness of immunosuppressive agents. The application provides methods of treatment and prevention based on the long term effects of the compounds on T cell responses.

5 Claims, 17 Drawing Sheets

A.

B.

ADENOSINE RECEPTOR AGONISTS AND ANTAGONISTS TO MODULATE T CELL RESPONSES

CROSS-REFERENCE TO RELATED APPLICATIONS

This application is the U.S. National Phase Application, pursuant to 35 U.S.C. §371, of PCT International Application Serial No. PCT/US2008/075610, filed Sep. 8, 2008, designating the United States and published in English published on Mar. 12, 2009, as publication WO 2009/033161, which claims priority to U.S. Provisional Application No. 60/970,841, entitled "Adenosine Receptor Antagonists To Enhance T Cell Responses" and 60/970,848, entitled "Adenosine Receptor Agonists To Enhance T Cell Tolerance," both filed Sep. 7, 2007, the disclosures of which are hereby incorporated by reference in their entirety.

GOVERNMENT SUPPORT

This invention was made with U.S. government support under grants RO1CA098109, P50CA098252 and P30CA06973 awarded by the NIH. The Government has certain rights in the invention.

FIELD OF THE INVENTION

This application relates to uses of $A_{2a}$ adenosine receptor agonists and antagonists to modulate T-cell mediated tolerance to antigenic stimuli. In particular, $A_{2a}$ receptor antagonists provide long term enhancement of immune responses by reducing T-cell mediated tolerance to antigenic stimuli, enhancing the induction of memory T cells and enhancing the efficacy of passive antibody administration for the treatment of cancer and infectious diseases while $A_{2a}$ receptor agonists provide long term reduction of immune responses by enhancing T-cell mediated tolerance to antigenic stimuli, in particular to reduce use of immunosuppressive agents in certain conditions. The application provides methods of treatment and prevention of inflammatory responses based on the long term effects of the compounds on T cell responses.

INCORPORATION-BY-REFERENCE OF MATERIAL SUBMITTED ELECTRONICALLY

This application contains a sequence listing. It has been submitted electronically via EFS-Web as an ASCII text file entitled "P04897-05_ST25.txt." The sequence listing is 1,508 bytes in size, and was created on Jun. 16, 2015. It is hereby incorporated by reference in its entirety.

BACKGROUND

Immune modulation is a critical aspect of the treatment of a number of diseases and disorders. T cells in particular play a vital role in fighting infections and have the capability to recognize and destroy cancer cells. Enhancing T cell mediated responses is a key component to enhancing responses to therapeutic agents. However, it is critical in immune modulation that any enhancement of an immune response is balanced against the need to prevent autoimmunity as well as chronic inflammation. Chronic inflammation and self-recognition by T cells is a major cause for the pathogenesis of systemic disorders such as rheumatoid arthritis, multiple sclerosis and systemic lupus erythematosus. Furthermore, long term immunosuppression is required in preventing rejection of transplanted organs or grafts.

The mechanisms that prevent T-cell mediated autoimmune reactions are collectively known as T cell "tolerance". Tolerance can occur by removing antigen specific T cells from the population, which occurs both in the thymus and the periphery. In addition, tolerance can be maintained by 'turning off' certain antigen specific T cells or rendering them anergic. When T cells recognize an antigen under conditions that promote anergy, these same cells later fail to respond to antigen upon rechallenge even under normally activating conditions. Anergy is induced when T cell receptor engagement (Signal 1) occurs in the absence of co-stimulation (Signal 2). A major set of co-regulatory molecules is in the B7-CD28 family.

In addition to anergy and deletion, recently it has become clear that regulatory T cells play an important role in maintaining tolerance. Regulatory T cells suppress autoreactive T cells. Thus, as the level of regulatory T cells decreases, the potential for autoimmunity rises. Interestingly, tumors have been shown to evade immune destruction by impeding T cell activation through inhibition of co-stimulatory factors in the B7-CD28 and TNF families, as well as by attracting regulatory T cells, which inhibit anti-tumor T cell responses (see Wang (2006) Immune Suppression by Tumor Specific CD4+ Regulatory T cells in Cancer. Semin. Cancer. Biol. 16:73-79; Greenwald, et al. (2005) The B7 Family Revisited. Ann. Rev. Immunol. 23:515-48; Watts (2005) TNF/TNFR Family Members in Co-stimulation of T Cell Responses Ann. Rev. Immunol. 23:23-68; Sadum, et al. (2007) Immune Signatures of Murine and Human Cancers Reveal Unique Mechanisms of Tumor Escape and New Targets for Cancer Immunotherapy. Clin. Canc. Res. 13(13): 4016-4025).

Autoimmune diseases develop when the body's immune system fails to recognize normal body tissues and attacks and destroys them as if they were foreign rather than attacking an outside organism. There are nearly 150 autoimmune disorders with no currently known cures. Although the cause is not fully understood, pioneering work by Rose, Witebsky, Roitt and Doniach provided evidence that autoimmune diseases result at least in part from loss of T cell tolerance. An essential prerequisite for the pathogenesis of autoimmune diseases is indeed the breakage of immunological tolerance, which leads to the immune system mounting an effective and specific immune response against self determinants. Several theories exist as to what causes this breakdown, including the breakdown of "clonal deletion theory", according to which self-reactive lymphoid cells are destroyed during the development of the immune system in an individual, the breakdown of "clonal anergy theory", in which self-reactive T- or B-cells become inactivated in the normal individual and cannot amplify the immune response, the breakdown of "idiotype network theory", wherein a network of antibodies capable of neutralizing self-reactive antibodies exists naturally within the body, and the "suppressor population theory", wherein regulatory T-lymphocytes prevent or limit autoaggressive immune responses.

Adenosine modulates diverse physiological functions including induction of sedation, vasodilatation, suppression of cardiac rate and contractility, inhibition of platelet aggregation, stimulation of gluconeogenesis and inhibition of lipolysis (see, Stiles (1986) Trends Pharmacol. Sci. 7:486; Williams, (1987) Ann. Rev. Pharmacol. Toxicol. 27:315; Rarnkumar et al., (1988) Prog. Drug. Res. 32:195). In addition, adenosine and some adenosine analogs that non-selectively activate adenosine receptor subtypes decrease neutrophil production of inflammatory oxidative products (Cronstein et al., (1986) *Ann. N.Y. Acad. Sci.* 451:291; Roberts et al., (1985) *Biochem. J.,* 227:669; Schrier et al., (1986) *J. Immunol.* 137:3284; Cronstein et al., (1987) *Clinical lmmunol. Immunopath.* 42:76).

Adenosine binds to P1 purinergic receptors, which are members of the G protein-coupled receptor family. Four subtypes of adenosine receptors have been cloned: $A_1$, $A_{2a}$, $A_{2B}$, and $A_3$. The four subtypes have the hallmark structural characteristics that are common to G protein-coupled receptors, including seven putative transmembrane spanning domains, an extracellular $NH_2$ terminus, cytoplasmic COOH terminus, and a third intracellular loop that is important in binding G proteins.

The $A_{2a}$ receptor cDNA, which has been cloned from several species including humans, encodes a protein of 45 kDa, larger than the molecular masses of the other subtypes. This is primarily due to the additional 80-90 amino acids of the COOH-terminal tail. The overall amino acid identity is 90% among species, with most of the differences occurring in the second extracellular loop and the long COOH-terminal domain. The COOH-terminal domain has several serine and threonine residues that are potential phosphorylation sites. $A_{2a}$ adenosine receptors stimulate adenylyl cyclase and increase the production of cAMP by coupling to stimulatory G proteins ($G_s$) or to $G_{olf}$ in certain tissues. In addition to the cAMP-protein kinase A (PKA) pathway, recent studies indicate that serine/threonine protein phosphatase, mitogen-activated protein kinase (MAP kinase), PKC, and phospholipase D may participate in mediating the effects of $A_{2a}$ adenosine receptor activation. Further, the Epac family of cAMP-regulated guanine nucleotide exchange factors (cAMP-GEFs, also known as Epac1 and Epac2) may also participate in mediating the effects of these receptors.

Studies have indicated that adenosine has a direct effect on hematopoietic and endothelial cells to reduce inflammation (for a review, see Linden (2001) Molecular approach to adenosine receptors: receptor mediated mechanisms of tissue protection. *Annu Rev Pharmacol Toxicol* 41: 775-787). Evidence for an anti-inflammatory role of $A_{2a}$ adenosine receptor activation comes from a variety of studies both in vivo and in vitro (Cronstein et al. (1990) The adenosine/neutrophil paradox resolved: human neutrophils possess both A1 and A2 receptors that promote chemotaxis and inhibit O2⁻ generation, respectively. *J Clin Invest* 85: 1150-1157; Schrier and Imre (1986) The effects of adenosine agonists on human neutrophil function (Abstract). *J Immunol* 137: 3284; Sullivan et al. (1995) The specific type IV phosphodiesterase inhibitor rolipram combined with adenosine reduces tumor necrosis factor-a (TNF-a)-primed neutrophil oxidative activity. *Int J Immunopharmacol* 17: 793-803). This physiological role of endogenous adenosine became apparent after the demonstration that activated neutrophils or endothelial cells release and respond to adenosine. Monocytes accumulate more slowly at sites of inflammation than neutrophils and contribute to the inflammatory process by producing and releasing cytokines. The results of several studies indicate that the proinflammatory cytokine TNF-α, is regulated by $A_{2a}$ adenosine receptors (Bouma et al. (1994) Differential regulatory effects of adenosine on cytokine release by activated human monocytes. *J Immunol* 153:4159-4168; Eigler et al. (1997) Endogenous adenosine curtails lipopolysaccharide-stimulated tumour necrosis factor synthesis. *Scand J Immunol* 45: 132-139; Hasko et al. (1996) Adenosine receptor agonists differentially regulate IL-10, TNF-a, and nitric oxide production in RAW 264.7 macrophages and in endotoxemic mice. *J Immunol* 96: 4634-4640; Reinstein et al. (1994) Suppression of lipopolysaccharidestimulated release of tumor necrosis factor by adenosine: evidence for $A_2$ receptors on rat Kupffer cells. *Hepatology* 19: 1445-1452).

On the basis of the evidence that activation of $A_{2a}$ adenosine receptors regulates factors that attenuate inflammation, studies have been performed using selective $A_{2a}$ agonists in tissue to determine whether activation of $A_{2a}$ receptors confers tissue protection. In many of these studies, the observation that $A_{2a}$ agonist-induced tissue protection was associated with a reduction of factors associated with inflammation suggested that $A_{2a}$ agonists contribute to tissue protection by attenuating inflammation, although a direct causal relationship between tissue protection and attenuation of inflammation by $A_{2a}$ agonists has not been proven.

Evidence has accumulated that adenosine accumulation in hypoxic conditions can lead to activation of $A_{2a}$ receptors and, in certain instances, can cause inhibition of immune cells, in particular, of T lymphocytes.

Ohta and Sitkovsky have proposed that adenosine, when acting on $A_{2a}$ receptors, protects tissues from excessive inflammation (Ohta, and Sitkovsky (2001) Role of G-protein-coupled adenosine receptors in down-regulation of inflammation and protection from tissue damage. *Nature* 414(6866):916-20). Using an $A_{2a}$ receptor knock-out mouse, Ohta et al. showed that, while sub-threshold doses of an inflammatory stimulus caused minimal tissue damage in wild-type mice, such doses were sufficient to induce extensive tissue damage, more prolonged and higher levels of pro-inflammatory cytokines, and death of animals deficient in the $A_{2a}$ adenosine receptor. Additional observations were made in studies of model systems of inflammation and liver damage as well as during bacterial endotoxin-induced septic shock.

Kinsel and Sitkovsky overviewed possible targeting of certain G protein coupled receptors, including $A_{2a}$ receptors, in manipulating inflammation in vivo with ligands (Kinsel J F, Sitkovsky M V. (2003) Possible targeting of G protein coupled receptors to manipulate inflammation in vivo using synthetic and natural ligands. *Ann Rheum Dis.* 62 Suppl 2:ii22-4). The authors state that targeting of these receptors by selective agonists may lead to better protocols of anti-inflammatory treatments, and that inhibiting the Gs protein coupled mediated signaling with antagonists could be explored in studies of approaches to enhance inflammation and tissue damage.

Ohta, et al. have also proposed that the $A_{2a}$ adenosine receptor protects tumors from anti-tumor T cells (Ohta, et al. (2006) $A_{2a}$ adenosine receptor protects tumors from antitumor T cells. *PNAS* 103(35):13132-7). Again using $A_{2a}$ receptor deficient mice, the investigators showed that approximately 60% of tumor cells were rejected when compared to no rejection in normal mice. The investigators also showed that treatment using an $A_{2a}$ receptor antagonist improved inhibition of tumor growth, destruction of metastases and prevention of neovascularization by anti-tumor T cells. In all cases, the treatment was continuous during the timeframe, with no suggestion of long term effects.

PCT Publication No. WO 03/050241 by Sitkovsky and Ohta describes the methods to increase an immune response to an antigen, increasing vaccine efficacy or increasing an immune response to a tumor antigen or immune cell-mediated tumor destruction by administering an agent that inhibits extracellular adenosine or inhibits adenosine receptors.

Sullivan described the role of endogenous adenosine in blocking potentially destructive inflammatory cascades by binding to $A_{2a}$ adenosine receptors and decreasing activation of platelets, leukocytes and endothelial cells (Sullivan G W. (2003) Adenosine $A_{2a}$ receptor agonists as anti-inflammatory agents. *Curr Opin Investig Drugs.* 4(11):1313-9). Sullivan also reviews potential disease targets for $A_{2a}$ receptor agonist treatment, including in allergen-induced inflammation, ischemia-reperfusion injury, sepsis and autoimmune diseases.

Kinsel and Sitkovsky overviewed possible targeting of certain G protein coupled receptors, including $A_{2a}$ receptors, in manipulating inflammation in vivo with ligands (Kinsel J F, Sitkovsky M V. (2003) Possible targeting of G protein coupled receptors to manipulate inflammation in vivo using synthetic and natural ligands. *Ann Rheum Dis.* 62 Suppl 2:ii22-4). The authors state that targeting of these receptors by selective agonists may lead to better protocols of anti-inflammatory treatments.

Ulusal et al. conducted in vivo experimental studies to investigate whether $A_{2a}$ receptor agonists reduce allostimulatory functions of dendritic cells, for example through modulation of surface expression of the costimulatory molecules and down-regulation of cytokines (Ulusal B G, et al. (2006) The effect of $A_{2a}$ adenosine receptor agonist on composite tissue allotransplant survival: an in vivo preliminary study. *J Surg Res.* 131(2):261-6). The authors state that the results from this study showed that $A_{2a}$ adenosine receptor agonist treatment does not prolong composite tissue allograft survival.

Sevigny, et al. investigated the in vitro and in vivo effect of $A_{2a}$ receptor agonists to attenuate allogenic immune activation (Sevigny C P, et al. (2007 Apr. 1) Activation of adenosine$_{2a}$ receptors attenuates allograft rejection and alloantigen recognition. *J Immunol* 178(7):4240-9). The authors state that the results indicated that $A_{2a}$ receptor agonists attenuate allogenic recognition by action on both T lymphocytes and APCs in vitro and delayed acute rejection in vivo and may represent a new class of compounds for induction therapy in organ transplantation.

Nemeth, et al. investigated adenosine receptor activation in type I diabetes and suggest that adenosine receptor ligands could be potential candidates for treatment of type I diabetes and could be promising targets in autoimmune disease (Németh Z H, et al. (2007) Adenosine receptor activation ameliorates type 1 diabetes. FASEB J. epub).

There remains a need for therapies that provide long term enhancement of immune responses to specific antigens, particularly for treatment and prevention of abnormal cell proliferation and for treatment of infectious diseases and disorders. There also remains a need for treatments that provide long term, targeted immune suppression and reduce the need for standard immunosuppressive therapies in certain disorders, in particular in the area of transplantation and autoimmunity.

It is an object of the present invention to provide methods of treatment that allow simplified treatment protocols and enhance immune responses against certain antigens. It is a specific object of the invention to provide improved methods of preventing or treating abnormal cell proliferation and infectious diseases in a host. It is a separate object of the present invention to provide more effective therapeutic regimes to reduce the need for long term treatment with immunosuppressive therapies in a host.

SUMMARY

It has been discovered that $A_{2a}$ receptors are responsible for induction of long term T cell tolerance. These receptors can induce tolerance both by promoting T cell anergy, under which T cells fail to respond to an antigen upon re-challenge even under normally activating conditions, and by inducing regulatory T cells, which are responsible for maintained tolerance.

It has now been found that $A_{2a}$ receptor antagonists can overcome T cell tolerance and thus stimulate long term resistance to certain antigens. In particular, it has been found that $A_{2a}$ receptor antagonists can overcome tumor escape mechanisms including both anergy and regulatory T cell induction caused by tumor cells and cause long-term tumor susceptibility to treatment. Thus, provided are methods of enhancing immune responses against infectious agents as well as methods of treatment or prevention of abnormal cell proliferation.

In one principal embodiment, methods are provided for enhancing an immune response in a host in need thereof. The immune response can be enhanced by reducing T cell tolerance, including by increasing IFN-γ release, by decreasing regulatory T cell production or activation, or by increasing antigen-specific memory T cell production in a host. In one embodiment, the method comprises administering a $A_{2a}$ receptor antagonist to a host in combination or alternation with an antibody. In particular subembodiments, the antibody is a therapeutic antibody. In one particular embodiment, a method of enhancing efficacy of passive antibody therapy is provided comprising administering an $A_{2a}$ receptor antagonist in combination or alternation with one or more passive antibodies. This method can enhance the efficacy of antibody therapy for treatment of abnormal cell proliferative disorders such as cancer, or can enhance the efficacy of therapy in the treatment or prevention of infectious diseases. The antagonist can be administered in combination or alternation with antibodies such as rituximab, herceptin or erbitux, for example. In a separate embodiment, the method comprises administering a first $A_{2a}$ receptor antagonist substantially in combination with an antigen to a host and subsequently administering a second $A_{2a}$ receptor antagonist in the absence of the antigen. The antigens are typically derived from a pathogenic organism, such as a virus or bacterium. The first and second $A_{2a}$ receptor antagonists can be the same or can be different and can be administered in the same or in separate preparations. The first $A_{2a}$ receptor antagonist can enhance an immune response against the antigen for an extended period of time, such as for at least one day or more, such as for at least one week.

In certain embodiments, $A_{2a}$ receptor antagonist administration enhances the number of antigen specific memory T cells in a host. In particular embodiments, the number of memory T cells is enhanced 2-5 fold over the number in a control host who has not been administered an antagonist. The immune response can also be an enhancement of a cytokine release, such as IFN-γ release. In particular embodiments, the enhancement of IFN-γ release is 2-5 fold over the amount of IFN-γ release in a control host who has not been administered an antagonist. In yet another embodiment, the immune response is a reduction in regulatory T cells. In yet another embodiment, the $A_{2a}$ receptor antagonist inhibits generation, expansion or stimulation of regulatory T cells. In particular embodiments, the generation, expansion or stimulation of regulatory T cells is enhanced 2-5 fold over the number in a control host who has not been administered an antagonist.

In another embodiment, a method of enhancing an immune response in a host is provided comprising administering an $A_{2a}$ receptor antagonist to the host and subsequently administering an antigen to the host in the absence of the antagonist. In certain embodiments, the method comprises administering an $A_{2a}$ receptor antagonist substantially in combination with a first antigen to the host and subsequently administering a second antigen in the absence of the antagonist. The antigen can be any compound that elicits an immune response, and in non-limiting examples is a viral protein, a bacterial protein, or a mammalian protein. The antigen can be expressed in a *Listeria* species, which can be attenuated for entry into non-phagocytic cells.

In another principal embodiment, a method of treating an infection in a host by enhancing the generation of antigen-specific memory T cells is provided, comprising administering an $A_{2a}$ receptor antagonist to a host carrying an infection for an amount of time and at a concentration sufficient to elicit a memory T cell response, such as a response to the particular antigen, by 2 to 5 fold. The antagonist can also enhance the generation of memory T cells by at least two fold over control. In another embodiment, the antagonist enhances the generation of memory T cells by at least four fold. In one embodiment, the antagonist increases total release of Interferon-γ in the host. The infection can be a chronic infection or an acute infection and can be due to, for example, a virus or a bacteria. In one embodiment, the infection is a chronic infection such as HIV or HCV.

In one principal embodiment, a method of enhancing an immune response in a host is provided comprising administering an $A_{2a}$ receptor antagonist in combination or alternation with a costimulatory molecule to the host. In certain embodiments, the costimulatory molecule enhances CD28 signaling. In certain embodiments, the costimulatory molecule is a fusion protein of a B7 family member. In some embodiments, the costimulatory molecule is a fusion of a B7-H1 or a B7-DC molecule, or a variant thereof. In specific embodiments, the costimulatory molecule is an Fc-fusion of a B7-H1 or B7-DC molecule, a fragment of a B7-H1 or B7-DC molecule, or a variant thereof. In certain cases, the variant can include one or more mutated amino acids when compared to the native protein. In certain embodiments, the costimulatory molecule does not interact with PD-1.

In another embodiment, a method of eliciting an immune response in a host is provided comprising administering to the host an $A_{2a}$ receptor antagonist in combination with an antigen, wherein the antigen is a commercially available antigen, and wherein the amount of antigen administered is reduced by a factor of five beyond the effective dose to elicit an immune response to the antigen in the absence of $A_{2a}$ receptor antagonist. In addition, a kit is provided comprising an $A_{2a}$ receptor antagonist and a dosage unit, in which the dosage unit allows the separation of a dosage of a commercially available antigen into at least one fifth the provided dosage. In one embodiment, the commercially available antigen is a vaccine. In a specific embodiment, the vaccine dosage is reduced by a factor of 10.

In separate principal embodiments, methods of treating or preventing abnormal cell proliferation in a host are provided comprising administering an $A_{2a}$ receptor antagonist to a host at risk of or suffering from a disorder of abnormal cell proliferation, such as cancer. These methods can reduce the risk of developing cancer in the host. In other embodiments, the methods reduce the amount of cancer in a host. In yet other embodiments, the methods reduce the metastatic potential of a cancer in a host. The methods can also reduce the size of a cancer in a host.

In some embodiments, administration of an $A_{2a}$ receptor antagonist reduces tolerance of T cells to a cancer. In these embodiments, the antagonist increases susceptibility of cancer cells to immune rejection. In certain embodiments, the immune response elicited by an $A_{2a}$ antagonist is a reduction in regulatory T cells. In yet other embodiments, the $A_{2a}$ receptor antagonists inhibit generation, expansion or stimulation of regulatory T cells. In further embodiments, the antagonist causes a reduction in T cell anergy. The reduction in T cell anergy can be in tumor-specific T cells.

In one specific embodiment, a method of treating or preventing abnormal cell proliferation in a host is provided comprising administering to a host in need thereof an $A_{2a}$ receptor antagonist in combination or alternation with a mammalian cell based vaccine, which can be a whole mammalian cell such as a tumor cell that is not actively dividing and can be genetically modified to secrete an activation factor for an antigen-presenting cell such as a granulocyte-macrophage colony stimulating factor (GM-CSF). In other embodiments, the cell based vaccine comprises a dendritic cell or a dendritic cell formulation.

In one embodiment, the $A_{2a}$ receptor antagonist reduces tolerance of T cells to a cell in the cell based vaccine. In this embodiment, the antagonist increases susceptibility of tumor cells to immune rejection. In one embodiment, the immune response is a reduction in regulatory T cells. In one embodiment, the antagonist enhances generation of memory T cells. In yet another embodiment, the $A_{2a}$ receptor antagonist inhibits generation, expansion or stimulation of regulatory T cells. In another embodiment, the antagonist causes a reduction in T cell anergy. The reduction in T cell anergy can be in tumor-specific T cells. In some embodiments, the changes in T cell responses are specific to the particular antigen.

In another principal embodiment, a method of treating or preventing abnormal cell proliferation is provided comprising administering an $A_{2a}$ receptor antagonist to a host in need thereof substantially in the absence of another anti-cancer agent.

In another principal embodiment, a method of treating or preventing abnormal cell proliferation in a host in need thereof is provided, comprising administering a first $A_{2a}$ receptor antagonist substantially in combination with a first anti-cancer agent to the host and subsequently administering a second $A_{2a}$ receptor antagonist. In one subembodiment, the second antagonist is administered substantially in the absence of another anti-cancer agent. In another principal embodiment, a method of treating or preventing abnormal cell proliferation in a host in need thereof is provided, comprising administering an $A_{2a}$ receptor antagonist substantially in combination with a first anti-cancer agent to the host and subsequently administering a second anti-cancer agent in the absence of the antagonist.

Alternative embodiments of the present invention relate to the use of $A_{2a}$ receptor agonists, rather than antagonists. Many drugs have been shown to inhibit T cells responses, for example Cyclosporin A. However, such agents require continuous administration. That is, when the drug is stopped the T cells can become activated again. It has now been found that $A_{2a}$ receptor agonists can stimulate long term T cell tolerance. As such, a finite treatment of $A_{2a}$ receptor agonists will lead to tolerance thus abrogating the need for chronic immunosuppression. In particular, $A_{2a}$ receptor agonists can reduce the need for continued immunosuppression in preventing or treating autoimmune diseases or disorders, for example in preventing transplant rejection or Graft versus Host Disease.

In one embodiment, a method of inducing immune tolerance in a host in need thereof is provided comprising administering an $A_{2a}$ receptor agonist to the host, wherein the tolerance is induced for at least one week. The administration of the agonist can be in a single administration, or can be in a short term regimen. In one embodiment, the administration is a short term regimen of two weeks or less. The tolerance can be specific to an antigen or can be general tolerance of T cells in the host.

In acute response instances, for example in an organ transplantation situation, an $A_{2a}$ agonist can be administered at least daily for a period of weeks to months during and after the transplantation. In chronic situations, such as an autoimmune disease, the agonist can be administered during a 'flare up'. In other embodiments, the agonist is not administered during a 'flare up', but is administered when no agent to decrease inflammation is necessary. In certain embodiments, the agonist is administered during a 'flare up', but then is additionally administered after inflammation is no longer apparent to increase auto-tolerance.

In one embodiment, the $A_{2a}$ agonist is administered in combination with an immunosuppressive agent. In some embodiments, the $A_{2a}$ agonist is administered in combination with an immunosuppressive agent and subsequently, the $A_{2a}$ agonist is administered in the absence of the immunosuppressive agent.

In a specific embodiment, the host is in need of immunosuppressive therapy. In one embodiment, the host is being treated with an immunosuppressive therapy. In certain embodiments, administration of the $A_{2a}$ receptor agonist reduces the amount of immunosuppressive therapy administered to the host. In certain embodiments, an immunosuppressive agent is not administered to the host receiving the agonist.

In some embodiments, the $A_{2a}$ receptor agonist is administered to a host who has failed immunosuppressive therapy or refractory thereto. In certain instances, the host has an immune response, for example an organ rejection, while being administered immunosuppressive therapy. In certain embodiments, administration of the $A_{2a}$ agonist reduces immune responses against an antigen. In some instances, the antigen can be administered to the host in combination or alternation with the agonist to cause T cell tolerance to the antigen.

In one particular embodiment, the host is suffering from or at risk of an autoimmune disease or disorder. In another embodiment, the host is a recipient of a transplanted tissue or organ. In a particular embodiment, the host is at risk of organ rejection.

In certain embodiments, the $A_{2a}$ agonist is administered in combination or alternation with a checkpoint blocker such as B7-H4 or fragments or variants thereof.

BRIEF DESCRIPTION OF THE DRAWINGS

FIG. 3(a) is a graph of the percentage of $A_{2a}$ receptor Wt or KO T cells that were IFN-γ positive upon rechallenge following incubation with peptide in the absence (solid bars) or presence (open bars) of 1 µM CGS. 3(b) is a graph showing fold increase in LAG-3 expression in cells. CD4$^+$, 6.5$^+$ primary T cells were cultured with irradiated APCs and HA±1 µM CGS for 3 days. mRNA was harvested and assayed for abundance of LAG-3 transcripts. Data are representative of 3 independent experiments. 3(c) is a graph of LAG3 upregulation in A.E7 T cells following stimulation with ionomycin or PMA. 3(d) is an image of representative Western blots for phosphor-ERK and total ERK (top and bottom respectively). Activated CD4$^+$, 6.5$^-$ primary T cells were stimulated with signals 1 and 2 in the absence or presence of 1 µM CGS. Data are representative of 3 independent experiments. 3(e) is an image of representative Western blots for junB, and actin (top and bottom, respectively). CD4$^-$, 6.5$^+$ primary T cells were stimulated with HA and irradiated APCs overnight in the absence or presence of 1 µM CGS. Data are representative of 3 independent experiments. 3(f) is an image of representative EMSA for AP-1. CD4$^+$, 6.5$^+$ primary T cells were stimulated with HA and irradiated APCs overnight in the absence or presence of 1 µM CGS. Data are representative of 3 independent experiments.

FIG. 4(a) is a survival curve of C3HA mice given 6.5$^+$ T cells and 4 days of vehicle (open squares) or CGS (2.5 mg/kg, solid diamonds) (n=17 mice, each condition). FIGS. 4(b) & (c) show graphs of in vitro proliferation (b), and IFN-γ production (c) of T cells harvested from vehicle- or CGS-treated C3HA mice (open and solid bars, respectively). Data are representative of 2 independent experiments, ≥3 mice per group. (*: p>0.05) FIG. 4(d) shows a survival curve of C3HA mice given Wt (grey diamonds) or $A_{2a}$ receptor null 6.5 T cells and treated with vehicle or CGS (open circles and open triangles, respectively) (n=5 each condition).

FIG. 5(a) shows a graph of LAG-2 expression in clonotypic 6.5$^+$ T cells that were transferred into C3HA mice which were treated with vehicle or CGS (3 days after adoptive transfer), and sorted to >98% purity. LAG-3 expression was determined by RT-PCR. 5(b) shows a graph of relative LAG-3 expression of $A_{2a}$ receptor wild type or null 6.5$^+$ T cells. For A-B, data are representative of 3 independent experiments, 3 mice per group. 5(c) shows a survival curve of C3HA mice given wild type or LAG-3 knock out T cells and a 4 day treatment with CGS. (n=5 mice, each condition) 5(d) shows a graph of percent survival in which vehicle- or CGS-treated C3HA mice (the survivors of FIG. 5(a); open squares [n=4] or grey diamonds [n=13], respectively) were given a higher dose of 6.5+ T cells. Naïve mice (open triangles, [n=17]) received only this higher dose of 6.5+ T cells. No drug was administered during this experiment.

DETAILED DESCRIPTION OF THE INVENTION

Figure 1:
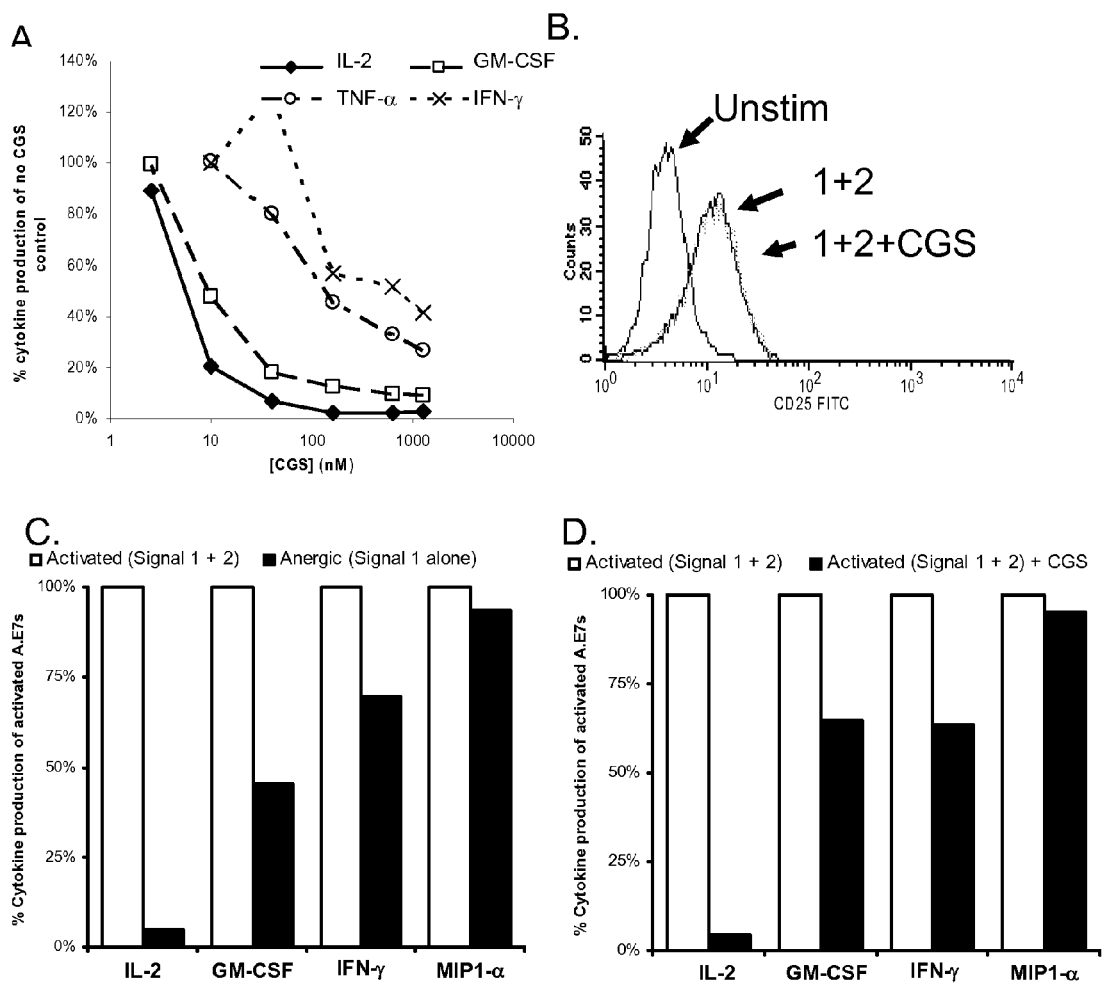
FIGS. 1(a)-(d) are graphs showing $A_{2a}$ receptor signaling during T cell activation mimics Signal 1 alone. 1(a) is a graph of IL-2, GM-CSF, TNF-α, and IFN-γ levels (solid diamonds, hollow squares, hollow circles and crosses, respectively) of A.E7s stimulated with anti-CD3 and anti-CD28 in increasing doses of CGS (denoted on X axis). 1(b) is a graph of surface expression of CD25 of A.E7s after activation with anti-CD3 and anti-CD28 in the presence (grey) or absence (black) of 1 µM CGS. Data are representative of 3 separate experiments. 1(c) & (d) are graphs of the cytokine profile of anergic A.E7s (c) or A.E7s stimulated with anti-CD3 and anti-CD28 and 20 nM CGS (d). Data are represented as percentage of A.E7s stimulated with anti-CD3 and anti-CD28, and is the average of 3 separate experiments.

Adenosine $A_{2a}$ Receptor Antagonists for Enhancing Immune Responses
Methods of Enhancing Response to Antigens It has been discovered that $A_{2a}$ receptors are responsible for induction of long term T cell tolerance. These receptors can induce tolerance both by promoting T cell anergy, under which T cells fail to respond to an antigen upon re-challenge even under normally activating conditions, and by inducing regulatory T cells, which are responsible for maintained tolerance. It has now been found that $A_{2a}$ receptor antagonists can overcome T cell tolerance and thus stimulate long term responses to certain antigens.

In one principal embodiment, methods are provided for enhancing an immune response to a specific antigen in a host in need thereof.

In one principal embodiment, a method of enhancing an immune response to an antigen in a host is provided, comprising administering a first $A_{2a}$ receptor antagonist substantially in combination with an antigen to the host and subsequently administering a second $A_{2a}$ receptor antagonist in the absence of the antigen.

In one embodiment, the first and second $A_{2a}$ receptor antagonists are the same. In another embodiment, the first and second $A_{2a}$ receptor antagonists are different. In one embodiment, the first antagonist and antigen are administered in the same preparation. In another embodiment, the antagonist and antigen are administered concurrently in separate preparations. In another embodiment, the antagonist and antigen are administered within the same day.

In one subembodiment, the second $A_{2a}$ receptor antagonist is administered at least one day after administration of the antigen. In another subembodiment, the second antagonist is administered at least one week after administration of the antigen. In another embodiment, the second antagonist is administered at least one day after administration of the antigen and the method includes further administering the second antagonist at least two times. The second antagonist can be administered at least twice, at least three times, at least four times, at least five times, at least six times, at least seven times, at least eight times, at least nine times, at least ten times or more, or between 2 and 20, between 2 and 15, between 2 and 10 or fewer times. The administration can be every day, or can be less, such as every two days, every three days, every four days, every five days, every six days, every seven days or less, such as every two weeks, once a month, once every two months, four times a year, three times a year, two times a year or once a year.

In one embodiment, the first $A_{2a}$ receptor antagonist enhances an immune response against the antigen. In certain embodiments, the antagonist enhances the number of antigen specific memory T cells in a host. In another embodiment, the immune response is an enhancement of effector cytokine release. In certain embodiments, this is IFN-γ release. In yet another embodiment, the immune response is a reduction in regulatory T cells.

In one embodiment, the first $A_{2a}$ receptor antagonist stimulates an immune response for at least one day. In another embodiment, the first antagonist stimulates an immune response for at least one week. In yet another embodiment, the $A_{2a}$ receptor antagonist inhibits generation, expansion or stimulation of regulatory T cells.

In one embodiment, the antigen is a viral protein. In another embodiment, the antigen is a bacterial protein or a portion thereof. In yet another embodiment, the antigen is a mammalian protein or a portion thereof.

In certain embodiments, the antigen is expressed in a *Listeria* species. The *Listeria* species can be a *Listeria monocytogenes*. Methods of producing *Listeria* vaccines, including *Listeria* species expressing antigens of interest are discussed in U.S. Patent Application Publication Nos. 2004/0228877, 2005/0249748 and 2005/0281783. In certain embodiments, the *Listeria* species is attenuated for entry into non-phagocytic cells as compared to a wild type *Listeria* species. In certain cases, the *Listeria* species is one in which the in1B gene has been deleted (i.e., a strain attenuated for entry into non-phagocytic cells, for example, hepatocytes via the c-met receptor) or both the actA gene and the in1B genes have been deleted (i.e., a strain attenuated for both entry into non-phagocytic cells and cell-to-cell spread).

In one embodiment, a method of enhancing an immune response in a host is provided comprising administering an $A_{2a}$ receptor antagonist to the host and subsequently administering an antigen in the absence of the antagonist.

In one subembodiment, the antigen is administered at least one day after administration of the antagonist. In another subembodiment, the antigen is administered at least one week after administration of the antagonist. In another embodiment, the antigen is administered at least one day after administration of the antagonist and the method includes further administering the antagonist at least two times. The antagonist can be administered at least twice, at least three times, at least four times, at least five times, at least six times, at least seven times, at least eight times, at least nine times, at least ten times or more, or between 2 and 20, between 2 and 15, between 2 and 10 or fewer times. The administration can be every day, or can be less, such as every two days, every three days, every four days, every five days, every six days, every seven days or less, such as every two weeks, once a month, once every two months, four times a year, three times a year, two times a year or once a year.

In one embodiment, the $A_{2a}$ receptor antagonist enhances an immune response against the antigen. In certain embodiments, the antagonist enhances the number of antigen specific memory T cells in a host. In another embodiment, the immune response is an enhancement of IFN-γ release. In yet another embodiment, the immune response is a reduction in regulatory T cells.

In one embodiment, the $A_{2a}$ receptor antagonist stimulates an immune response for at least one day. In another embodiment, the antagonist stimulates an immune response for at least one week. In yet another embodiment, the $A_{2a}$ receptor antagonist inhibits generation, expansion or stimulation of regulatory T cells.

In one principal embodiment, a method of enhancing an immune response to an antigen in a host is provided, comprising administering an $A_{2a}$ receptor antagonist substantially in combination with a first antigen to the host and subsequently administering a second antigen in the absence of the antagonist.

In one subembodiment, the second antigen is administered at least one day after administration of the antagonist. In another subembodiment, the second antigen is administered at least one week after administration of the antagonist. In another embodiment, the second antigen is administered at least one day after administration of the antagonist and the method includes further administering the second antigen at least two times. The second antigen can be administered at least twice, at least three times, at least four times, at least five times, at least six times, at least seven times, at least eight times, at least nine times, at least ten times or more, or between 2 and 20, between 2 and 15, between 2 and 10 or fewer times. The administration can be every day, or can be less, such as every two days, every three days, every four days, every five days, every six days, every seven days or less, such as every two weeks, once a month, once every two months, four times a year, three times a year, two times a year or once a year.

In one embodiment, the $A_{2a}$ receptor antagonist enhances an immune response against the second antigen. In certain embodiments, the antagonist enhances the number of second antigen specific memory T cells in a host. In another embodiment, the immune response is an enhancement of IFN-γ release. In yet another embodiment, the immune response is a reduction in regulatory T cells.

In one embodiment, the $A_{2a}$ receptor antagonist stimulates an immune response for at least one day. In another embodiment, the antagonist stimulates an immune response for at least one week. In yet another embodiment, the $A_{2a}$ receptor antagonist inhibits generation, expansion or stimulation of regulatory T cells.

In another principal embodiment, a method of treating an infection in a host by enhancing the generation of antigen-specific memory T cells is provided, comprising administering an $A_{2a}$ receptor antagonist to a host carrying an infection for an amount of time and at a concentration sufficient to elicit a memory T cell response, such as from 2 to 5 fold over the number in a control host who has not been administered an antagonist. In certain embodiments, the memory T cell number is enhanced by a factor of 2, by a factor of 3, by a factor of 4, by a factor of 5, by a factor of 6, by a factor of 7, by a factor of 8, by a factor of 9, by a factor of 10 or more, either when compared to a control host who has not been administered the antagonist, or in comparison to the memory T cell level that existed in the host prior to administration of the antagonist. In some instances, the memory T cell response is an increase in tolerance of these cells. In some cases, it is a number of cells. In some instances, it is a decrease in cell anergy. In some embodiments, the response is measured by an increase in IFN-γ release. In another embodiment, the response is measured using flow cytometry based on tetramers of labeled antigen-MHC. In another embodiment, the response is measured using a limiting dilution assay such as an Enzyme-linked immunosorbent spot assay (Elispot). In another embodiment, the response is measured using intracellular staining.

In one subembodiment, the infection is a chronic infection. In another subembodiment, the infection is an acute infection. In one embodiment, the infection is due to a virus. In another embodiment, the infection is due to a bacteria. In one embodiment, the infection is a chronic infection such as HIV.

In one embodiment, the antagonist enhances the generation of memory T cells by at least two fold over control. In another embodiment, the antagonist enhances the generation of memory T cells by at least four fold. In one embodiment, the antagonist increases total release of Interferon-γ in the host.

In one principal embodiment, a method of enhancing an immune response in a host is provided comprising administering an $A_{2a}$ receptor antagonist in combination or alternation with a costimulatory molecule to the host. In certain embodiments, the costimulatory molecule enhances CD28 signaling. In certain embodiments, the costimulatory molecule is a fusion protein of a B7 family member with a molecule that is not a B7 family member, for example with an Fc molecule. In some embodiments, the costimulatory molecule is a fusion of a B7-H1 or a B7-DC molecule, or a variant thereof. In certain embodiments, the costimulatory molecule does not interact with PD-1.

In another principal embodiment, a method of eliciting an immune response in a host is provided comprising administering an $A_{2a}$ receptor antagonist in combination with an antigen to the host, wherein the antigen is a commercially available antigen, and wherein the amount of antigen administered to elicit a prophylactically or therapeutically effective immune response is reduced by a factor of five beyond the effective dose in the absence of $A_{2a}$ receptor antagonist. In addition, a kit is provided comprising an $A_{2a}$ receptor antagonist, a dosage unit, in which the dosage unit allows the separation of a dosage of a commercially available antigen into at least one fifth the provided dosage. In one embodiment, the commercially available antigen is a vaccine. In a specific embodiment, the vaccine dosage is reduced by at least a factor of 10. In other embodiments, it is reduced by less than a factor of 10, such as by a factor of 2, by a factor of 3, by a factor of 4, by a factor of 5, by a factor of 6, by a factor of 7, by a factor of 8 or by a factor of 9.

Methods of Treating or Preventing Abnormal Cell Proliferation

In separate principal embodiments, methods of treating or preventing abnormal cell proliferation in a host are provided. The host can be a mammal and in particular embodiments is a human.

These methods can reduce the risk of developing cancer in the host. In other embodiments, the methods reduce the amount of cancer in a host. In yet other embodiments, the methods reduce the metastatic potential of a cancer in a host. The methods can also reduce the size of a cancer in a host.

In some embodiments, administration of an $A_{2a}$ receptor antagonist reduces tolerance of T cells to a cancer. In these embodiments, the antagonist increases susceptibility of cancer cells to immune rejection. In certain embodiments, the immune response elicited by an $A_{2a}$ antagonist is a reduction in regulatory T cells. In yet other embodiments, the $A_{2a}$ receptor antagonist inhibits generation, expansion or stimulation of regulatory T cells. In further embodiments, the antagonist causes a reduction in T cell anergy. The reduction in T cell anergy can be in tumor-specific T cells.

In one specific embodiment, a method of treating or preventing abnormal cell proliferation in a host is provided comprising administering to a host in need thereof an $A_{2a}$ receptor antagonist in combination or alternation with a mammalian cell based vaccine.

In one embodiment, the method reduces the risk of developing cancer in the host. In another embodiment, the method reduces the amount of cancer in a host. In yet another embodiment, the method reduces the metastatic potential of a cancer in a host. In yet another embodiment, the method reduces the size of a cancer in a host.

In one embodiment, the mammalian cell based vaccine is a whole mammalian cell. In certain embodiments, the vaccine is a tumor cell that is not actively dividing. The tumor cell can be irradiated. In certain embodiments, the cell is genetically modified. In some embodiments, the cell can be secreting an activation factor for an antigen-presenting cell. In certain embodiments, the cell secretes, for example constitutively secretes, a colony stimulating factor and can specifically secrete a granulocyte-macrophage colony stimulating factor (GM-CSF). The cell based vaccine can also be based on a dendritic cell or dendritic cell formulation. The cell can be based on cells from the same type of tissue as the tumor. In certain embodiments, the cell is derived from a prostate cancer cell. In other embodiments, the cell is derived from a breast cancer cell. In other instances, the cell is derived from a lymphoma cell.

In one embodiment, the $A_{2a}$ receptor antagonist reduces tolerance of T cells to a cell in the cell based vaccine. In this embodiment, the antagonist increases susceptibility of tumor cells to immune rejection. In one embodiment, the immune response is a reduction in regulatory T cells. In one embodiment, the antagonist enhances generation of memory T cells. In yet another embodiment, the $A_{2a}$ receptor antagonist inhibits generation, expansion or stimulation of regulatory T cells. In another embodiment, the antagonist causes a reduction in T cell anergy. The reduction in T cell anergy can be in tumor-specific T cells.

In one embodiment, the antagonist and cell based vaccine are administered in combination. In certain of these embodiments, the antagonist and vaccine are administered concurrently in the same preparation. In other embodiments, the antagonist and vaccine are administered concurrently in separate preparations. In other embodiments, the antagonist is administered before administration of the vaccine. In some embodiments, the vaccine is administered at least one hour, at least 8 hours, at least 1 day, at least 2 days, at least 3 days, at least 4 days, at least 5 days, at least 6 days, at least 7 days, at least 8 days, at least 9 days, at least 10 days or more after administration of the antagonist. In certain embodiments, the antagonist and vaccine are administered in multiple rounds. In specific embodiments, the antagonist and vaccine are administered at least 2, at least 3, at least 4, at least 5, at least 6, at least 7, at least 8 at least 9 or at least 10 times.

In some embodiments, the method further comprises administering a second $A_{2a}$ receptor antagonist in the absence of the vaccine. In some embodiments, the second $A_{2a}$ receptor antagonist is different than the first antagonist. In other embodiments, the second antagonist is the same as the first antagonist. In this embodiment, the further administration can occur at least 1, at least 2, at least 3, at least 4, at least 5, at least 6, at least 7, at least 8 at least 9 or at least 10 days, or at least 1 week, a least 2 weeks, at least 3 weeks, at least 1 month, at least 2 months, at least 3 months, at least 4 months, at least 5 months, at least 6 months or more after administration of the vaccine.

In some embodiments, a method of inhibiting abnormal cell proliferation is provided comprising administering an $A_{2a}$ receptor antagonist in combination or alternation with a mammalian cell based vaccine and further administering an anti-cancer agent.

In another principal embodiment, a method of treating or preventing abnormal cell proliferation is provided comprising administering an $A_{2a}$ receptor antagonist to a host in need thereof substantially in the absence of an anti-cancer agent.

In one embodiment, the $A_{2a}$ receptor antagonist reduces tolerance of T cells to a cancer. In this embodiment, the antagonist increases susceptibility of the cancer cells to immune rejection. In one embodiment, the immune response is a reduction in regulatory T cells. In yet another embodiment, the $A_{2a}$ receptor antagonist inhibits generation, expansion or stimulation of regulatory T cells. In another embodiment, the antagonist causes a reduction in T cell anergy. The reduction in T cell anergy can be in tumor-specific T cells.

In one embodiment, the first $A_{2a}$ receptor antagonist stimulates an immune response for at least one day. In another embodiment, the first antagonist stimulates an immune response for at least one week or more.

In another principal embodiment, a method of treating or preventing abnormal cell proliferation in a host in need thereof is provided, comprising administering a first $A_{2a}$ receptor antagonist substantially to a host in combination with a first anti-cancer agent and subsequently administering a second $A_{2a}$ receptor antagonist.

In one embodiment, the first and second $A_{2a}$ receptor antagonists are the same. In another embodiment, the first and second $A_{2a}$ receptor antagonists are different. In one embodiment, the first antagonist and anti-cancer agent are administered in the same preparation. In another embodiment, the antagonist and anti-cancer agent are administered concurrently in separate preparations. In another embodiment, the antagonist and anti-cancer agent are administered within the same day.

In one subembodiment, the second antagonist is administered substantially in the absence of an anti-cancer agent. In one subembodiment, the second $A_{2a}$ receptor antagonist is administered at least one day after administration of the anti-cancer agent. In another subembodiment, the second antagonist is administered at least one week after administration of the anti-cancer agent. In another embodiment, the second antagonist is administered at least one day after administration of the anti-cancer agent and the method includes further administering the second antagonist at least two times. The second antagonist can be administered at least twice, at least three times, at least 4 times, at least 5 times, at least 6 times, at least 7 times, at least 8 times, at least 9 times, at least 10 times or more, or between 2 and 20, between 2 and 15, between 2 and 10 or fewer times. The administration can be every day, or can be less often, such as every two days, every three days, every four days, every five days, every six days, every seven days or less, such as every two weeks, once a month, once every two months, four times a year, three times a year, two times a year or once a year.

In one embodiment, the first $A_{2a}$ receptor antagonist reduces tolerance of T cells to a cancer. In one embodiment, the antagonist increases susceptibility of the cancer cell to an anti-cancer agent. In another embodiment, the antagonist increases susceptibility of the cancer cells to immune rejection.

In one embodiment, the first $A_{2a}$ receptor antagonist stimulates an immune response for at least one day. In another embodiment, the first antagonist stimulates an immune response for at least one week. In yet another embodiment, the $A_{2a}$ receptor antagonist inhibits generation, expansion or stimulation of regulatory T cells.

In another principal embodiment, a method of treating or preventing abnormal cell proliferation in a host in need thereof is provided, comprising administering an $A_{2a}$ receptor antagonist to the host substantially in combination with a first anti-cancer agent and subsequently administering a second anti-cancer agent in the absence of the antagonist.

In one embodiment, the first and second anti-cancer agent are the same. In another embodiment, the first and second anti-cancer agent are different. In one embodiment, the antagonist and first anti-cancer agent are administered in the same preparation. In another embodiment, the antagonist and first anti-cancer agent are administered concurrently in separate preparations. In another embodiment, the antagonist and first anti-cancer agent are administered within the same day.

In one subembodiment, the second anti-cancer agent is administered at least one day after administration of the antagonist. In another subembodiment, the second anti-cancer agent is administered at least one week after administration of the antagonist. In another embodiment, the second anti-cancer agent is administered at least one day after administration of the antagonist and the method includes further administering the second anti-cancer agent at least two times. The second anti-cancer agent can be administered at least twice, at least three times, at least four times, at least five times, at least six times, at least seven times, at least eight times, at least nine times, at least ten times or more, or between 2 and 20, between 2 and 15, between 2 and 10 or fewer times. The administration can be every day, or can be less, such as every two days, every three days, every four days, every five days, every six days, every seven days or less, such as every two weeks, once a month, once every two months, four times a year, three times a year, two times a year or once a year.

In one embodiment, the $A_{2a}$ receptor antagonist reduces tolerance of T cells to a cancer. In one embodiment, the antagonist increases susceptibility of the cancer cell to the second anti-cancer agent. In another embodiment, the antagonist increases susceptibility of the cancer cells to immune rejection.

In one embodiment, the $A_{2a}$ receptor antagonist stimulates an immune response for at least one day. In another embodiment, the antagonist stimulates an immune response for at least one week. In yet another embodiment, the $A_{2a}$ receptor antagonist inhibits generation, expansion or stimulation of regulatory T cells.

Adenosine Antagonists

Any molecule that is an antagonist at an $A_{2a}$ adenosine receptor can be useful in the methods of this invention. Examples include, but are not limited to, a pharmacological antagonist, a gene therapy agent, a ribozyme, an antisense oligonucleotide, or another catalytic nucleic acid that selectively binds mRNA encoding an adenosine receptor, and agents that reduce total levels of adenosine in a tissue. In certain embodiments, the antagonists are non-selective antagonists. In certain other embodiments, the antagonists are selective antagonists.

Caffeine (1,7-methylxantine), along with theophylline have been found to antagonize both A1 and $A_{2a}$ receptors in the brain. Flavonoids (from a variety of dietary plants, and e.g. soy) inhibit adenosine receptor stimulation, when present in the micromolar range, for example galangin. Specific antagonists of the $A_{2a}$ receptor include SCH-58261 (7-(2-phenylethyl)-5-amino-2-(2-furyl)-pyrazolo-[4,3-e]-1,2,4-triazolo[1,5-c]-pyrimidine), ZM 241385, MRS 1220; theobromin; ADA-PEG (polyethylene glycol-modified ADA that has been used in treatment of patients with ADA SCID (Hershfield, Hum Mutat. 5:107, 1995)); CSC, KF17837, MRA470, CTS21680, CVT3146 and some xanthine derivatives, including KW6002 ((E)-1,3-diethyl-8-(3,4-dimethoxystyryl)-7-methyl-3,7-dibydro-1H-purine-2,6-dione). Particular non limiting examples of antagonists are described in U.S. Pat. Nos. 5,565,566; 5,545,627, 5,981,524; 5,861,405; 6,066,642; 6,326,390; 5,670,501; 6,117,998; 6,232,297; 5,786,360; 5,424,297; 6,313,131, 5,504,090; and 6,322,771. Partial agonists/antagonists may be present in *Hypericum perforatum* and *Valeriana officinalis*. In addition, selective antagonists are being developed by Adenosine Therapeutics.

Inhibitors of extracellular adenosine are also generally contemplated for use in the methods of the invention. These include agents or compositions that decreases the activity or level of extracellular adenosine. Examples include, but are not limited to, agents that degrade extracellular adenosine, render extracellular adenosine inactive, and/or decrease or prevent the accumulation or formation of extracellular adenosine. Particular examples include, but are not limited to, enzymes such as adenosine deaminase, adenosine kinase, and adenosine kinase enhancers; oxygenation; redox-potential changing agents which diminish the degree of hypoxia-ischemia; and other catalytic agents that selectively bind and decrease or abolish the ability of endogenously formed adenosine to signal through adenosine receptors.

In another example, the antagonist is an antisense molecule or catalytic nucleic acid molecule (e.g. a ribozyme) that specifically binds mRNA encoding an adenosine receptor. In certain embodiments, the antagonist is an siRNA molecule that reduces expression of an $A_{2a}$ adenosine receptor in at least one cell in a host. In specific, non-limiting examples, the antisense molecule, siRNA molecule or catalytic nucleic acid molecule binds $A_{2a}$ receptor. In a further example, an antisense molecule, siRNA molecule or catalytic nucleic acid molecule targets biochemical pathways downstream of the adenosine receptor. For example, the antisense molecule, siRNA molecule or catalytic nucleic acid molecule can inhibit an enzyme involved in the Gs-dependent intracellular pathway. Adenosine receptor protein expression in a host cell can be reduced by introducing into cells an antisense construct or another genetic sequence-targeting agent $A_{2a}$ locus (e. g. Genbank accession number AH003248). In some embodiments, the antagonist is an siRNA molecule that targets and causes degradation of an mRNA molecule encoding the $A_{2a}$ receptor. An antisense construct includes the reverse complement of the adenosine receptor cDNA coding sequence, the adenosine receptor cDNA or gene sequence or flanking regions thereof. For antisense suppression, a nucleotide sequence from the adenosine receptor locus (e.g. all or a portion of the adenosine receptor cDNA or gene or the reverse complement thereof) is arranged in reverse orientation relative to the promoter sequence in a vector, which is introduced into a cell of interest. Antisense molecule construction and siRNA construction follow similar patterns.

The introduced sequence need not be the full-length human adenosine receptor cDNA or gene or reverse complement thereof, and need not be exactly homologous to the equivalent sequence found in the cell type to be transformed. In one example, the introduced antisense sequence in the vector is at least 10, such as at least 30 nucleotides in length. Improved antisense suppression is typically observed as the length of the antisense sequence increases. Shorter polynucleotide (oligonucleotides) can conveniently be produced synthetically as well as in vivo. In specific aspects, the oligonucleotide is at least 10 nucleotides, at least 15 nucleotides, at least 30, at least 100 nucleotides, or at least 200 nucleotides. The oligonucleotides can be DNA or RNA, or chimeric mixtures or derivatives or modified versions thereof, single-stranded or double-stranded. An antisense polynucleotide can be conjugated to another molecule, for example a peptide, hybridization triggered cross-linking agent, transport agent, or hybridization-triggered cleavage agent. In some embodiments, the signal of the receptor is blocked. This can be by antagonism of the cAMP cascade, of MAP kinases, of PKA, of PLD, of Epac, or of other related downsteam signals, or by reduction of the expression of the $A_{2a}$ receptor.

Suppression of endogenous adenosine receptor locus expression can also be achieved using catalytic nucleic acids such as ribozymes. Ribozymes are synthetic RNA molecules that possess highly specific endoribonuclease activity. The production and use of ribozymes are disclosed in U.S. Pat. No. 4,987,071 to Cech and U.S. Pat. No. 5,543,508 to Haselhoff. Ribozyrnes can be synthesized and administered to a cell or a subject, or can be encoded on an expression vector, from which the ribozyme is synthesized in the targeted cell (as in PCT publication WO 9523225, and Beigelman et al. Nucl. Acids Res. 23:4434-42, 1995). Examples of oligonucleotides with catalytic activity are described in WO 9506764, WO 9011364, and Sarver et al. (Science 247: 1222-5, 1990).

In another example, local tissue accumulation of extracellular adenosine is inhibited using a preparation of adenosine deaminase (ADA). This can be, for example, an enzyme, adenosine deaminase or a ribozyme, or another catalytic molecule that selectively binds and destroys adenosine, thereby abolishing, or substantially decreasing, the ability of endogenously-formed adenosine to signal through adenosine receptors and terminate inflammation. The propagation of adenosine receptor-triggered intracellular signaling cascade can also be affected by the use of specific inhibitors of enzymes and proteins that are involved in regulation of synthesis and/or secretion of pro-inflammatory molecules, including modulators of nuclear transcription factors. Suppression of adenosine receptor expression or expression of the Gs protein- or Gi protein dependent intracellular pathway, or the cAMP dependent intracellular pathways, can also be used.

In certain embodiments, the $A_{2a}$ receptor antagonist is linked to a molecule to increase bioavailability and/or stability. The antagonist can also be linked to a molecule that allows targeting of the antibody to particular tissues or regions, or to 'present' the drug to T cells. In certain instances, this molecule is a polymer such as a polyethylene glycol moiety. In other instances, the molecule is an antibody or a fragment of an antibody such as an Fc region. In specific instances, the antagonist is linked to an Fc region of an antibody.

Co-Stimulatory Molecules

In addition to antigen-specific signals mediated through the T-cell receptor, T cells also require antigen nonspecific costimulation for activation. The B7 family of molecules on antigen-presenting cells, which include B7-1 (CD80) and B7-2 (CD86), play important roles in providing costimulatory signals required for development of antigen-specific immune responses. The CD28 molecule on T cells delivers a costimulatory signal upon engaging either of its ligands, B7.1 (CD80) or B7.2 (CD86) and possibly B7.3. A distinct signal is transduced by the CD40L (for ligand) molecule on the T cell when it is ligated to CD40. A number of other molecules on the surface of APC may serve some role in costimulation, although their full role or mechanism of action is not clear. These include VCAM-1, ICAM-1 and LFA-3 on APC and their respective ligands VLA-4, LFA-1 and CD2 on T cells. It is likely that the integrins LFA-1 and VCAM-1 are involved in initiating cell-cell contact. LFA-1 (lymphocyte function associated protein 1) which blocks killing of target cells by CD8 cytotoxic T cells. LFA-1 binds the immunoglobulin superfamily ligands ICAM-1, -2, -3. Blocking β-2 integrin is a very effective way of inhibiting immune responses and monoclonal antibodies against this protein are in clinical trial for treatment of transplant recipients and other conditions. Other immunotherapeutics in development are CTLA-Ig, which is a soluble from of a high affinity receptor for B7.1 and B7.2 (more avid than CD28), and anti-CD40L. Both block co-stimulation of T cells and anti-CD40L may also block reciprocal activation of antigen presenting cells.

In some embodiments, the antagonist is administered in combination or alternation with an agent that activates a CD28 pathway. In certain instances, this costimulatory molecule is a B7.1 or B7-2 or B7-3 molecule. In certain instances, the costimulatory molecule is a B7-DC or B7-H1 molecule, and in particular a protein fusion of B7-DC, B7-H1, variants of these or truncates thereof with a non-B7 molecule. Certain B7 molecules are described in PCT Publications WO 08/083169, WO 08/067071, WO 07/082154, WO 06/012232, WO 02/10187, WO 01/64704 and U.S. Pat. Nos. 7,030,219, 6,803,192 and 6,891,030. In specific embodiments, the costimulatory molecule is an Fc-fusion of a B7-H1 or B7-DC molecule, a fragment of a B7-H1 or B7-DC molecule, or a variant thereof. In certain cases, the variant can include one or more mutated amino acids when compared to the native protein. In certain embodiments, the costimulatory molecule does not interact with PD-1. In other embodiments, the antagonist is administered in combination or alternation with an antibody that blocks interaction of soluble B7-H4 with its ligand. In certain embodiments, the costimulatory molecule is encoded by a vector derived from a virus. For example a costimulatory molecule can be encoded by a vector derived from a canarypox virus, ALVAC. In some embodiments, the costimulatory molecule is B7.1, encoded by a vector derived from the canarypox virus, ALVAC (ALVAC-B7.1), alone or with another molecule, such as interleukin 12 (ALVAC-IL-12).

Checkpoint inhibitors can also be used in conjunction with the antagonists of the invention. For example, inhibitors of PD-1 could be used to reduce inhibition of T cell activity. In addition, molecules such as soluble B7-H4 can be used to stimulate T cell activities.

In certain embodiments, the $A_{2a}$ antagonists are administered in combination or alternation with a specific human or humanized antibody directed against a therapeutic target. The specific antibody generally acts as a passive vaccine, providing immediate immunity against certain agents. The antibody can be directed against agents such as anthrax, toxins produced by *Clostridium botulinum*, Brucellosis, Q fever (caused by *Coxiella burnetii*), smallpox, viral meningoencephalitis syndromes (including Eastern equine encephalomyelitis virus (EEEV), Venezuelan equine encephalomyelitis virus (VEEV), and Western equine encephalomyelitis virus (WEEV)), viral hemorrhagic fevers (including Ebola, Marburg, and Junin), tularemia, biological toxins (including those causing diphtheria, tetanus, botulism, venoms, ricin, trichothecene mycotoxins, and staphylococcal enterotoxins) and plague.

Anti-Cancer Agents

In certain embodiments, the methods of the invention are provided in combination with an anti-cancer agent to treat abnormal cell proliferation. In one embodiment, the anti-cancer agent is not an $A_{2a}$ receptor antagonist. Many of these drugs can be divided in to several categories: alkylating agents, antimetabolites, anthracyclines, plant alkaloids, topoisomerase inhibitors, monoclonal antibodies against tumor antigens, and other antitumour agents. Some agents don't directly interfere with DNA. These include the new tyrosine kinase inhibitor imatinib mesylate (Gleevec® or Glivec®), which directly targets a molecular abnormality in certain types of cancer (chronic myelogenous leukemia, gastrointestinal stromal tumors).

Alkylating agents are so named because of their ability to add alkyl groups to many electronegative groups under conditions present in cells. Cisplatin and carboplatin, as well as oxaliplatin are alkylating agents. Other agents are mechloethamine, cyclophosphamide, chlorambucil. They work by chemically modifying a cell's DNA.

Anti-metabolites masquerade as purine ((azathioprine, mercaptopurine)) or pyrimidine—which become the building blocks of DNA. They prevent these substances becoming incorporated in to DNA during the "S" phase (of the cell cycle), stopping normal development and division. They also affect RNA synthesis. Due to their efficiency, these drugs are the most widely used cytostatics.

Plant alkaloids and terpenoids are derived from plants and block cell division by preventing microtubule function. Microtubules are vital for cell division and without them it can not occur. The main examples are vinca alkaloids and taxanes. Vinca alkaloids bind to specific sites on tubulin, inhibiting the assembly of tubulin into microtubules (M phase of the cell cycle). They are derived from the Madagascar periwinkle, *Catharanthus roseus* (formerly known as *Vinca rosea*). The vinca alkaloids include: Vincristine; Vinblastine; Vinorelbine; and Vindesine. Podophyllotoxin is a plant-derived compound used to produce two other cytostatic drugs, etoposide and teniposide. They prevent the cell from entering the G1 phase (the start of DNA replication) and the replication of DNA (the S phase). The substance has been primarily obtained from the American Mayapple (*Podophyllum peltatum*). Recently it has been discovered that a rare Himalayan Mayapple (*Podophyllum hexandrum*) contains it in a much greater quantity, but as the plant is endangered, its supply is limited. Taxanes are derived from the Yew Tree. Paclitaxel (Taxol®) is derived from the bark of the Pacific Yew Tree (*Taxus brevifolia*). Researchers had found a much renewable source, where the precursors of Paclitaxel can be found in relatively high amounts in the leaves of the European Yew Tree (*Taxus baccata*), and that Paclitaxel, and Docetaxel (a semi-synthetic analogue of Paclitaxel) could be obtained by semi-synthetic conversion. Taxanes enhance stability of microtubules, preventing the separation of chromosomes during anaphase. Taxanes include: Paclitaxel and Docetaxel.

Topoisomerase inhibitors are another class of compounds. Topoisomerases are essential enzymes that maintain the topology of DNA Inhibition of type I or type II topoisomerases interferes with both transcription and replication of DNA by upsetting proper DNA supercoiling. Some type I topoisomerase inhibitors include camptothecins: irinotecan and topotecan. Examples of type II inhibitors include amsacrine, etoposide, etoposide phosphate, and teniposide. These are semisynthetic derivatives of epipodophyllotoxins, alkaloids naturally occurring in the root of American Mayapple (*Podophyllum peltatum*).

Antitumour antibiotics are another class of anti-cancer compounds. The most important immunosuppressant from this group is dactinomycin, which is used in kidney transplantations.

Several malignancies are also potentially treated with hormonal therapy. Steroids (often dexamethasone) can inhibit tumour growth or the associated edema (tissue swelling), and may cause regression of lymph node malignancies. Prostate cancer is often sensitive to finasteride, an agent that blocks the peripheral conversion of testosterone to dihydrotestosterone. Breast cancer cells often highly express the estrogen and/or progesterone receptor. Inhibiting the production (with aromatase inhibitors) or action (with tamoxifen) of these hormones can often be used as an adjunct to therapy. Gonadotropin-releasing hormone agonists (GnRH), such as goserelin possess a paradoxic negative feedback effect followed by inhibition of the release of FSH (follicle-stimulating hormone) and LH (luteinizing hormone), when given continuously.

General examples of anti-cancer agents also include: ifosamide, cisplatin, methotrexate, cytoxan, procarizine, etoposide, BCNU, vincristine, vinblastine, cyclophosphamide, gencitabine, 5-flurouracil, paclitaxel, and doxorubicin. Additional agents that are used to reduce cell proliferation include: AS-101 (Wyeth-Ayers" Labs.), bropirimine (Upjohn), gamma interferon (Genentech), GM-CSF (Genetics Institute), IL-2 (Cetus or Hoffman-LaRoche), human immune globulin (Cutter Biological), 20 IMREG (from Imreg of New Orleans, La.), SKF106528 (Genentech), TNF (Genentech), azathioprine, cyclophosphamide, chlorambucil, and methotrexate.

Passive Antibody Therapy

In one particular embodiment, a method of enhancing efficacy of passive antibody therapy is provided comprising administering an $A_{2a}$ Receptor antagonist in combination or alternation with one or more passive antibodies. The passive antibody therapy is not a vaccination. Unlike vaccines, which require time to induce protective immunity and depend on the host's ability to mount an immune response, passive antibody therapy can confer a level of protection regardless of the immune status of the host, however is enhanced by reduction of T cell tolerance using the $A_{2a}$ Receptor antagonist. Passive antibody therapy can have substantial advantages over antimicrobial agents and other measures for postexposure prophylaxis, including low toxicity and high specific activity. Specific antibodies are active against the major agents of bioterrorism, including anthrax, smallpox, botulinum toxin, tularemia, and plague.

This method can enhance the efficacy of antibody therapy for treatment of abnormal cell proliferative disorders such as cancer, or can enhance the efficacy of therapy in the treatment of infectious diseases. The antagonist can be administered in combination or alternation with antibodies such as rituximab, herceptin or erbitux, for example. In some embodiments, the antibody is an anticancer antibody. Monoclonal antibodies, including human and humanized monoclonal antibodies work by targeting tumour specific antigens, thus enhancing the host's immune response to tumour cells to which the agent attaches itself. Other antibody therapies include use of polyclonal antibodies and use of antibody fragments or regions. Examples are trastuzumab (Herceptin), cetuximab, and rituximab (Rituxan or Mabthera). Bevacizumab is a monoclonal antibody that does not directly attack tumor cells but instead blocks the formation of new tumor vessels. In some embodiments, the antibody is a humanized antibody. In other embodiments, the antibody is a human antibody. In yet further embodiments, the antibody is an antibody fragment. Antibody fragments include, for example, scFv, Fab, F(ab)'$_2$, Fc, heavy chain, light chain or any combination or fusion thereof. Additional examples of anti-cancer antibodies are Alemtuzumab (Campath) (BTG, West Conshohocken, Pa.) targeting CD52, for chronic lymphocytic and chronic myelogenous leukemia and multiple sclerosis; Daclizumab (Zenapax) (Protein Design Labs, Fremont, Calif.), targeting the IL-2 receptor, CD25, for transplant rejection, uveitis, multiple sclerosis, leukemia, psoriasis, diabetes mellitus, type 1, asthma and ulcerative colitis; Rituximab (Rituxan) (IDEC Pharmaceuticals, San Diego, Calif.), targeting CD20, for n lymphomas, rheumatoid arthritis, thrombocytopenic purpura; Trastuzumab (Herceptin)(Genentech), targeting p185$^{neu}$ for breast, lung, pancreatic cancers; Gemtuzumab (Mylotarg) (Wyeth/AHP, Collegeville, Pa.) targeting CD33/cali-cheamicin, for leukemia; Ibritumomab (Zevalin) (IDEC Pharmaceuticals) targeting CD20/yttrium 90 for lymphomas; Edrecolomab (Panorex) (GlaxoSmithKline, London, England) targeting epithelial cell adhesion molecule for colorectal cancer. Additional anticancer antibodies are listed in the table below:

TABLE

Selected Anticancer Antibodies in Clinical Trials

| Drug Name | Source | Features | Investigational Indications |
|---|---|---|---|
| Tositumomab (Bexxar) | Corixa, Seattle, WA | Anti-CD20 murine monoclonal antibody with iodine 131 conjugation | Non-Hodgkin lymphoma |
| CeaVac | Titan Pharmaceuticals, South San Francisco, CA | Anti-CEA murine monoclonal antibody; anticancer immunologic vaccine | Cancer: colorectal, non-small cell of the lung, breast, liver |
| Epratuzumab (LymphoCide) | Immunomedics, Morris Plains, NJ | Chimeric monoclonal antibody; anticancer immunologic; immunosuppressant | Non-Hodgkin lymphoma |
| Mitumomab | ImClone Systems, New York, NY | Murine monoclonal antibody; anticancer immunologic | Small cell cancer of the lung; melanoma |

TABLE-continued

Selected Anticancer Antibodies in Clinical Trials

| Drug Name | Source | Features | Investigational Indications |
|---|---|---|---|
| Bevacizumab (Avastin) | Genentech, South San Francisco, CA | Anti-VEGF humanized monoclonal antibody; anticancer immunologic; antidiabetic; ophthalmologic | Cancer: colorectal, breast, non-small cell of the lung; diabetic retinopathy |
| Cetuximab (C-225; Erbitux) | ImClone Systems | Anti-EGFR chimeric monoclonal antibody; anticancer immunologic | Cancer: head and neck, non-small cell of the lung, colorectal, breast, pancreas, prostate |
| Edrecolomab | Johnson & Johnson, New Brunswick, NJ | Murine monoclonal antibody; anticancer immunologic | Cancer: colorectal and breast |
| Lintuzumab (Zamyl) | Protein Design Labs, Fremont, CA | Chimeric monoclonal antibody; anticancer immunologic | Acute myelogenous leukemia; myelodysplastic syndrome |
| MDX-210 | Medarex, Princeton, NJ; Immuno-Designed Molecules, Havana, Cuba | Bispecific chimeric monoclonal antibody; anti-HER-2/neu-anti-Fc gamma RI; anticancer immunologic | Cancer: ovarian, prostate, colorectal, renal, breast |
| IGN-101 | Igeneon, Vienna, Austria | Murine monoclonal antibody; anticancer immunologic | Cancer: non-small cell of the lung, liver, colorectal, esophageal, stomach |
| MDX-010 | Medarex | Humanized anti-HER-2 monoclonal antibody; anticancer immunologic; immunostimulant | Cancer: prostate, melanoma; infection, general |
| MAb, AME | Applied Molecular Evolution, San Diego, CA | Chimeric monoclonal antibody; anticancer immunologic; imaging agent; antiarthritic immunologic; ophthalmologic; cardiovascular | Cancer: sarcoma, colorectal; rheumatoid arthritis; psoriatic arthritis |
| ABX-EGF | Abgenix, Fremont, CA | Monoclonal antibody, human; anticancer immunologic | Cancer: renal, non-small cell of the lung, colorectal, prostate |
| EMD 72 000 | Merck KGaA, Darmstadt, Germany | Chimeric monoclonal antibody; anticancer immunologic | Cancer: stomach, cervical, non-small cell of the lung, head and neck, ovarian |
| Apolizumab | Protein Design Labs | Chimeric monoclonal antibody; anticancer immunologic | Non-Hodgkin lymphoma; chronic lymphocytic leukemia |
| Labetuzumab | Immunomedics | Chimeric monoclonal antibody; immunoconjugate; anticancer immunologic | Cancer: colorectal, breast, small cell of the lung, ovarian, pancreas, thyroid, liver |
| ior-t1 | Center of Molecular Immunology, Havana, Cuba | Murine monoclonal antibody; anticancer immunologic; antipsoriatic; antiarthritic immunologic | T-cell lymphoma; psoriasis; rheumatoid arthritis |
| MDX-220 | Immuno-Designed Molecules | Chimeric monoclonal antibody; anticancer immunologic | Cancer: prostate, colorectal |
| MRA | Chugai Pharmaceutical, Tokyo, Japan | Chimeric monoclonal antibody; antiarthritic immunologic; anticancer immunologic; GI inflammatory and bowel disorders | Rheumatoid arthritis; cancer, myeloma; Crohn disease; Castleman disease |
| H-11 scFv | Viventia Biotech, Toronto, Canada | Humanized monoclonal antibody; anticancer immunologic | Non-Hodgkin lymphoma, melanoma |
| Oregovomab | AltaRex, Waltham, MA | Monoclonal antibody, murine; anticancer immunologic; immunoconjugate | Cancer: ovarian |
| huJ591 MAb, BZL | Millennium Pharmaceuticals, Cambridge, MA; BZL Biologics, Framingham, MA | Chimeric monoclonal antibody; anticancer immunologic | Cancer: prostate and general |

TABLE-continued

Selected Anticancer Antibodies in Clinical Trials

| Drug Name | Source | Features | Investigational Indications |
|---|---|---|---|
| Visilizumab | Protein Design Labs | Chimeric monoclonal antibody; immunosuppressant; anticancer immunologic; GI inflammatory and bowel disorders | Transplant rejection, bone marrow; cancer, T-cell lymphoma; ulcerative colitis; myelodysplastic syndrome; systemic lupus erythematosus |
| TriGem | Titan Pharmaceuticals | Murine monoclonal antibody; anticancer immunologic | Cancer: melanoma, small cell of the lung, brain |
| TriAb | Titan Pharmaceuticals | Murine monoclonal antibody; anticancer immunologic | Cancer: breast, non-small cell of the lung, colorectal |
| R3 | Center of Molecular Immunology | Chimeric monoclonal antibody; anticancer immunologic; imaging agent; immunoconjugate | Cancer: head and neck; diagnosis of cancer |
| MT-201 | Micromet, Munich, Germany | Humanized monoclonal antibody; anticancer immunologic | Cancer: prostate, colorectal, stomach, non-small cell of the lung |
| G-250, unconjugated | Johnson & Johnson | Chimeric monoclonal antibody; anticancer immunologic | Cancer: renal |
| ACA-125 | CellControl Biomedical, Martinsried, Germany | Monoclonal antibody; anticancer immunologic | Cancer: ovarian |
| Onyvax-105 | Onyvax, London, England | Monoclonal antibody; anticancer immunologic | Cancer: colorectal; sarcoma, general |
| CDP-860 | Celltech, Slough, England | Humanized monoclonal antibody; anticancer immunologic; cardiovascular | Cancer: general; restenosis |
| BrevaRex MAb | AltaRex | Murine monoclonal antibody; anticancer immunologic | Cancer: myeloma, breast |
| AR54 | AltaRex | Murine monoclonal antibody; anticancer immunologic | Cancer: ovarian |
| IMC-1C11 | ImClone Systems | Chimeric monoclonal antibody; anticancer immunologic | Cancer: colorectal |
| GlioMAb-H | Viventia Biotech | Humanized monoclonal antibody; imaging agent; anticancer immunologic | Diagnosis of cancer; cancer, brain |
| ING-1 | Xoma, Berkeley, CA | Chimeric monoclonal antibody; anticancer immunologic | Cancer: breast, lung (general), ovarian, prostate |
| Anti-LCG MAbs | eXegenics, Dallas, TX | Monoclonal antibody; anticancer; imaging agent | Cancer: lung, general; diagnosis of cancer |
| MT-103 | Micromet | Murine monoclonal antibody; anticancer immunologic | B-cell lymphoma, non-Hodgkin lymphoma, chronic myelogenous leukemia, acute myelogenous leukemia |
| KSB-303 | KS Biomedix, Guildford, England | Chimeric monoclonal antibody; anticancer immunologic | Diagnosis of cancer; cancer, colorectal |
| Therex | Antisoma, London, England | Chimeric monoclonal antibody; anticancer immunologic | Cancer: breast |
| KW-2871 | Kyowa Hakko, Tokyo, Japan | Chimeric monoclonal antibody; anticancer immunologic | Melanoma |
| Anti-HM1.24 | Chugai | Chimeric monoclonal antibody; anticancer immunologic | Myeloma |
| Anti-PTHrP | Chugai | Chimeric monoclonal antibody; anticancer immunologic; osteoporosis | Hypercalcemia of malignancy; cancer, bone |
| 2C4 antibody | Genentech | Chimeric monoclonal antibody; anticancer immunologic | Cancer: breast |

TABLE-continued

Selected Anticancer Antibodies in Clinical Trials

| Drug Name | Source | Features | Investigational Indications |
|---|---|---|---|
| SGN-30 | Seattle Genetics, Seattle, WA | Monoclonal antibody; anticancer immunologic; multiple sclerosis treatment; immunosuppressant; immunoconjugate | Hodgkin lymphoma |
| TRAIL-RI MAb, CAT | Cambridge Antibody Technology, Cambridge, England | Humanized monoclonal antibody; anticancer immunologic | Cancer: general |
| Prostate cancer antibody | Biovation, Aberdeen, Scotland | Monoclonal antibody; anticancer | Cancer: prostate |
| H22xKi-4 | Medarex | Chimeric monoclonal antibody; anticancer immunologic | Hodgkin lymphoma |
| ABX-MA1 | Abgenix | Humanized monoclonal antibody; anticancer immunologic | Melanoma |
| Imuteran | Nonindustrial source | Monoclonal antibody; anticancer immunologic | Cancer: breast, ovarian |
| Monopharm-C | Viventia Biotech | Monoclonal antibody; anticancer immunologic; imaging agent | Cancer: colorectal; diagnosis of cancer |

CEA, carcinoembryonic antigen;
EGFR, epidermal growth factor receptor;
GI, gastrointestinal;
VEGF, vascular endothelial growth factor.

In some embodiments, the antibody is an antibody to an infectious disease. Diseases to which antibodies have been used clinically include Anthrax (cutaneous, gastrointestinal, and inhalational) by passive administration of polyclonal antibodies raised against recombinant protective antigen (PA), lethal factor (LF) and edema factor (EF); Botulinum Toxins by administration of antibodies against the most common causes of human botulism, toxin types A, B, E, a heptavalent equine serum, and a human botulinum immune globulin derived from volunteers vaccinated with pentavalent botulinum toxoid (ABCDE) vaccine; Brucellosis using a antibodies specific for the O polysaccharide of *B. abortus*, to the M epitope of *Brucella* spp. or panels of murine MAbs; Q Fever using a antibodies against *C. burnetii* infection; Plague using passive antibody administration against lethal *Y. pestis* infection; Smallpox using neutralizing and protective antibodies to vaccinia virus; Tularemia using passive antibodies to *F. tularensis*; Viral Encephalitides using antibodies to Eastern equine encephalomyelitis virus (EEEV), Venezuelan equine encephalomyelitis virus (VEEV), or Western equine encephalomyelitis virus (WEEV); Viral Hemorrhagic Fevers using antibodies to Ebola, Argentine and Lassa hemorrhagic fevers. In certain embodiments, the antibody is against a respiratory syncytial virus (RSV). Such antibodies include Synagis® (Medimmune) and Numax® (Medimmune). Additional antibodies useful for modulating immune functions to stimulate a desired immune response include HGS-ETR1 and HGS-ETR2 (Medimmune).

Antigens of Pathogens and Tumor Cells

In one embodiment of the invention, the method provides an enhanced and prolonged immune response to an antigen. An antigen is generally any compound, composition, or agent, as well as all related antigenic epitopes, capable of being the target of inducing a specific immune response, such as stimulate the production of antibodies or a T-cell response in a subject, including compositions that are injected or absorbed into a subject. In some embodiments, the host is infected with a virus or bacteria that has an antigen prior to the administration of the antagonist. For example, the host can be infected with an HIV virus. In other embodiments, the host is infected with a flavivirus or pestivirus, or other member of the flaviviridae family such as hepatitis C. Pestiviruses and flaviviruses belong to the flaviviridae family of viruses along with hepacivirus (hepatitis C virus). The pestivirus genus includes bovine viral diarrhea virus (BVDV), classical swine fever virus (CSFV, also called hog cholera virus) and border disease virus (BDV) of sheep (Moennig, V. et al. *Adv. Vir. Res.* 1992, 41, 53-98). Pestivirus infections of domesticated livestock (cattle, pigs and sheep) cause significant economic losses worldwide. BVDV causes mucosal disease in cattle and is of significant economic importance to the livestock industry (Meyers, G. and Thiel, H.-J., *Advances in Virus Research,* 1996, 47, 53-118; Moennig V., et al, *Adv. Vir. Res.* 1992, 41, 53-98). In certain embodiments, the host is infected with a hepatitis B virus. In other embodiments, the host is infected with hepatitis D (also known as hepatitis delta). In certain embodiments, the host is infected with a member of the herpes family, such as Herpes simplex virus, Cytomegalovirus, and Epstein-Barr virus (EBV).

Antigens can include: live, heat killed, or chemically attenuated viruses, bacteria, mycoplasmas, fungi, and protozoa, or fragments, extracts, subunits, metabolites and recombinant constructs of these or fragments, subunits, metabolites and recombinant constructs of mammalian proteins and glycoproteins; nucleic acids; combinations of these; or whole mammalian cells.

Antigens can be from pathogenic and non-pathogenic organisms, viruses, and fungi. Antigens can include proteins, peptides, antigens and vaccines from smallpox, yellow fever, distemper, cholera, fowl pox, scarlet fever, diphtheria, tetanus, whooping cough, influenza, rabies, mumps, measles, foot and mouth disease, and poliomyelitis.

The antigen can be a protein or peptide. In certain embodiments, the antigen is exogenous. The antigen can, for example, be a viral or bacterial protein or peptide, or antigenic fragment thereof. In certain instances, the antigen is from a "subunit" vaccine, composed of viral or bacterial antigenic determinants, generally in which viral or bacterial antigens made are free of nucleic acid by chemical extraction and containing only minimal amounts of non-viral or non-bacterial antigens derived from the culture medium. In other instances, the antigen is not based on a subunit vaccine.

In certain embodiments, the antigen is a whole cell, derived from a virus, bacteria or mammal. In certain embodiments, the antigen is a "killed component" of a vaccine. In some embodiments of the invention, the antigen is derived from a human or animal pathogen. The pathogen is optionally a virus, bacterium, fungus, or a protozoan. In this instance, the antigen is prepared from a viral or bacterial cell that has been irradiated or otherwise inactivated to avoid replication. In one embodiment, the antigen is a protein produced by the pathogen, or a fragment and/or variant of a protein produced by the pathogen. In other embodiments, the antigen is a mammalian protein or peptide. In certain embodiment, the antigen is a whole mammalian cell and is not an isolated mammalian protein or peptide, or fragment thereof.

In some embodiments, the antigen is a whole cell. In some embodiments, the antigen is a whole mammalian cell, which can be genetically modified. In certain embodiments, the cell is a whole mammalian tumor cell that has been modified to express a colony stimulating factor. In other embodiments, the antigen is a stromal antigen-presenting cell capable of antigen presentation. In other embodiments, the antigen comprises a dendritic cell or a dendritic cell preparation. The antigen can include antigens and dendritic antigen-presenting cells (APCs). Target disorders for dendritic cell therapy include disseminated single tumor cells (micrometastases) or metastases of epithelial tumors including from breast cancer, ovarian cancer, prostate cancer, colon cancer, glioblastomas and myelomas.

In some embodiments, the antigen may be derived from Human Immunodeficiency virus (such as gp120, gp 160, gp41, gag antigens such as p24gag and p55gag, as well as proteins derived from the pol, env, tat, vif, rev, nef, vpr, vpu and LTR regions of HIV), Feline Immunodeficiency virus, or human or animal herpes viruses. In one embodiment, the antigen is derived from herpes simplex virus (HSV) types 1 and 2 (such as gD, gB, gH, Immediate Early protein such as ICP27), from cytomegalovirus (such as gB and gH), from Epstein-Barr virus or from Varicella Zoster Virus (such as gpI, II or III). (See, e.g., Chee et al. (1990) Cytomegaloviruses (J. K. McDougall, ed., Springer Verlag, pp. 125-169; McGeoch et al. (1988) J. Gen. Virol. 69: 1531-1574; U.S. Pat. No. 5,171,568; Baer et al. (1984) Nature 310: 207-211; and Davison et al. (1986) J. Gen. Virol. 67: 1759-1816.)

In another embodiment, the antigen is derived from a hepatitis virus such as hepatitis B virus (for example, Hepatitis B Surface antigen), hepatitis A virus, hepatitis C virus, delta hepatitis virus, hepatitis E virus, or hepatitis G virus. See, e.g., WO 89/04669; WO 90/11089; and WO 90/14436. The hepatitis antigen can be a surface, core, or other associated antigen. The HCV genome encodes several viral proteins, including E1 and E2. See, e.g., Houghton et al., Hepatology 14: 381-388(1991).

An antigen that is a viral antigen is optionally derived from a virus from any one of the families Picornaviridae (e.g., polioviruses, rhinoviruses, etc.); Caliciviridae; Togaviridae (e.g., rubella virus, dengue virus, etc.); Flaviviridae; Coronaviridae; Reoviridae (e.g., rotavirus, etc.); Birnaviridae; Rhabodoviridae (e.g., rabies virus, etc.); Orthomyxoviridae (e.g., influenza virus types A, B and C, etc.); Filoviridae; Paramyxoviridae (e.g., mumps virus, measles virus, respiratory syncytial virus, parainfluenza virus, etc.); Bunyaviridae; Arenaviridae; Retroviradae (e.g., HTLV-I; HTLV-11; HIV-1; HIVI11b; HIVSF2; HTVLAV; HIVLAI; HIVMN; HIV-1CM235; HIV-2; simian immunodeficiency virus (SIV)); Papillomavirus, the tick-borne encephalitis viruses; and the like. See, e.g. Virology, 3rd Edition (W. K. Joklik ed. 1988); Fundamental Virology, 3rd Edition (B. N. Fields, D. M. Knipe, and P. M. Howley, Eds. 1996), for a description of these and other viruses. In one embodiment, the antigen is Flu-HA (Morgan et al., J. Immunol. 160:643 (1998)).

In one embodiment, the antigen comprises a (Myco) bacterial or viral protein or an immunogenic part, derivative and/or analogue thereof. In one aspect of the invention, the antigen comprises a *Mycobacterium* protein or an immunogenic part, derivative and/or analogue thereof. In one embodiment, the antigen comprises hsp65 369 412 (Ottenhof et al., 1991; Charo et al., 2001). In another embodiment, the antigen comprises a human papillomavirus (HPV) protein or an immunogenic part, derivative and/or analogue thereof. An immunogenic part, derivative and/or analogue of a protein comprises the same immunogenic capacity in kind not necessarily in amount as said protein itself. A derivative of such a protein can be obtained by conservative amino acid substitution. In one embodiment, the antigen is a killed whole pneumococci, lysate of pneumococci or isolated and purified PspA, or immunogenic fragments thereof (see U.S. Pat. No. 6,042,838). In one embodiment, the antigen is a 314 amino acid truncate (amino acids 1-314) of the mature PspA molecule. This region of the PspA molecule contains most, if not all, of the protective epitopes of PspA.

In some embodiments, the antigen is derived from bacterial pathogens such as *Mycobacterium, Bacillus, Yersinia, Salmonella, Neisseria, Borrelia* (for example, OspA or OspB or derivatives thereof), *Chlamydia*, or *Bordetella* (for example, P.69, PT and FHA), or derived from parasites such as plasmodium or *Toxoplasma*. In one embodiment, the antigen is derived from the *Mycobacterium tuberculosis* (e.g. ESAT-6, 85A, 85B, 72F), *Bacillus anthracis* (e.g. PA), or *Yersinia pestis* (e.g. F1, V). In addition, antigens suitable for use in the present invention can be obtained or derived from known causative agents responsible for diseases including, but not limited to, Diptheria, Pertussis, Tetanus, Tuberculosis, Bacterial or Fungal Pneumonia, Otitis Media, Gonorrhea, Cholera, Typhoid, Meningitis, Mononucleosis, Plague, Shigellosis or Salmonellosis, Legionaire's Disease, Lyme Disease, Leprosy, Malaria, Hookworm, Onchocerciasis, Schistosomiasis, Trypamasomialsis, Lesmaniasis, Giardia, Amoebiasis, Filariasis, Borelia, and Trichinosis. Still further antigens can be obtained or derived from unconventional pathogens such as the causative agents of kuru, Creutzfeldt-Jakob disease (CJD), scrapie, transmissible mink encephalopathy, and chronic wasting diseases, or from proteinaceous infectious particles such as prions that are associated with mad cow disease.

A large number of tumor-associated antigens that are recognized by T cells have been identified (Renkvist et al., Cancer Immunol Innumother 50:3-15 (2001)). These tumor-associated antigens may be differentiation antigens (e.g., PSMA, Tyrosinase, gp100), tissue-specific antigens (e.g. PAP, PSA), developmental antigens, tumor-associated viral antigens (e.g. HPV 16 E7), cancer-testis antigens (e.g. MAGE, BAGE, NY-ESO-1), embryonic antigens (e.g. CEA, alpha-fetoprotein), oncoprotein antigens (e.g. Ras, p53), over-expressed protein antigens (e.g. ErbB2 (Her2/Neu), MUC1), or mutated protein antigens.

Tumor-associated antigens that may be useful in the methods of the invention include, but are not limited to, 707-AP, Annexin II, AFP, ART-4, BAGE, β-catenin/m, BCL-2, bcr-abl, bcr-abl p190, bcr-abl p210, BRCA-1, BRCA-2, CAMEL, CAP-1, CASP-8, CDC27/m, CDK-4/m, CEA (Huang et al., *Exper Rev. Vaccines* (2002)1:49-63), CT9, CT10, Cyp-B, Dek-cain, DAM-6 (MAGE-B2), DAM-10 (MAGE-B1), EphA2 (Zantek et al., *Cell Growth Differ.* (1999) 10:629-38; Carles-Kinch et al., *Cancer Res.* (2002) 62:2840-7), ELF2M, ETV6-AML1, G250, GAGE-1, GAGE-2, GAGE-3, GAGE-4, GAGE-5, GAGE-6, GAGE-7B, GAGE-8, GnT-V, gp100, HAGE, HER2/neu, HLA-A*0201-R170I, HPV-E7, HSP70-2M, HST-2, hTERT, hTRT, iCE, inhibitors of apoptosis (e.g. survivin), KIAA0205, K-ras, LAGE, LAGE-1, LDLR/FUT, MAGE-1, MAGE-2, MAGE-3, MAGE-6, MAGE-A1, MAGE-A2, MAGE-A3, MAGE-A4, MAGE-A6, MAGE-A10, MAGE-A12, MAGE-B5, MAGE-B6, MAGE-C2, MAGE-C3, MAGE-D, MART-1, MART-1/Melan-A, MC1R, MDM-2, mesothelin, Myosin/m, MUC1, MUC2, MUM-1, MUM-2, MUM-3, neo-polyA polymerase, NA88-A, NY-ESO-1, NY-ESO-1a (CAG-3), PAGE-4, PAP, Proteinase 3 (Molldrem et al., *Blood* (1996) 88:2450-7; Molldrem et al., *Blood* (1997) 90:2529-34), P15, p190, Pm1/RARα, PRAME, PSA, PSM, PSMA, RAGE, RAS, RCAS1, RU1, RU2, SAGE, SART-1, SART-2, SART-3, SP 17, SPAS-1, TEL/AML 1, TPI/m, Tyrosinase, TARP, TRP-1 (gp75), TRP-2, TRP-2/INT2, WT-1, and alternatively translated NY-ESO-ORF2 and CAMEL proteins.

In some embodiments, the antigen that is not identical to a tumor-associated antigen, but rather is derived from a tumor-associated antigen. For instance, the antigen may comprise a fragment of a tumor-associated antigen, a variant of a tumor-associated antigen, or a fragment of a variant of a tumor-associated antigen. In some cases, an antigen, such as a tumor antigen, is capable of inducing a more significant immune response when the sequence differs from that endogenous to the host. In some embodiments, the variant of a tumor-associated antigen, or a fragment of a variant of a tumor-associated antigen, differs from that of the tumor-associated antigen, or its corresponding fragment, by one or more amino acids. The antigen derived from a tumor-associated antigen can comprise at least one epitope sequence capable of inducing an immune response upon administration.

Alternatively, the antigen can be an autoimmune disease-specific antigen. In a T cell mediated autoimmune disease, a T cell response to self antigens results in the autoimmune disease. The type of antigen for use in treating an autoimmune disease with the vaccines of the present invention might target the specific T cells responsible for the autoimmune response. For example, the antigen may be part of a T cell receptor, the idiotype, specific to those T cells causing an autoimmune response, wherein the antigen incorporated into a vaccine of the invention would elicit an immune response specific to those T cells causing the autoimmune response. Eliminating those T cells would be the therapeutic mechanism to alleviating the autoimmune disease. Another possibility would be to incorporate an antigen that will result in an immune response targeting the antibodies that are generated to self antigens in an autoimmune disease or targeting the specific B cell clones that secrete the antibodies. For example, an idiotype antigen may be incorporated into the *Listeria* that will result in an anti-idiotype immune response to such B cells and/or the antibodies reacting with self antigens in an autoimmune disease.

In still other embodiments, the antigen is obtained or derived from a biological agent involved in the onset or progression of neurodegenerative diseases (such as Alzheimer's disease), metabolic diseases (such as Type I diabetes), and drug addictions (such as nicotine addiction). Alternatively, the method can be used for pain management and the antigen is a pain receptor or other agent involved in the transmission of pain signals.

Diseases and Disorders of Abnormal Cell Proliferation

In certain embodiments, the present invention can be used to treat, prevent, manage and slow the spread of cancer as well as other abnormal cell proliferation-associated diseases in a host.

Throughout the application, a host is any multi-cellular vertebrate organism including specifically both human and non-human mammals. In one embodiment, the "host" is a human. The terms "subject" and "patient" are also included in the term "host".

In certain embodiments, the present invention provides methods to treat carcinomas, include tumors arising from epithelial tissue, such as glands, breast, skin, and linings of the urogenital, digestive, and respiratory systems. Lung, cancer and prostate cancers can be treated or prevented. Breast cancers that can be treated or prevented include both invasive (e.g., infiltrating ductal carcinoma, infiltrating lobular carcinoma infiltrating ductal & lobular carcinoma, medullary carcinoma, mucinous (colloid) carcinoma, comedocarcinoma, paget's disease, papillary carcinoma, tubular carcinoma, adenocarcinoma (NOS) and carcinoma (NOS)) and non-invasive carcinomas (e.g., intraductal carcinoma, lobular carcinoma in situ (LCIS), intraductal & LCIS, papillary carcinoma, comedocarcinoma). The present invention can also be used to treat or prevent metastatic breast cancer. Non-limiting examples of metastatic breast cancer include bone, lung and liver cancer.

Prostate cancers that can be treated or prevented with the methods described herein include localized, regional and metastatic prostate cancer. Localized prostate cancers include A1-A2, T1a-T1b, T1c, B0-B2 or $T_{2a}$-T2c. C1-C2 or T3a-N0, prostate cancers extending beyond the prostate but without lymph node involvement, are also contemplated. Regional prostate cancers include D1 or N1-M0, while metastatic prostate cancers include D2 or M1. Metastatic prostate cancers include bone and brain cancers.

In certain embodiments, methods are provided to treat or prevent abnormal cell proliferation using $A_{2a}$ receptor antagonists in combination or alternation with a cell based vaccine. In certain of these embodiments, the cell based vaccine is based on cells that match the tumor to be prevented. For example, if a host is suffering from, or at risk of suffering from, a prostate cancer, the cell based vaccine will be based on a prostate cancer tumor cell. In these instances, the cell is typically irradiated or otherwise prevented from replicating. In particular embodiments, the cell is genetically modified to secrete a colony stimulating factor.

Other cancers that can be treated or prevented with the present invention include, but are not limited to, cancers of the cancers include those of the bowel, bladder, brain, cervix, colon, rectum, esophagus, eye, head and neck, liver, kidney, larynx, lung, skin, ovary, pancreas, pituitary gland, stomach, testicles, thymus, thyroid, uterus, and vagina as well as adrenocortical cancer, carcinoid tumors, endocrine cancers, endometrial cancer, gastric cancer, gestational trophoblastic tumors, islet cell cancer, and mesothelioma.

Lymphomas that can be treated or prevented with the invention include tumors arising from the lymph or spleen, which can cause excessive production of lymphocytes, including both Hodgkin's disease and Non-Non-Hodgkin's lymphoma. The term "Hodgkin's Disease" is intended to include diseases classified as such by the REAL and World Health Organization (WHO) classifications known to those of skill in the art, including classical Hodgkin's disease (i.e., nodular sclerosis, mixed cellularity, lymphocyte depletion or lymphocyte rich) or lymphocyte predominance Hodgkin's disease. The term "Non-Hodgkin's lymphoma" is used to refer 30 lymphomas classified by WHO (Harris N L et al. (2000) Lymphoma classification-from controversy to consensus: the REAL and WHO Classification of lymphoid neoplasms. *Ann Oncol.* 11(suppl 1):S3-S10), including but not limited to:

B-cell non-Hodgkin's lymphomas such as small lymphocytic lymphoma (SLL/CLL), mantle cell lymphoma (MCL), follicular lymphoma marginal zone lymphoma (MZL), extranodal (MALT lymphoma), nodal (Monocytoid B-cell lymphoma), splenic, diffuse large cell lymphoma, burkitt's lymphoma and lymphoblastic lymphoma.

T-cell non-Hodgkin's lymphoma's such as lymphoblastic lymphomas, peripheral T-cell lymphoma. Hepatosplenic gamma-delta T-cell lymphoma, subcutaneous panniculitis-like lymphoma, angioimmunoblastic T-cell lymphoma (AILD), extranodal NK/T cell lymphoma, nasal type, intestinal T-cell lymphoma (+/− enteropathy associated) (EATL), adult T-cell leukemia/lymphoma (HTLV-1 associated), mycosis fungoides/Sezary syndrome, anaplastic large cell lymphoma (ALCL), including both primary cuteous and primary systemic types.

Leukemias that can be treated or prevented with the present invention include but are not limited to myeloid and lymphocytic (sometimes referred to as B or T cell leukemias) or myeloid leukemias, both chronic and acute. The myeloid leukemias include chronic myeloid leukemia (CML) and acute myeloid leukemia (AML) (i.e., acute nonlymphocytic leukemia (ANLL)). The lymphocytic leukemias include acute lymphocytic leukemia (ALL), chronic lymphocytic leukemia (CLL) (i.e., chronic granulocytic leukemia) and hairy cell leukemia (HCL).

Sarcomas that can be treated or prevented with the present invention include both bone and soft-tissue sarcomas of the muscles, tendons, fibrous tissues, fat, blood vessels nerves, and synovial tissues. Non-limiting examples include fibrosacromas, rhabdomyosarcomas, liposarcomas, synovial sarcomas, angiosarcomas, neurofibrosarcomas, gastrointestinal stroma tumors, Kaposi's sarcoma, Ewing's sarcoma, alveolar soft-part sarcoma, angiosarcoma, dermatofibrosarcoma protuberans, epithelioid sarcoma, extraskeletal chondrosarcoma, extraskeletal osteosarcoma, fibrosarcoma, leiomyosarcoma, liposarcoma, malignant fibrous histiocytoma, malignant hemangiopericytoma, malignant mesenchymoma, malignant schwannoma, malignant peripheral nerve sheath tumor, parosteal osteosarcoma, peripheral neuroectodermal tumors, rhabdomyosarcoma, synovial sarcoma, and sarcoma, NOS.

Diseases of abnormal cell proliferation other than cancer can be treated or prevented with the present invention. Diseases association with the abnormal proliferation of vascular smooth muscle cells include, as a non-limiting example, benign tumors. Non-limiting examples of benign tumors include benign bone, brain and liver tumors.

Other diseases associated with abnormal cell proliferation include, for example, atherosclerosis and restenosis. Diseases associated with abnormal proliferation of over-proliferation and accumulation of tissue mast cells are also included, such as cutaneous mastocytosis (CM) and Urticaria pigmentosa. Diseases associated with abnormal proliferation of xesangial cell proliferation are also contemplated, including but not limited to IgA nephropathy, membranoproliferative glomerulonephritis (GN), lupus nephritis and diabetic nephropathy.

Psoriasis can be treated or prevented by the present invention, including but not limited to, plaque psoriasis, guttate psoriasis, inverse psoriasis, seborrheic psoriasis, nail psoriasis, generalized erythrodermic psoriasis (also called psoriatic exfoliative erythroderm), pustular psoriasis, and Von Zumbusch psoriasis.

The present invention can also be used to treat or prevent lymphangiomyomatosis (LAM), as well as other diseases associated with abnormal cell proliferation known to those skilled in the art.

Adenosine $A_{2a}$ Receptor Agonists for Inducing Long Term T Cell Tolerance

Methods of Inducing Tolerance

It has been discovered that $A_{2a}$ receptors are responsible for induction of long term T cell tolerance. These receptors can induce tolerance both by promoting T cell anergy, under which T cells fail to respond to an antigen upon re-challenge even under normally activating conditions, and by inducing regulatory T cells, which are responsible for maintained tolerance.

Many drugs have been shown to inhibit T cells responses, for example Cyclosporine A. However, such agents require continuous administration. That is, when the drug is stopped the T cells can become activated again. It has now been found that $A_{2a}$ receptor agonists can stimulate and maintain T cell tolerance. As such, a finite treatment with an $A_{2a}$ receptor agonists will lead to sustained tolerance thus abrogating the need for chronic immunosuppression. In particular, it has been found that $A_{2a}$ receptor agonists can reduce the need for continued immunosuppression in preventing or treating autoimmune diseases or disorders, for example in preventing transplant rejection or Graft versus Host Disease.

In one embodiment, a method of inducing immune tolerance in a host in need thereof is provided comprising administering an $A_{2a}$ receptor agonist to the host, wherein the tolerance is induced for at least one month, at least 2 months, at least 3 months, at least 4 months, at least 5 months, at least 6 months, at least 7 months, at least 8 months, at least 9 months, or longer, such as at least one year.

In one embodiment, the $A_{2a}$ agonist is administered in combination with an immunosuppressive agent other than an $A_{2a}$ agonist. In some embodiments, the $A_{2a}$ agonist is administered in combination with an immunosuppressive agent and subsequently, the $A_{2a}$ agonist is administered in the absence of the immunosuppressive agent.

In a specific embodiment, the host is in need of immunosuppressive therapy. In one embodiment, the host is being treated with an immunosuppressive therapy. In certain embodiments, administration of the $A_{2a}$ receptor agonist reduces the amount of immunosuppressive therapy administered to the host. In some embodiments, the amount of immunosuppressive therapy is reduced by a factor of 2, or 3, or 4 or 5 or 6, or 7, or 8 or 9 or 10. In certain other embodiments, the host is able to be subject to a different immunosuppressive regimen with a reduced toxicity. In certain embodiments, the immunosuppressive agent can be administered for less than one year. In one embodiment, the immunosuppressive agent is administered for from 2 weeks to one year. In one embodiments, the immunosuppressive agent is administered for one month, 2 months, 3 months, 4 months, 5 months, 6 months, 7 months, 8 months, 9 months, 10 months, 11 months or 12 months or less.

In certain embodiments, administration of the $A_{2a}$ agonist reduces immune responses against an antigen. In some embodiments, the antigen is an exogenous protein. In other embodiments, the antigen is a protein native to the host. In certain embodiments, the antigen is a cell surface antigen.

In one particular embodiment, the host is suffering from an autoimmune disease. In another embodiment, the host is at risk for an autoimmune disorder. In another embodiment, the host is a recipient of a transplanted tissue or organ. In a particular embodiment, the host is at risk of organ rejection.

In certain embodiments, the $A_{2a}$ agonist is administered in combination or alternation with a costimulatory molecule such as B7-H4 or fragments or variants thereof.

In certain embodiments, T cell tolerance is induced for at least one month, or at least three months, or at least six months.

In certain embodiments, the methods further comprise administering an antigen to the host in combination or alternation with the agonist. The antigen can be a protein or peptide derived from the host, or can be an exogenous protein or peptide. The antigen can also be a cell derived from the host or an exogenous cell. The administration of the agonist in combination with the antigen can cause T cell tolerance to the antigen.

In certain embodiments, the agonist is administered less than once a week. In certain embodiments, the agonist is administered once a month. In certain other embodiments, an immunosuppressive agent is not administered to the host receiving the agonist.

In one subembodiment, the agonist is administered every day, or less, such as every two days, every three days, every four days, every five days, every six days, every seven days or less, such as every two weeks, once a month, once every two months, four times a year, three times a year, two times a year or once a year.

Adenosine Agonists

Agonists to be used in the methods of the invention are generally those that are selective for the $A_{2a}$ receptor, or an agonist of downstream signals such as increased cAMP, increased activation of PKA, MAP kinases, PKC, Epac or phospholipase D. Agonists can be either full or partial agonists at the receptor. In certain instances, non-selective agonists are also useful. Nonselective adenosine receptor agonist include 5-N-ethylcarboxamidoadenosine (NECA), adenosine and methylxanthines. Selective $A_{2a}$ receptor agonists include 2-p-(2-carboxyethyl)phenethyl-amino-5-N-ethyl-carboxamidoadenosine (CGS21680), ATL-146e, 2-chloro-N-6-cyclopentyl adenosine (CCPA) and regadenoson (also known as CVT-3146).

Partial agonists may be present in *Hypericum perforatum* and *Valeriana officinalis*. In addition, selective agonists are being developed by Adenosine Therapeutics.

In certain embodiments, the $A_{2a}$ receptor agonist is linked to a molecule to increase bioavailability and/or stability. The agonist can also be linked to a molecule that allows targeting of the antibody to particular tissues or regions, or to 'present' the drug to T cells. In certain instances, this molecule is a polymer such as a polyethylene glycol moiety.

Immunosuppressive Agents

Immunosuppressive drugs or immunosuppressants are drugs that are used in immunosuppressive therapy to inhibit or prevent activity of the immune system. Clinically they are used to prevent the rejection of transplanted organs and tissues (e.g. bone marrow, heart, kidney, liver), treatment of autoimmune diseases or diseases that are most likely of autoimmune origin (e.g. rheumatoid arthritis, myasthenia gravis, systemic lupus erythematosus, Crohn's disease, and ulcerative colitis) and treatment of some other non-autoimmune inflammatory diseases (eg. long term Allergic Asthma control). In one embodiment, a method of reducing need for immunosuppressive therapy is provided comprising administering an $A_{2a}$ receptor agonist to a host receiving an immunosuppressive agent.

Immunosuppressive drugs can be classified into five groups: glucocorticoids; cytostatics; antibodies; drugs acting on immunophilins; and other drugs.

In pharmacologic (supraphysiologic) doses, glucocorticoids are used to suppress various allergic, inflammatory, and autoimmune disorders. They are also administered as posttransplantory immunosuppressants to prevent the acute transplant rejection and graft-versus-host disease. Nevertheless, they do not prevent an infection and also inhibit later reparative processes.

Cytostatics inhibit cell division. In immunotherapy, they are used in smaller doses than in the treatment of malignant diseases. They affect the proliferation of both T cells and B cells. Due to their highest effectiveness, purine analogs are most frequently administered. Some cytostatics are alkylating agents. The alkylating agents used in immunotherapy are nitrogen mustards (cyclophosphamide), nitrosoureas, platinum compounds and others. Cyclophosphamide is probably the most potent immunosuppressive compound. In small doses, it is very efficient in the therapy of systemic lupus erythematosus, autoimmune hemolytic anemias, Wegener's granulomatosis and other immune diseases. High doses cause pancytopenia and hemorrhagic cystitis. Antimetabolites are also used as immunosuppressive compounds. Antimetabolites interfere with the synthesis of nucleic acids. These include: folic acid analogues, such as methotrexate; purine analogues such as azathioprine and mercaptopurine; pyrimidine analogues; and protein synthesis inhibitors.

Cytotoxic antibiotics are also used for immunosuppression. Among these, dactinomycin is the most typical. It is used in kidney transplantations. Other cytotoxic antibiotics are anthracyclines, mitomycin C, bleomycin, mithramycin. Certain antibodies are also used as immunosuppressive agents.

Approved antibodies for transplant rejection include OKT3®, Simulect® and Zenapax (daclizumab). Furthermore, Fc-fusion proteins can be used for transplant rejection, such as fusion with mutants of or receptors for certain interleukins (IL-15 and IL-17 receptor for example). Fc-fusion proteins can also include modifications to decrease side effects of the administration.

Interleukin-2 is an important immune system regulator necessary for the clone expansion and survival of activated lymphocytes T. By the use of the recombinant gene technology, the mouse anti-Tac antibodies have been modified leading to the presentation of two himeric mouse/human anti-Tac antibodies in the year 1998: basiliximab (Simulect®) and daclizumab (Zenapax®). These drugs act by binding the IL-$_{2a}$ receptor's α chain, preventing the IL-2 induced clonal expansion of activated lymphocytes and shortening their survival. They are used in the prophylaxis of the acute organ rejection after the bilateral kidney transplantation, both being similarly effective and with only few side effects.

Together with tacrolimus, cyclosporin is a calcineurin inhibitor. It has been in use since 1983 and is one of the most widely used immunosuppressive drugs. It is a fungal peptide, composed of 11 amino acids. Cyclosporin is thought to bind to the cytosolic protein cyclophilin (an immunophilin) of immunocompetent lymphocytes, especially T-lymphocytes. This complex of cyclosporin and cyclophilin inhibits calcineurin, which under normal circumstances induces the transcription of interleukin-2. The drug also inhibits lymphokine production and interleukin release, leading to a reduced function of effector T-cells.

Tacrolimus (Prograf™, FK506) is a fungal product (*Streptomyces tsukubaensis*). It is a macrolide lactone and acts by inhibiting calcineurin. The drug is used particularly in the liver and kidney transplantations, although in some clinics it is used in heart, lung and heart/lung transplants. It binds to an immunophilin, followed by the binding of the complex to calcineurin and the inhibition of its phosphatase activity. In this way, it prevents the passage of G0 into G1 phase. Tacrolimus is more potent than cyclosporin and has less pronounced side effects.

Sirolimus (Rapamune™, Rapamycin) s is a macrolide lactone, produced by the actinomycetes *Streptomyces hygroscopicus*. It is used to prevent rejection reactions. Although it is a structural analogue of tacrolimus, it acts somewhat differently and has different side effects. Other rapalogues are also useful as immunosuppressive agents in the present invention.

Other drugs include interferons. IFN-β suppresses the production of Th1 cytokines and the activation of monocytes. It is used to slow down the progression of multiple sclerosis. IFN-γ is able to trigger lymphocytic apoptosis. In addition, opioids can be useful. Prolonged use of opioids may cause immunosuppression of both innate and adaptive immunity. Decrease in proliferation as well as immune function has been observed in macrophages as well as lymphocytes. It is thought that these effects are mediated by opioid receptors expressed on the surface of these immune cells. A TNF-α (tumor necrosis factor alpha) binding protein is a monoclonal antibody or a circulating receptor such as infliximab (Remicade®), etanercept (Enbrel®), or adalimumab (Humira®) that binds to TNF-α and prevent it from inducing the synthesis of IL-1 and IL-6 and the adhesion of lymphocyte activating molecules. They are used in the treatment of rheumatoid arthritis, ankylosing spondylitis, Crohn's disease and psoriasis. TNF or the effects of TNF are also suppressed by various natural compounds, including curcumin (an ingredient in turmeric) and catechins (in green tea).

Mycophenolic acid acts as a non-competitive, selective and reversible inhibitor of inosine monophosphate dehydrogenase (IMPDH), which is a key enzyme in the de novo guanosine nucleotide synthesis. In contrast to other human cell types, lymphocytes B and T are very dependent on this process.

Small biological agents are also useful. FTY720 is a new synthetic immunosuppressant, currently in phase 3 of clinical trials. It increases the expression or changes the function of certain adhesion molecules (α4/β7 integrin) in lymphocytes, so they accumulate in the lymphatic tissue (lymphatic nodes) and their number in the circulation is diminished. In this respect, it differs from all other known immunosuppressants.

Agents used to treat skin inflammatory conditions include Acitretin, Alclometasone dipropionate, Allantoin/Coal tar extract/Hydrocortisone, Alphaderm, Alphosyl HC, Asmanex, Benzalkonium chloride/Dimeticone 350/Hydrocortisone/Nystatin, Betacap, Betamethasone dipropionate, Betamethasone dipropionate/Calcipotriol hydrate, Betamethasone dipropionate/Salicylic acid, Betamethasone Valerate, Betamethasone Valerate/Clioquinol, Betamethasone Valerate/Fusidic Acid, Betamethasone valerate/Neomycin sulphate, Betnovate, Betnovate-C, Betnovate-N, Bettamousse, Calcipotriol, Calcipotriol hydrate, Calcitriol, Calmurid HC, Canesten HC, Chlorquinaldol/Hydrocortisone Butyrate, Ciclosporin, Clarelux, Clioquinol/Hydrocortisone, Clobetasol propionate, Clobetasol propionate/Neomycin sulphate/Nystatin, Clobetasone butyrate, Clobetasone butyrate/Nystatin/Oxytetracycline calcium, Clotrimazole/Hydrocortisone, Crotamiton/Hydrocortisone, Cutivate, Daktacort, Dandrazol, Dermovate, Dermovate-NN, Dioderm, Diprosalic, Diprosone, Dithranol, Dithrocream, Dovobet, Dovonex, Dovonex cream, Econacort, Econazole nitrate/Hydrocortisone, Efalizumab, Efcortelan, Elidel, Enbrel, Etanercept, Eumovate, Eurax Hydrocortisone, Fluticasone propionate, Fucibet, Fucidin H, Fucidin H ointment, Fusidic acid/Hydrocortisone acetate, Gramicidin/Neomycin sulphate/Nystatin/Triamcinolone acetonide, Hydrocortisone, Hydrocortisone acetate/Sodium fusidate, Hydrocortisone butyrate, Hydrocortisone/Lactic Acid/Urea, Hydrocortisone/Miconazole nitrate, Hydrocortisone/Urea, Infliximab, Kenalog, Ketoconazole, Locoid, Locoid C, Maxtrex, Methotrexate, Methotrexate sodium, Modrasone, Mometasone, Nasofan, Neoral, Neotigason, Nizoral, Pimecrolimus, Protopic, Raptiva, Remicade, Silkis, Tacrolimus monohydrate, Tazarotene, Timodine, Tri-Adcortyl, Triamcinolone acetonide, Trimovate, Vioform-Hydrocortisone and Zorac.

Inhibitors of Co-Stimulatory Molecules

The CD28 molecule on T cells delivers a costimulatory signal upon engaging either of its ligands, B7.1 (CD80) or B7.2 (CD86) and possibly B7.3. A distinct signal is transduced by the CD40L (for ligand) molecule on the T cell when it is ligated to CD40. A number of other molecules on the surface of APC may serve some role in costimulation, although their full role or mechanism of action is not clear. These include VCAM-1, ICAM-1 and LFA-3 on APC and their respective ligands VLA-4, LFA-1 and CD2 on T cells. It is likely that the integrins LFA-1 and VCAM-1 (which is only expressed on activated and memory T cells) are involved in initiating cell-cell contact. LFA-1 (lymphocyte function associated protein 1) which blocks killing of target cells by CD8 cytotoxic T cells. LFA-1 binds the immunoglobulin superfamily ligands ICAM-1, -2, -3. Blocking beta-2 integrin is a very effective way of inhibiting immune responses and monoclonal antibodies against this protein are in clinical trial for treatment of transplant recipients and other conditions. Other immunotherapeutics in development are $CTLA_4$-Ig, which is a soluble from of a high affinity receptor for B7.1 and B7.2 (more avid than CD28), and anti-CD40L; both block co-stimulation of T cells and anti-CD40L may also block reciprocal activation of antigen presenting cells.

In some embodiments, the agonist is administered in combination or alternation with an costimulatory molecule that induces anergy. In some instances, the molecule is a B7-H4 protein or fragment, or a variant or fusion protein thereof. In some instances, the molecule is one described in PCT Publication Nos. WO 08/083239, WO 08/083228, WO 07/124361, WO 07/082154, WO 02/10187 or US Patent Publication No. 2007/0218032 or U.S. Pat. No. 6,891,030.

Enhancing Suppressive Antibody Signals

In some embodiments, the method comprises administration of an $A_{2a}$ Receptor agonist in combination or alternation with one or more suppressive antibody formulations.

Antibodies are used as a quick and potent immunosuppression method to prevent the acute rejection reaction. Heterologous polyclonal antibodies are obtained from the serum of animals (e.g. rabbit, horse) and injected with the patient's thymocytes or lymphocytes. The antilymphocyte (ALG) and antithymocyte antigens (ATG) are being used. These compositions include Atgam®, obtained from horse serum, and Thymoglobuline®, obtained from rabbit serum. They are part of the steroid-resistant acute rejection reaction and grave aplastic anemia treatment. However, they are primarily added to other immunosuppressives to diminish their dosage and toxicity. They also allow transition to cyclosporine therapy.

Monoclonal antibodies are directed towards exactly defined antigens. Therefore, they cause fewer side effects. Especially significant are the IL-2 receptor (CD25) and CD3 directed antibodies. They are used to prevent the rejection of transplanted organs, but also to track changes in the lymphocyte subpopulations.

Approved antibodies for transplant rejection include OKT3®, Simulect® and Zenapax (daclizumab). Furthermore, Fc-fusion proteins can be used for transplant rejection, such as fusion with mutants of or receptors for certain interleukins (IL-15 and IL-17 receptor for example). Fc-fusion proteins can also include modifications to decrease side effects of the administration.

Additional antibodies useful for treating or preventing certain disorders are those useful for autoimmune disorders, inflammation, allergic reactions and cancer (HUMIRA (Abbott) for treatment of various forms of arthritis and Chron's disease, ABT-874, CAT-354, GC-1008, MYO-029 and MEDI-528.

In particular embodiments, the agonist is administered in combination or alternation with an Intravenous immunoglobulin (IVIG), a blood product generally administered intravenously that contains pooled IgG immunoglobulins (antibodies extracted from the plasma of over a thousand blood donors). Typically IVIG therapy is useful for treatment of Immune deficiencies such as X-linked agammaglobulinemia, hypogammaglobulinemia (primary immune deficiencies), and acquired compromised immunity conditions ([secondary immune deficiencies), featuring low antibody levels; Inflammatory and autoimmune diseases; and Acute infections. In certain embodiments, the formulations are used to treat Allogeneic bone marrow transplant, Chronic lymphocytic leukemia, Idiopathic thrombocytopenic purpura, Pediatric HIV, Primary immunodeficiencies, Kawasaki disease, Kidney transplant with a high antibody recipient or with an ABO incompatible donor or Common Variable Immune Deficiency. In some embodiments, these formulations are directed to specific infectious diseases, such as respiratory syncytial virus (RSV), hepatitis B (Hepatitis B Immune Globulin-HBIG), rabies (Rabies Immune Globulin-RIG), tetanus (Tetanus Immune Globulin-TIG) and varicella (chickenpox) (Varicella Zoster Immune Globulin-VZIG). In some embodiments, the co-administration increases generation of memory T cells in individuals receiving the antibody and enhances the efficacy of the antibody therapy.

Diseases or Disorders

The $A_{2a}$ receptor agonists can generally be administered to a host at risk of, or suffering from, a condition related to hyperactivity of the immune system, including an autoimmune disease. These conditions can be initiated in response to a pathogenic insult. For example, the conditions can occur due to infection, allergens, autoimmune stimuli, immune response to transplanted tissue, noxious chemicals, and toxins, ischemia/reperfusion, hypoxia, mechanical and thermal trauma, as well as growth of tumors. Inflammation is normally a localized action that results in expulsion or dilution of a pathogenic agent, resulting in isolation of the damaging agent and injured tissue. In certain cases, an immune response can occur to innocuous antigens that lead to symptomatic reactions upon re-exposure are called hypersensitivity reactions. These can cause hypersensitivity diseases if they occur repetitively.

In other embodiments, the host is suffering from, or at risk for, a transplant rejection. In some instances, the transplant is a solid organ transplant. In certain instances, the rejection is mediated by a rejection of endothelial cells in the transplant. In some instances, the rejection is not a hyperacute rejection. In other cases, the rejection is in part a hyperacute rejection. In some instances, the rejection is of a donor kidney, liver or heart, or portion thereof.

Autoimmune diseases arise from an overactive immune response of the body against substances and tissues normally present in the body. Generally autoimmune disorders are those in which the immune system produces an immune response (e.g. a B cell or a T cell response) against an endogenous antigen, with consequent injury to tissues. There are more than 40 human diseases classified as either definite or probable autoimmune diseases, and they affect 5% to 7% of the population. Almost all autoimmune diseases appear without warning or apparent cause, and most patients suffer from fatigue. Systemic autoimmune syndromes include SLE, Sjögren's syndrome, Scleroderma, Rheumatoid Arthritis and polymyositis. Local syndromes may be endocrinologic (DM Type 1, Hashimoto's thyroiditis, Addison's disease etc.), dermatologic (pemphigus vulgaris), haematologic (autoimmune haemolytic anaemia), neural (multiple sclerosis) or can involve virtually any circumscribed mass of body tissue.

The following diseases are generally accepted to be autoimmune related:

Acute disseminated encephalomyelitis (ADEM), is a form of encephalitis caused by an autoimmune reaction and typically occurring a few days or weeks after a viral infection or a vaccination.

Addison's disease, is often caused by autoimmune destruction of the adrenal cortex.

Ankylosing spondylitis, is a chronic, painful, progressive inflammatory arthritis primarily affecting spine and sacroiliac joints, causing eventual fusion of the spine.

Antiphospholipid antibody syndrome (APS), affects the blood-clotting process. It causes blood clots to form in veins and/or arteries.

Aplastic anemia, is often caused by an autoimmune attack on the bone marrow.

Autoimmune hepatitis, is a disorder wherein the liver is the target of the body's own immune system.

Autoimmune Oophoritis, is a disorder in which the immune system attacks the female reproductive organs.

Coeliac disease, is a disease characterized by chronic inflammation of the proximal portion of the small intestine caused by exposure to certain dietary gluten proteins.

Crohn's disease, is a form of inflammatory bowel disease characterized by chronic inflammation of the intestinal tract. Major symptoms include abdominal pain and diarrhea. There is also evidence supporting the theory that Crohn's Disease is an infectious disease caused by *Mycobacterium avium* paratuberculosis.

Diabetes mellitus type 1, when it is characterized by a deficiency or absence of insulin production (Type I), is often the consequence of an autoimmune attack on the insulin-producing beta cells in the islets of Langerhans of the pancreas.

Gestational pemphigoid, is a pregnancy-related blistering condition where autoantibodies are directed against the skin.

Goodpasture's syndrome, is a disease characterised by rapid destruction of the kidneys and haemorrhaging of the lungs through autoimmune reaction against an antigen found in both organs.

Graves' disease, is the most common form of hyperthyroidism, and is caused by anti-thyroid antibodies that have the effect of stimulating (agonist) the thyroid into overproduction of thyroid hormone.

Guillain-Barré syndrome (GBS), is an acquired immune-mediated inflammatory disorder of the peripheral nervous system (i.e., not the brain and spinal column) It is also called acute inflammatory demyelinating polyneuropathy, acute idiopathic polyradiculoneuritis, acute idiopathic polyneuritis and Landry's ascending paralysis.

Hashimoto's disease, is a common form of hypothyroidism, characterised by initial inflammation of the thyroid, and, later, dysfunction and goiter. There are several characteristic antibodies (e.g., anti-thyroglobulin).

Idiopathic thrombocytopenic purpura, is an autoimmune disease where the body produces anti-platelet antibodies resulting in a low platelet count Kawasaki's Disease, is often caused by an autoimmune attack on the arteries around the heart.

Lupus erythematosus, is a chronic (long-lasting) autoimmune disease wherein the immune system, for unknown reasons, becomes hyperactive and attacks normal tissue. This attack results in inflammation and brings about symptoms. This is a "Non-organ-specific" type of autoimmune disease.

Multiple sclerosis, is a disorder of the central nervous system (brain and spinal cord) characterised by decreased nerve function due to myelin loss and secondary axonal damage.

Myasthenia gravis, is a disorder of neuromuscular transmission leading to fluctuating weakness and fatigue. Weakness is caused by circulating antibodies that block (antagonist) acetylcholine receptors at the neuromuscular junction.

Opsoclonus myoclonus syndrome (OMS), is a neurological disorder that appears to be the result of an autoimmune attack on the nervous system. Symptoms include opsoclonus, myoclonus, ataxia, intention tremor, dysphasia, dysarthria, mutism, hypotonia, lethargy, irritability or malaise. About half of all OMS cases occur in association with neuroblastoma.

Optic neuritis, is an inflammation of the optic nerve that may cause a complete or partial loss of vision.

Ord's thyroiditis, is a thyroiditis similar to Hashimoto's disease, except that the thyroid is reduced in size. In Europe, this form of thyroid inflammation is more common than Hashimoto's disease.

Pemphigus, is an autoimmune disorder that causes blistering and raw sores on skin and mucous membranes.

Pernicious anaemia, is an autoimmune disorder characterised by anaemia due to malabsorption of vitamin B12.

Polyarthritis in dogs, is an immune reaction severely affecting the joints of dogs. Although rare and of unknown cause it can render a dog immobile even at a very young age. Treatment includes cortisone-type drugs.

Primary biliary cirrhosis, appears to be an autoimmune disease that affects the biliary epithelial cells (BECs) of the small bile duct in the liver. Although the cause is yet to be determined, most of the patients (>90%) appear to have auto-mitochondrial antibodies (AMAs) against pyruvate dehydrogenase complex (PDC), an enzyme that is found in the mitochondria.

Rheumatoid arthritis, is an autoimmune disorder that causes the body's immune system to attack the bone joints.

Reiter's syndrome, seems to be an autoimmune attack on various body systems in response to a bacterial infection and the body's confusion over the HLA-B27 marker.

Sjögren's syndrome, is an autoimmune disorder in which immune cells attack and destroy the exocrine glands that produce tears and saliva.

Takayasu's arteritis, is a disorder that results in the narrowing of the lumen of arteries.

Temporal arteritis (also known as "giant cell arteritis"), is an inflammation of blood vessels, most commonly the large and medium arteries of the head. Untreated, the disorder can lead to significant vision loss.

Warm autoimmune hemolytic anemia, is a disorder characterized by IgM attack against red blood cells.

Wegener's granulomatosis, is a form of vasculitis that affects the lungs, kidneys and other organs.

In addition, several diseases are suspected or theorized to be linked to autoimmunity. These include: Alopecia universalis; Behçet's disease; Chagas' disease; Chronic fatigue syndrome; Dysautonomia; Endometriosis; Hidradenitis suppurativa; Interstitial cystitis; Lyme disease; Morphea; Neuromyotonia; Narcolepsy; Psoriasis; Sarcoidosis; Schizophrenia; Scleroderma; Ulcerative colitis; Vitiligo; and Vulvodynia.

In one embodiment, the compounds are administered for the treatment or prophylaxis of inflammatory disorders that include, but are not limited to, respiratory disorders (including asthma, COPD, chronic bronchitis and cystic fibrosis); cardiovascular related disorders (including atherosclerosis, post-angioplasty, restenosis, coronary artery diseases and angina); inflammatory diseases of the joints (including rheumatoid and osteoarthritis); skin disorders (including dermatitis, eczematous dermatitis and psoriasis); post transplantation late and chronic solid organ rejection; multiple sclerosis; autoimmune conditions (including systemic lupus erythematosus, dermatomyositis, polymyositis, Sjogren's syndrome, polymyalgia rheumatica, temporal arteritis, Behcet's disease, Guillain Barré, Wegener's granulomatosus, polyarteritis nodosa); inflammatory neuropathies (including inflammatory polyneuropathies); vasculitis (including Churg-Strauss syndrome, Takayasu's arteritis); inflammatory disorders of adipose tissue; and proliferative disorders (including Kaposi's sarcoma and other proliferative disorders of smooth muscle cells).

Specific disorders include rheumatoid arthritis, lupus erythematosus, Sjögren's syndrome, scleroderma (systemic sclerosis), dermatomyositis, polychondritis, polymyositis, polymyalgia rheumatica, osteoarthritis, septic arthritis, fibromyalgia, gout, pseudogout, spondyloarthropathies, such as ankylosing spondylitis, reactive arthritis (Reiter's syndrome), psoriatic arthropathy, enteropathic spondylitis and reactive arthropathy, vasculitis, such as polyarteritis nodosa, Henoch-Schönlein purpura, serum sickness, Wegener's granulomatosis, giant cell arteritis, temporal arteritis, Takayasu's arteritis, Behcet's syndrome, Kawasaki's disease (mucocutaneous lymph node syndrome) and Buerger's disease (thromboangiitis obliterans). In addition, autoimmune conditions such as acute disseminated encephalomyelitis, Addison's disease, ankylosing spondylitisis, antiphospholipid antibody syndrome, autoimmune hepatitis, Coeliac disease, Crohn's disease, diabetes mellitus, Graves' disease, Guillain-Barré syndrome, Hashimoto's disease, idiopathic thrombocytopenic purpura, Kawasaki's Disease, lupus erythematosus, multiple sclerosis, Mmyasthenia gravis, opsoclonus myoclonus syndrome, optic neuritis, Ord's thyroiditis, pemphigus, pernicious anaemia, primary biliary cirrhosis, Reiter's syndrome, Sjögren's syndrome, Takayasu's arteritis, temporal arteritis, warm autoimmune hemolytic anemia and Wegener's granulomatosis.

In other embodiments, certain inflammtory skin disorders are treated or prevented, such as dermatitis, eczematous dermatitis and psoriasis. In general inflammatory skin disease is a broad category that includes many conditions, ranging in severity from mild itching to serious medical health complications. Other conditions that are inflammatory skin disorders include eczema generally, acne and rosacea.

Other disorders to be treated or prophylactically prevented or reduced by the methods of the invention include post transplantation late and chronic solid organ rejection; multiple sclerosis; autoimmune conditions (including systemic lupus erythematosus, dermatomyositis, polymyositis, inflammatory neuropathies (Guillain Barré, inflammatory polyneuropathies), vasculitis (Wegener's granulomatosus, polyarteritis nodosa), and rare disorders such as polymyalgia rheumatica, temporal arteritis, Sjogren's syndrome, Bechet's disease, Churg-Strauss syndrome, and Takayasu's arteritis).

Pharmaceutical Compositions

The described compounds can be formulated as pharmaceutical compositions and administered for any of the disorders described herein, in a host, including a human, in any of a variety of forms adapted to the chosen route of administration, including systemically, such as orally, or parenterally, by intravenous, intramuscular, topical, transdermal or subcutaneous routes.

The compounds can be included in the pharmaceutically acceptable carrier or diluent in an amount sufficient to deliver to a patient a therapeutically effective amount to treat cancer or other disorders characterized by abnormal cell proliferation or cancer or the symptoms thereof in vivo without causing serious toxic effects in the patient treated.

A dose of the antagonists or agonists for the above-mentioned conditions will be in the range from about 1 to 75 mg/kg, or 1 to 20 mg/kg, of body weight per day, more generally 0.1 to about 100 mg per kilogram body weight of the recipient per day. The effective dosage range of the prodrug can be calculated based on the weight of the parent derivative to be delivered.

The compounds are conveniently administered in units of any suitable dosage form, including but not limited to one containing 7 to 3000 mg, or 70 to 1400 mg of active ingredient per unit dosage form. An oral dosage of 50-1000 mg is usually convenient, and more typically, 50-500 mg.

In certain instances, the antagonists or agonists should be administered to achieve peak plasma concentrations of the active compound of from about 0.2 to 70 µM, or about 1.0 to 10 µM. This may be achieved, for example, by the intravenous injection of an appropriate concentration of the active ingredient, optionally in saline, or administered as a bolus of the active ingredient.

The concentration of the antagonist or agonist in the drug composition will depend on absorption, inactivation and excretion rates of the extract as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The compounds may be administered at once, or may be divided into a number of smaller doses to be administered at varying intervals of time.

One mode of administration of the compounds is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compounds can be administered as a component of an elixir, suspension, syrup, wafer, chewing gum or the like. A syrup may contain, in addition to the active compounds, sucrose as a sweetening agent and certain preservatives, dyes and colorings and flavors. The compounds can also be mixed with other active materials that do not impair the desired action, or with materials that supplement the desired action, such as antibiotics, antifungals, anti-inflammatories, or other anti-autoimmune compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered in a solution, such as intravenously, preferred carriers are physiological saline or phosphate buffered saline (PBS).

In another embodiment, the compounds are prepared with carriers that will protect the derivatives against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art.

Liposomal suspensions (including liposomes targeted to infected cells with monoclonal antibodies to viral antigens) are also typical as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

In some embodiments, the compounds can be administered in a composition that enhances the half life of the compounds in the body. For example, the antagonist or agonists molecules can be linked to a molecule, such as a polyethylene glycol. In certain embodiments, the molecule can be used to target the compounds to a cell, for example as a ligand to a receptor. In some embodiments, the linking of the compound reduces the amount of times the compound is administered in a day or in a week. In other embodiments, the linkage can enhance the oral availability of the compounds.

In certain instances, the compositions will additionally comprise an immunogenic adjuvant. Antigens, especially when recombinantly produced, may elicit a stronger response when administered in conjunction with adjuvant. Alum is an adjuvant licensed for human use and hundreds of experimental adjuvants such as cholera toxin B are being tested. *Helicobacter pylori* is the spiral bacterium which selectively colonizes human gastric mucin-secreting cells and is the causative agent in most cases of nonerosive, gastritis in humans. Recent research activity indicates that *H. pylori*, which has a high urease activity, is responsible for most peptic ulcers as well as many gastric cancers. Many studies have suggested that urease, a complex of the products of the ureA and ureB genes, may be a protective antigen.

Immunogenicity can be significantly improved if an antigen is co-administered with an adjuvant, commonly used as 0.001% to 50% solution in phosphate buffered saline (PBS). Adjuvants enhance the immunogenicity of an antigen but are not necessarily immunogenic themselves. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune response. Aluminum hydroxide and aluminum phosphate (collectively commonly referred to as alum) are routinely used as adjuvants in human and veterinary vaccines. A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes. To efficiently induce humoral immune response (HIR) and cell-mediated immunity (CMI), immunogens are typically emulsified in adjuvants.

U.S. Pat. No. 4,855,283 granted to Lockhoff describes glycolipid analogs including N-glycosylamides, N-glycosylureas and N-glycosylcarbamates, each of which is substituted in the sugar residue by an amino acid, as immune-modulators or adjuvants. U.S. Pat. No. 4,258,029 granted to Moloney describes that octadecyl tyrosine hydrochloride (OTH) functions as an adjuvant when complexed with tetanus toxoid and formalin inactivated type I, II and III poliomyelitis virus vaccine. Octodecyl esters of aromatic amino acids complexed with a recombinant hepatitis B surface antigen, enhanced the host immune responses against hepatitis B virus. Bessler et al., "Synthetic lipopeptides as novel adjuvants," in the 44th Forum In Immunology (1992) at page 548 et seq. is directed to employing lipopeptides as adjuvants when given in combination with an antigen. The lipopeptides typically had P3C as the lipidated moiety and up to only 5 amino acids, e.g., P3C-SG, P3C-SK4, P3C-SS, P3C-SSNA, P3C-SSNA.

Antigens or immunogenic fragments thereof stimulate an immune response when administered to a host. In one embodiment, the antigen is a killed whole pneumococci, lysate of pneumococci or isolated and purified PspA, as well as immunogenic fragments thereof, particularly when administered with an adjuvant (see U.S. Pat. No. 6,042,838). The *S. pneumoniae* cell surface protein PspA has been demonstrated to be a virulence factor and a protective antigen (see WO 92/14488). In an effort to develop an immunogenic composition based on PspA, PspA was recombinantly expressed in *E. coli*. To efficiently express PspA, the mature PspA molecule of the Rx1 strain was truncated from its normal length of 589 amino acids to that of 314 amino acids comprising amino acids 1 to 314. This region of the PspA molecule contains most, if not all, of the protective epitopes of PspA.

Nardelli et al. (Vaccine (1994), 12(14):1335 1339) covalently linked a tetravalent multiple antigen peptide containing a gp120 sequence to a lipid moiety and orally administered the resulting synthetic lipopeptide to mice. Croft et al. (J. Immunol. (1991), 146(5): 793 796) have covalently coupled integral membrane proteins (Imps) isolated from *E. coli* to various antigens and obtained enhanced immune responses by intramuscular injection into mice and rabbits. Schlecht et al. (Zbl. Bakt. (1989) 271:493 500) relates to *Salmonella typhimurium* vaccines supplemented with synthetically prepared derivatives of a bacterial lipoprotein having five amino acids. Substantial effort has been directed toward the development of a vaccine for Lyme disease.

Dosing

When a compound is administered throughout the specification, the amount of antibody administered is an effective amount to effect the result indicated. Therefore, when an $A_{2a}$ Receptor antagonist is administered to enhance an immune response, the amount administered is an effective amount to produce the desired results.

The compounds are generally administered for a sufficient time period to alleviate the undesired symptoms and the clinical signs associated with the condition being treated. In one embodiment, the compounds are administered less than three times daily. In one embodiment, the compounds are administered in one or two doses daily. In one embodiment, the compounds are administered once daily. In some embodiments, the compounds are administered in a single oral dosage once a day. In certain embodiments, as described above, the agonists are administered in a specific order and in a particular time frame, to provide the tolerance inducing effects and reduce the use of immunosuppressive agents.

The active compound is included in the pharmaceutically acceptable carrier or diluent in an amount sufficient to deliver to a patient a therapeutic amount of compound in vivo in the absence of serious toxic effects. An effective dose can be determined by the use of conventional techniques and by observing results obtained under analogous circumstances. In determining the effective dose, a number of factors are considered including, but not limited to: the species of patient; its size, age, and general health; the specific disease involved; the degree of involvement or the severity of the disease; the response of the individual patient; the particular compound administered; the mode of administration; the bioavailability characteristics of the preparation administered; the dose regimen selected; and the use of concomitant medication.

Typical systemic dosages for the herein described conditions are those ranging from 0.01 mg/kg to 1500 mg/kg of body weight per day as a single daily dose or divided daily doses. Dosages for the described conditions typically range from 0.5-1500 mg per day. A more particularly dosage for the desired conditions ranges from 5-750 mg per day. Typical dosages can also range from 0.01 to 1500, 0.02 to 1000, 0.2 to 500, 0.02 to 200, 0.05 to 100, 0.05 to 50, 0.075 to 50, 0.1 to 50, 0.5 to 50, 1 to 50, 2 to 50, 5 to 50, 10 to 50, 25 to 50, 25 to 75, 25 to 100, 100 to 150, or 150 or more mg/kg/day, as a single daily dose or divided daily doses. In one embodiment, the daily dose is between 10 and 500 mg/day. In another embodiment, the dose is between about 10 and 400 mg/day, or between about 10 and 300 mg/day, or between about 20 and 300 mg/day, or between about 30 and 300 mg/day, or between about 40 and 300 mg/day, or between about 50 and 300 mg/day, or between about 60 and 300 mg/day, or between about 70 and 300 mg/day, or between about 80 and 300 mg/day, or between about 90 and 300 mg/day, or between about 100 and 300 mg/day, or about 200 mg/day. In one embodiment, the compounds are given in doses of between about 1 to about 5, about 5 to about 10, about 10 to about 25 or about 25 to about 50 mg/kg. Typical dosages for topical application are those ranging from 0.001 to 100% by weight of the active compound.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only.

Examples

Methods and Reagents

Reagents:

Cyclosporine A (Calbiochem, Cambridge, Mass.) was dissolved in ethanol and used at 1 uM. CGS-21680 (Sigma, St. Louis, Mo.) was dissolved in PBS and used at indicated concentrations. Anti-CD3 (2C11, BD PharMingen, San Diego, Calif.) was diluted in PBS and used at 1 ug/mL, as indicated. Soluble anti-CD28 (a kind gift from Dr. J. Allison, UC Berkeley, Calif.) was used at a $\frac{1}{1000}$ dilution. Hemagglutinin (HA) class II is an I-E$^d$ specific peptide (SFERFE-IFPKE) which was manufactured by The Johns Hopkins School of Medicine Oncology Department Peptide Synthesis Facility. Anti-phospho-ERK (Santa Cruz Biotechnology, Santa Cruz, Calif.) was used at 1:400 in 5% NFDM/TBS-tween (0.1%). Anti-p42/p44 MAPK (Cell Signaling Technology, Danvers, Mass.) was used at 1:500 in 5% BSA/TBS-tween (0.1%). Anti-jun B (Santa Cruz) and anti-Actin (Sigma) were both used at 1:1000 in 5% NFDM/TBS-tween (0.1%) mAbs used for staining: biotinylated anti-clonotypic 6.5 TCR (generously provided by H. Von Boehmer); avidin-PE (Caltag, Burlingame, Calif.); FITC-conjugated anti-CD4 (RM4-4); Cy-Chrome-conjugated anti-CD4 (RM4-5); PE-conjugated anti-Thy-1.1 (OX-7); FITC-conjugated anti-CD44 (1 M7); APC-conjugated anti-IFN-γ (XMG1.2); PE-conjugated anti-IL-17 (TC11-18H10); biotinylated anti-Thy1.2 (53-2.1) (all purchased from BD PharMingen). Anti-IFN-☐ and anti-IL-4 BD PharMingen) were used at 10 ug/mL. TGF-⌐ (Sigma) was used at 5 ng/mL. IL-6 (Peprotech, Rocky Hill, N.J.), was used at 20 ng/mL. FACSCalibur was used for flow cytometry event collection, and events were analyzed using FlowJo software (Ashland, Oreg.). Sorting was done with FACSAria (BD Biosciences, San Jose, Calif.).

Cell Culture:

A.E7 is a clonotypic CD4$^+$, Th1 T cell clone specific for pigeon cytochrome c (PCC) and is maintained as previously described (Powell et al. *J Immunol.* 1999; 162:2775-2784). A.E7s were rendered anergic with plate-bound anti-CD3 or by incubation with APC, PCC and 1 uM CGS.

Splenocytes and lymphocytes from A$_{2a}$ receptor wt or null 6.5$^+$ mice (see below) were harvested and enriched for CD4$^+$ T cells via negative selection with the CD4$^+$ T cell isolation kit and LS MACs column (all from Miltenyi Biotech, Auburn, Calif.). The T cells were then cultured in the presence or absence of 10 ug/mL HA class II peptide and 1 uM CGS. The T cells were rechallenged for 3-4 hours with 100 ug/mL HA class II peptide, GolgiStop (BD PharMingen) and irradiated APCs.

cAMP Production:

Total cAMP of naïve or previously activated cells were assayed with the Biotrak EIA system (Amersham Biosciences, Buckinghamshire, UK). For in vitro studies, A.E7 cells were mock stimulated or rendered anergic as above and rested for 24 hours. They were then harvested, extensively washed, and resuspended in media. 3.2~o15 cells were incubated with increasing amounts of CGS (as indicated) in a total volume of 180 pL at 37° C. After 40 minutes, whole cell lysates were generated and total cAMP levels were determined. To measure A$_{2a}$ receptor upregulation in primary T cells, splenocytes from A$_{2a}$ receptor wt or null mice were harvested and the incubated overnight in the presence or absence of soluble anti-CD3 (activated and nai've, respectively). The cells were assessed for cAMP similar to the in vitro cAMP studies.

Microarray:

In vitro microarray was performed as previously described (Safford et al. *Nat Immunol.* 2005; 6:472-480). In vivo microarray was performed as previously described (Huang et al. *Immunity.* 2004; 21:503-513). Briefly, A.E7s were stimulated with either PBS alone or plate-bound anti-CD3 in the absence or presence of CSA, then washed and rested. RNA was prepared with RNeasy kit (Qiagen) and probes were prepared per Affymetrix protocol.

Transgenic Mice:

The C3HA expressing transgenic (recipient) mice express hemagglutinin (HA) under the rat C3 promoter and has been previously described (Huang et al. *J Immunol.* 2003; 170:

3945-3953). The TCR-transgenic mouse line 6.5 (donor mice) has been previously described.[8] $A_{2a}$ receptor$^{-/-}$ mice were bred to this 6.5 mouse line. LAG-3 knockout mice on a C57/B6 were a generous gift of Dr. Dario Vignali. The LAG-3 KO genotype was bred onto a B10.D2 6.5$^+$ TCR background. All experiments involving the mice were performed in accordance with protocols approved by the Animal Care and Use Committee of The Johns Hopkins University School of Medicine.

Adoptive Transfer:

Clonotypic CD4$^+$ T cells were harvested from 6.5$^+$ transgenic mice. The unfractionated population was resuspended to contain $1.2 \times 10^6$ 6.5$^+$ T cells in 200 uL of HBSS for i.v. injection through the tail vein of C3HA mice. Recipient mice were given twice daily i.p. injections of vehicle (PBS alone) or CGS (2.5 mg/kg) in 100 uL volumes, on Days 1-4 following the transfer. No CGS was administered after Day 4. The percentage of CD4$^+$, 6.5$^+$, Thy 1.1$^-$, Thy 1.2$^-$ clonotypic T cells was determined by flow cytometric analysis. CD44 level was also analyzed to ensure that these clonotypic T cells were not activated in donor mice and were naive in phenotype. The cells were washed three times with HBSS and the unfractionated population was resuspended to contain the appropriate number of clonotypic T cells in 200 uL of HBSS for i.v. injection through the tail vein of C3HA.

Western Blot:

For phospho-ERK and total ERK Western blots, splenocytes from 6.5$^+$ mice were stimulated overnight with 10 ug/mL HA class II peptide then harvested and enriched for CD4$^+$ T cells. CD4$^+$ purified T cells were then stimulated in 500 uL with soluble anti-CD3 (10 ug/mL) and soluble anti-CD28 (1:20 dilution).

EMSA:

Nuclear extracts from CD4$^+$ purified 6.5$^+$ T cells that were prepared. The AP-1 probe was: 5'-CGC TTG ATG ACT CAG CCG GAA-3'. The NFkB probe was: 5'-AGT TGA GGG GAC TTT CCC AGG C-3'.

RT-PCR:

For in vitro studies, 5cc7 splenocytes were harvested and stimulated overnight with 10 uM PCC in the presence or absence of 1 uM CGS. The cells were harvested, mRNA isolated with Trizol and cDNA was generated. RT-PCR was performed as previously described (Safford et al. *Nat Immunol.* 2005; 6:472-480).

For in vivo studies, recipient C3HA mice were given $1.2 \times 10^6$ 6.5$^+$ donor T cells as described above. On Day 3, donor T cells were sorted and cDNA generated as above. RT-PCR was performed as previously described (Safford et al. *Nat Immunol.* 2005; 6:472-480).

LAG-3 primers and probe sets used were: Primer 5'-ACATCAACCAGACAGTGGCCA-3' (SEQ ID NO:1)/ Primer 5'-GCATCCCCTGGTGAAGGTC-3' (SEQ ID NO:2)/Probe 5'-6FAM-CCCACTCCCATCCCGGCCC-TAMRA-3' (SEQ ID NO:3)

FoxP3 primers and probe sets used were: Primer 5'-GGC CCT TCT CCA GOA CAG A-3' (SEQ ID NO:4)/Primer 5'-GCT GAT CAT GGC TGG GTT GT-3' (SEQ ID NO:5)/ Probe 5'-6FAM-ACT TCA TGC ATC AGC TCT CCA CTG TOG ATT AT-TAMRA-3' (SEQ ID NO:6)

IL-6 and TGF-β primers and probe sets were purchased from Applied Biosystems (Foster City, Calif.).

Th17 Driving Conditions:

$4 \times 10^6$ 5cc7 splenocytes were stimulated as previously described (Laurence et al. *Immunity.* 2007; 26:371-381).

Statistics:

Quantitative data were expressed as mean±standard deviation and compared using paired Student t tests. Values of p<0.05 were considered significant and are indicated by an asterisk (*).

Example 1

$A_{2a}$ Receptor Signaling During Activation Mimics Signal 1 Alone

Studies were conducted to determine the effects of $A_{2a}$ receptor stimulation on T cell function. A.E7 is a clonotypic CD4', Th1 T cell clone specific for pigeon cytochrome c (PCC) and is maintained as previously described (Powell, J. D., Lerner, C. G. & Schwartz, R. H. Inhibition of cell cycle progression by rapamycin induces T cell clonal anergy even in the presence of costimulation. *J Immunol* 162, 2775-84 (1999)). A.E7s were rendered anergic with anti-CD3 or by incubation with APC, PCC and 1 pM CGS-21680. For antibody induced anergy, 6-well plates were previously coated with anti-CD3 three hours prior to stimulation and washed with PBS. For mock stimulations, the well was not coated with anti-CD3. A.E7s were incubated in the coated well overnight at 37° C., then harvested and washed extensively and rested (24 hours for CAMP measurement, 4-6 days for proliferation and cytokine production). To test whether the $A_{2a}$ receptor-specific agonist CGS-21680 (CGS) induced anergy, $10 \times 10^6$ A.E7s were incubated with $100 \times 10^6$ irradiated BIO.A splenocytes (3000 rads) in the presence and absence of both 10 pM PCC and 1 pM CGS for 4 days at 37° C. A.E7s were then isolated via a ficoll gradient, washed extensively, and immediately rechallenged for proliferation and cytokine production. To assess proliferation to PCC, T cells were extensively washed and $5 \times 10^6$ cells were added to $50 \times 10^4$ irradiated BIO.A splenocytes and increasing doses of PCC in triplicate in a 96-well flat-bottomed plate. After 48 hours, cells were pulsed with [$^3$H] thymidine and harvested 16 hrs later. Tritium incorporation was determined by a Packard Matrix 96 direct beta counter (Packard bioscience). For cytokine production, a 96-well round-bottom plate was preincubated with 3 pg/mL anti-CD3 for 3 hours. The wells were washed and $10^5$ A.E7s were added in the presence of anti-CD28 and increasing doses of CGS (as indicated) in a total volume of 200 pL. All conditions were done in triplicate and were cultured overnight. Supernatant was collected and assessed for cytokine levels (eBioscience for IL-2, IFN-y, TNF-a; R&D Systems for GM-CSF) as per manufacturers' instructions. For each sample, multiple dilutions of the supernatant were assayed and concentration was determined based upon the dilution that best fit the most linear aspect of the standard curve. For CD25 measurements, the cells used for cytokine production were stained with anti-CD25, harvested and measured by flow cytometry.

Splenocytes and lymphocytes from $A_{2a}$ receptor wt or null, 6.5$^+$ mice were harvested and enriched for CD4' T cells via negative selection with the CD4$^+$ T cell isolation kit and LS MACs column (all from Miltenyi Biotech, Auburn, Calif.). The T cells were then cultured for in the presence or absence of 10 pg/mL HA class II peptide and 1 pM CGS. Irradiated splenocytes from mice of the same $A_{2a}$ receptor genotype were used as APCs, at a 10:1 ratio with T cells. After 3 days, the T cells were harvested and isolated via a ficoll gradient, washed extensively and immediately rechallenged for intracellular staining Briefly, the $1 \times 10^5$ T cells were stimulated for 3-4 hours with $5 \times 10^5$ irradiated $A_{2a}$ receptor wt APCs, I00 pg 1 mL HA class II peptide and a 1:1000 dilution of GolgiStop (BD PharMingen), in a total volume of 200 pL. After the stimulation, the cells were washed, stained with anti-6.5 and anti-CD4 antibodies, permeablized and fixed, then stained with anti-IFN-y antibody. Finally, the cells were washed and IFN-y production of CD4⁻, 6.5⁺ T cells was analyzed by flow cytometry.

Promotion of Tolerance In Vivo:

To determine the role of the $A_{2a}$ receptor in the induction of tolerance in vivo, we examined the effect of CGS administration in the mouse model of autoimmunity. For 4 days following the adoptive transfer of $1.2 \times 10^6$ 6.5 T cells into C3HA mice, the recipient mice were given twice daily i.p. injections of vehicle (PBS alone) or CGS (2.5mglkg) in 100 uL volumes. No CGS was administered after Day 4. A survival curve was generated from two separate experiments for a total of 17 mice for each condition.

Ex Vivo Tolerance Studies:

$1.2 \times 10^6$ clonotypic 6.5⁺ T cells were adoptive transferred into C3HA recipient mice as described above. On the second or third day (as noted) after transfer the splenocytes and lymphocytes were harvested and pooled. $2 \times 10^5$ of the pooled cells were incubated in 96-well round bottom plates with varying concentrations of HA class II peptide for 24 hours. A portion of the supernatant were withdrawn and later assayed for IL-2 and IFN-γ productions by ELISA. The wells were then pulsed with [³H]thymidine for 16 hours and proliferation determined by tritium incorporation, as described above. All samples were performed in triplicate.

In Vivo Suppression:

It has been shown that mice that survive the initial transfer of donor T cells can survive subsequent transfer of higher numbers of clonotypic T cells. To determine if adenosine mediates the formation of T regulatory cells, in vivo, we gave the surviving mice from FIG. 4a a transfer of $25 \times 10^6$ clonotypic T cells 4-6 weeks after the first transfer. No CGS is administered upon the second transfer.

RT-PCR:

Recipient mice are given $1.2 \times 10^6$ donor T cells as described above. On Day 4, cells from spleens and lymph nodes are harvested and pooled. They are enriched for CD4⁺ T cells via negative selection using biotinylated anti-CD8 (Ly-2, 53-6.7), anti-B220 (RA3-6B2) and anti-Thy 1.2(30-H12) antibodies (all from BD Biosciences PharMingen), and MACS streptavidin microbeads and AutoMACS column (Miltenyi Biotech) to deplete CD8⁺ T cells, B cells and recipient cells (Thy 1.2'). The remaining cells are then sorted on Thy 1. I and CD4 using FACSAria cell sorter to yield a CD4', 6.5' T cell population of greater than 95% purity. RT-PCR was performed as previously described'.

LAG-3 primers and probe sets used are: Primer 5'-ACAT-CAACCAGACAGTGGCCA-3' (SEQ ID NO:1)/Primer 5'-GCATCCCCTGGTGAAGGTC-3' (SEQ ID NO:2)/Probe 5'-6FAM-CCCACTCCCATCCCGG CCC-TAMRA-3' (SEQ ID NO:3)

When A.E7 cells, a clonal CD4⁺ Th1 T cell line, are stimulated with anti-CD3, rested and then re-challenged with anti-CD3 and anti-CD28, they fail to produce IL-2. Alternatively, blocking TCR signaling during the induction with cyclosporin A (CSA) restores IL-2 production to mock-stimulated levels Inhibition of IL-2 was the most pronounced, (ID$_{50}$ of 4.7 nM) compared to GM-CSF, TNF-α and IFN-γ ID$_{50}$s of 9.1 nM, 100 nM and 760 nM, respectively) (FIG. 1a). Maximal cytokine production, determined in the absence of $A_{2a}$ receptor agonist, was 233-788 pg/mL IL-2, 13.2-21.6 ng/mL GM-CSF, 102-263 ng/mL TNF-α and 507-583 ng/mL IFN-γ.

Activating A.E7 T cell clones with anti-CD3 and anti-CD28 antibodies in the presence of CGS resulted in a dose-dependent inhibition of cytokine production (see also Lappas, C. M., Rieger, J. M. & Linden, J. $A_{2a}$ adenosine receptor induction inhibits IFN-gamma production in murine CD4+ T cells. J Immunol 174, 1073-1080 (2005); Erdmann, A. A., et al. Activation of Th1 and Tc1 cell adenosine $A_{2a}$ receptors directly inhibits IL-2 secretion in vitro and IL-2-driven expansion in vivo. Blood 105, 4707-4714 (2005); Naganuma, M., et al. Cutting Edge: Critical Role for $A_{2a}$ Adenosine Receptors in the T Cell-Mediated Regulation of Colitis. J Immunol 177, 2765-2769 (2006)).

$A_{2a}$ receptor signaling did not inhibit TCR-induced CD25 expression suggesting that this inhibition is not due to global blockade of T cell activation (FIG. 1b). The cytokine profile of cells stimulated with anti-CD3 and anti-CD28 in the presence of the $A_{2a}$ receptor agonist, matched that of the cytokine profile seen in T cell anergy (Signal 1 alone). IL-2 production was markedly decreased followed by IFN-γ and GM-CSF (see FIG. 1b). Production of the chemokine MIP-1α which is induced with anti-CD3 stimulation alone, was not inhibited by CGS (FIGS. 1c and d). Maximal IL-2 production of activated cells ranged between 6420 and 7456 pg/mL, GM-CSF between 38.6 and 76.5 ng/mL, IFN-γ from 707 to 1624 ng/mL and MIP1-α between 331 and 439 ng/mL. The overall cytokine hierarchy remained constant over the 3 independent experiments. Thus the cytokine profile of full T cell activation (Signal 1+2) in the presence of $A_{2a}$ receptor signaling mimicked the cytokine profile seen during the induction of anergy (Signal 1 alone).

Example 2

$A_{2a}$ Receptor Engagement Promotes Long-Term Tolerance and LAG-3+ and Foxp3 Regulatory T Cells To test if $A_{2a}$ receptor activation during T cell activation might promote T cell anergy, A.E7 T cells (specific for the antigen PCC) were co-incubated with irradiated APCs in the presence or absence of both CGS and PCC (induction, primary stimulation). Next, the T cells were isolated and rechallenged with APCs and peptide in the absence of CGS (secondary stimulation).

Figure 2:
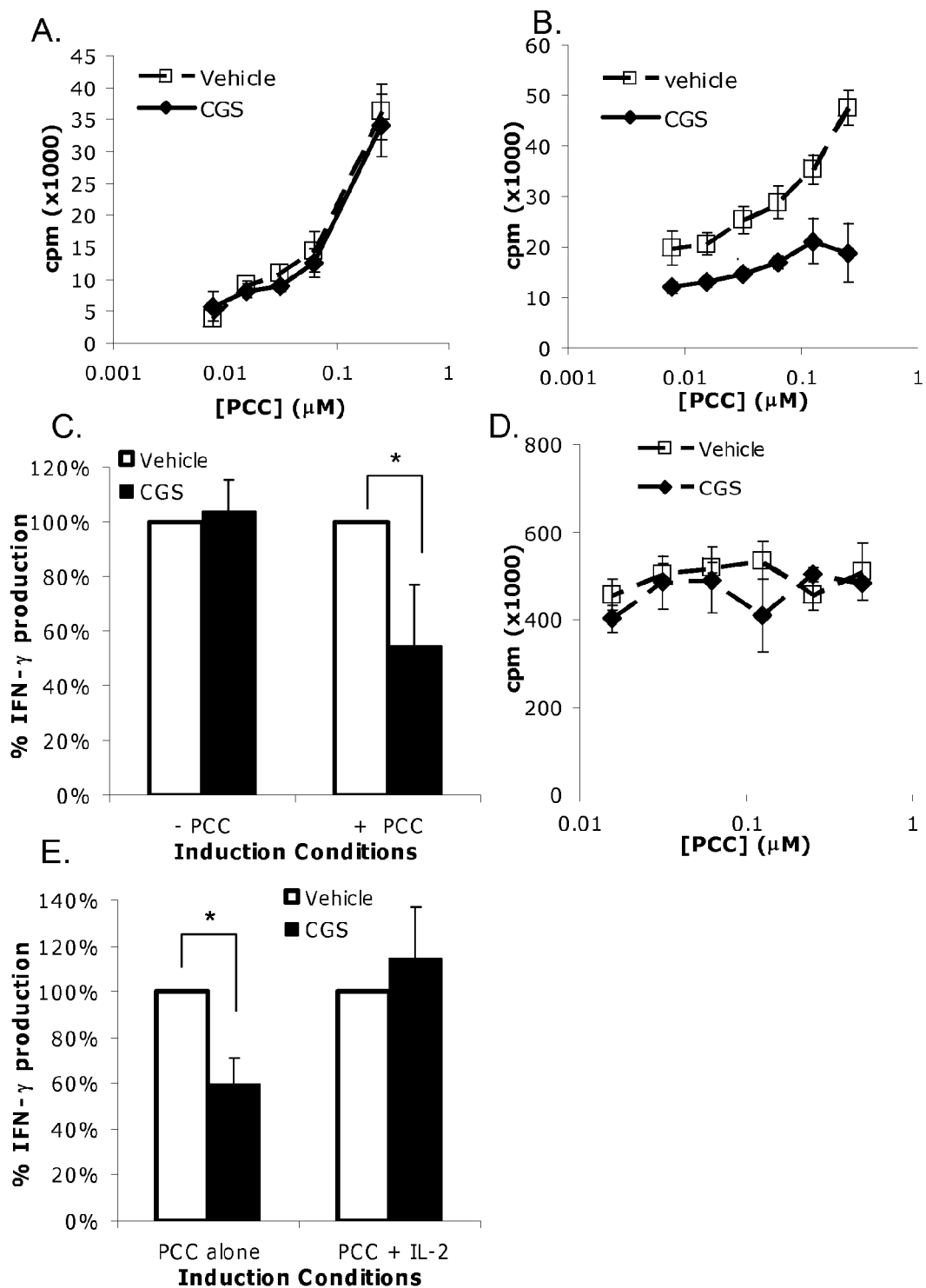
FIGS. 2(a)-(e) are graphs showing $A_{2a}$ receptor engagement during activation promotes T cell tolerance. 2(a) & (b) is graphs of proliferation upon rechallenge of A.E7 T cells following 4 day incubation without or with peptide (panel A or B, respectively) in the absence (open squares) or presence (solid diamonds) of 1 µM CGS. 2(c) is a graph of IFN-γ production upon rechallenge of A.E7 T cells following incubation without or with peptide (left or right side, respectively) in the absence (open bars) or presence (solid bars) of 1 µM CGS. 2(d) & (e) is graphs of proliferation and IFN-γ production upon rechallenge of A.E7s incubation with peptide and exogenous IL-2 in the absence or presence of 1 µM CGS. All data are representative of at least 3 independent experiments. (*: p>0.05)

Presence of CGS during a mock induction (no peptide present, no $A_{2a}$ receptor upregulation) had no effect upon subsequent rechallenge. (FIG. 2a). However, in the presence of peptide, the $A_{2a}$ receptor is upregulated and its activation promotes T cell anergy. When CGS is present during the initial stimulation, the T cells are rendered hyporesponsive such that they demonstrate reduced proliferation and IFN-γ production, even upon full stimulation. (FIGS. 2b and c)

It is known that the presence of exogenous IL-2 has the ability to prevent T cell anergy. IL-2 was added to the cultures stimulated in the presence or absence of CGS and then determined if the cells were anergic upon rechallenge. Consistent with anergy (Signal 1 alone), the presence of IL-2 prevented the ability of CGS to induce anergy (FIGS. 2d and e).

Figure 3:
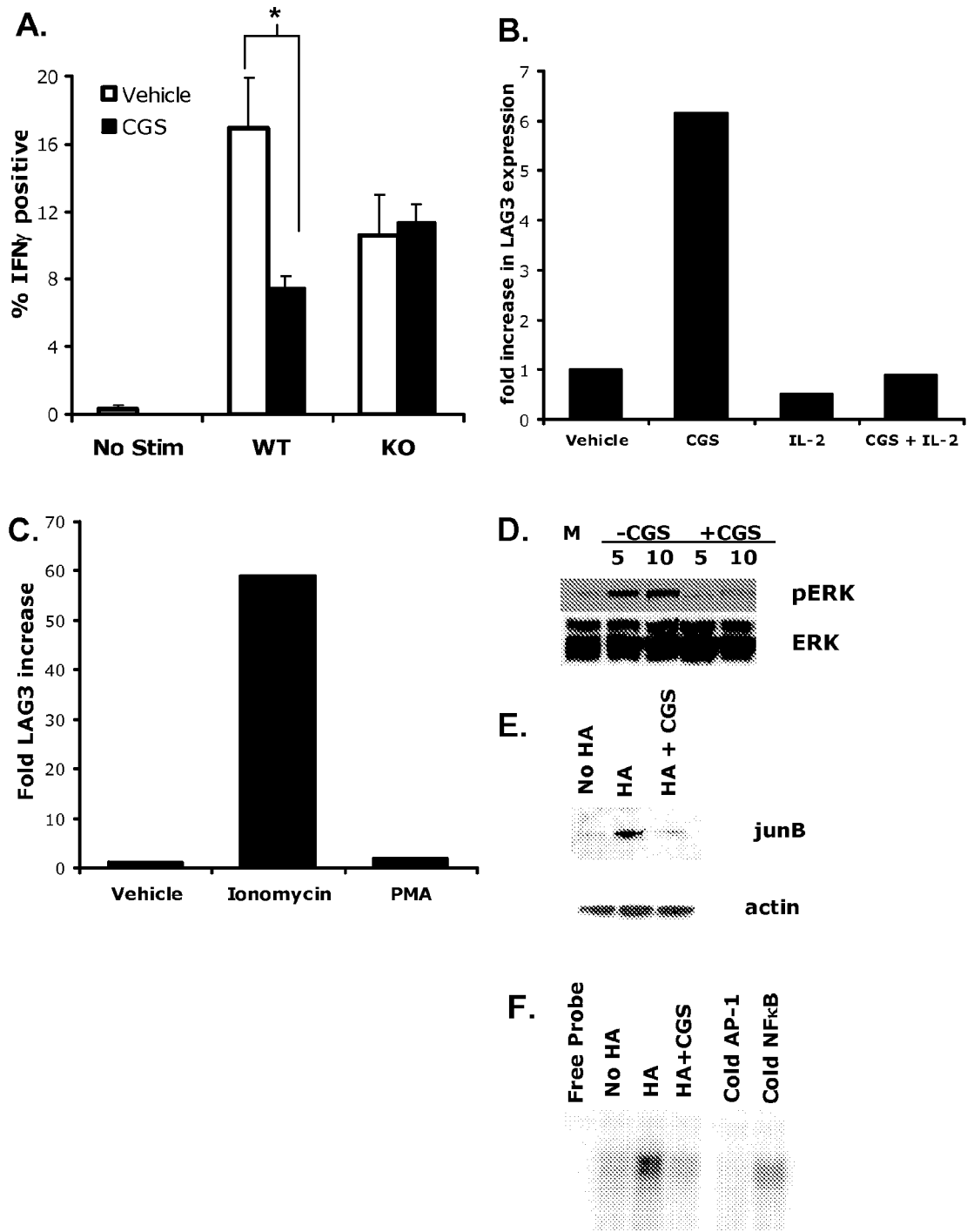
FIGS. 3(a)-(f) are graphs showing that $A_{2a}$ receptor signaling promotes the upregulation of LAG-3$^+$ in vitro.

Next we tested the ability of CGS to induce anergy in primary T cells. 6.5 TCR transgenic T cells were incubated with HA (their cognate antigen) in the presence or absence of CGS during the primary stimulation, and then rechallenged and assessed for IFN-□ production by intracellular staining. As was the case for the A.E7 T cell clones, $A_{2a}$ receptor signaling during the primary stimulation induced anergy such that the cells were hyporesponsive upon subsequent stimulation (FIG. 3a). $A_{2a}$ receptor null T cells were resistant to CGS-induced anergy, confirming the specificity of CGS for the $A_{2a}$ receptor. It has previously been shown that, in vivo, anergic 6.5+ transgenic T cells also develop regulatory function which is characterized by the expression of LAG-3. We thus tested the CGS-treated T cells for LAG-3 and found that $A_{2a}$ receptor signaling led to an increase in LAG-3 expression (FIG. 3b). As was the case for T cell anergy, the ability of CGS to induce LAG-3 was abrogated by the addition of exogenous IL-2.

It is known that the upregulation of LAG-3 is inhibited by CsA suggesting that it might be part of the NF-AT-induced inhibitory program. Indeed, LAG-3 is markedly upregulated by ionomycin alone further supporting this hypothesis (FIG. 3c). In light of these observations we hypothesized that one mechanism by which $A_{2a}$ receptor stimulation might be promoting anergy and LAG-3 expression is by inhibiting pathways which promote AP-1 activation. To test this hypothesis A.E7 T cells were stimulated with Signal 1+2 in the presence or absence of CGS (FIG. 3d). T cell stimulation in the absence of CGS led to robust phosphorylation of ERK, while T cell activation concomitant with $A_{2a}$ receptor stimulation inhibited ERK phosphorylation. Given that ERK phosphorylation ultimately leads to an increase in AP-1 activity, the effect of $A_{2a}$ receptor signaling on AP-1 levels in the nucleus were analyzed. Similar to the CGS effect on ERK phosphorylation, $A_{2a}$ receptor signaling during T cell stimulation led to reduced jun B expression in the nucleus (FIG. 3e) and lowered AP-1 binding as a whole (FIG. 3f). These data suggest that by inhibiting the activation of AP-1, $A_{2a}$ receptor signaling favors the induction of genes induced by NF-AT in the absence of AP-1.

Example 3

$A_{2a}$ Receptor Signaling Promotes Long-Term Tolerance, In Vivo

TCR transgenic 6.5+ T cells were adoptively transferred into C3HA mice that express HA as a self antigen (primarily in the lung). It is known that such cells initially are activated and proliferate but then become anergic by Day 4. The balance between the induction of peripheral tolerance and autoimmunity can be manipulated by adjusting the input of adoptively transferred 6.5+ T cells.

Figure 4:
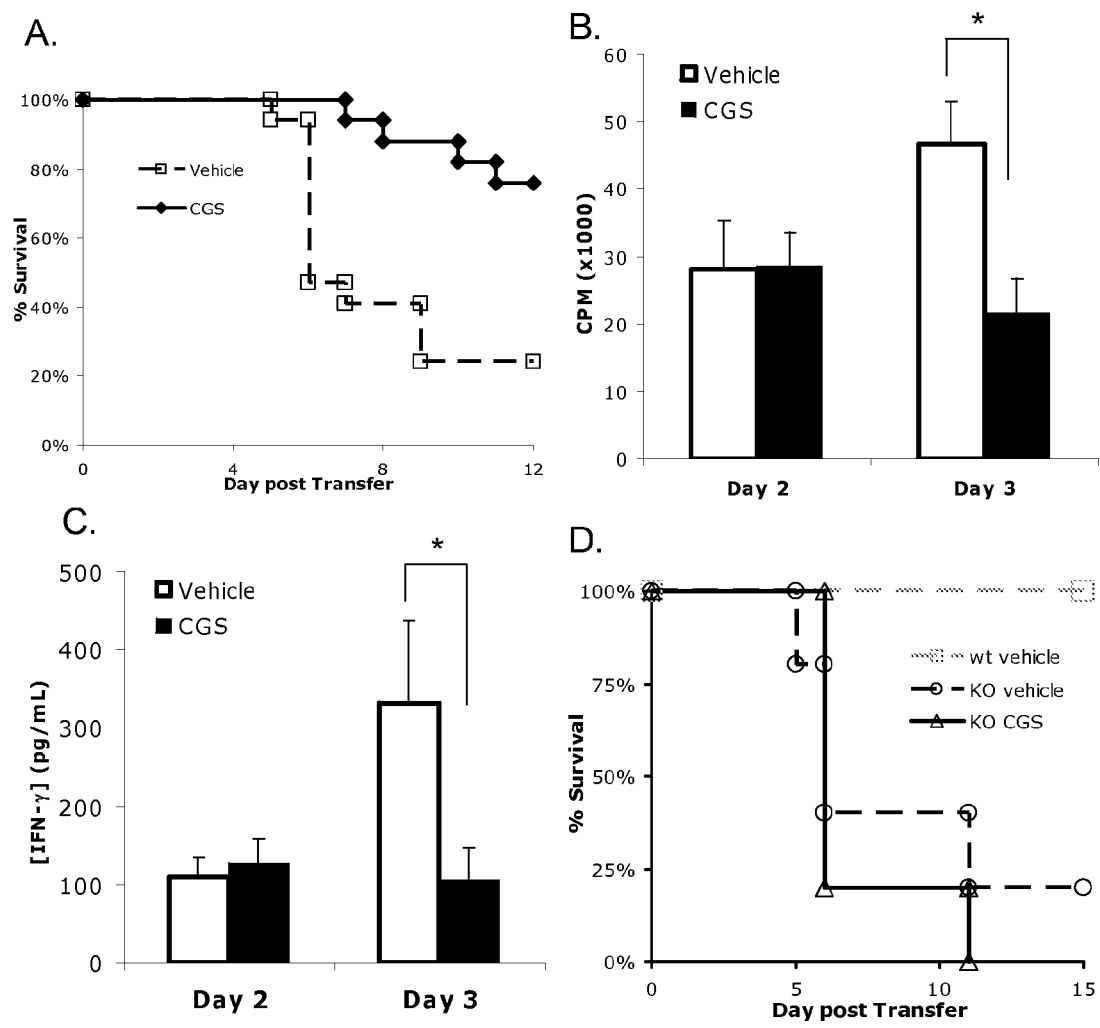
FIGS. 4(a)-(d) are graphs showing $A_{2a}$ receptor stimulation in vivo prevents death by autoimmunity and promotes T cell tolerance.

The effect of $A_{2a}$ receptor activation on tolerance induction and survival under conditions when mice would normally succumb to autoimmunity were tested. Approximately 80% of C3HA mice that received a lethal dose of 6.5+ T cells die of autoimmunity (FIG. 4a). In contrast, the administration of CGS for the four days immediately following T cell transfer led to the long-term survival of 80% of the mice. The fact that the mice did not experience autoimmunity when CGS was stopped suggests that the short course of CGS promoted the induction of tolerance, in vivo. Thus, the CGS was not merely acting as an immunosuppressive agent. To confirm this, C3HA mice were given clonotypic T cells, treated with CGS or vehicle, and their lymphocytes were harvested 2 or 3 days later. Cells harvested two days after adoptive transfer display equal proliferation and cytokine production, regardless of CGS treatment. By Day 3, however, the T cells derived from the CGS treated mice were hyporesponsive, displaying significant reduction in proliferation and IFN-γ production following in vitro stimulation when compared to T cells from vehicle-treated mice. (FIGS. 4b and c) Note that there is no CGS present during the rechallenge. The data depict the consequence of CGS exposure in vivo prior to rechallenge. By treating the mice with pharmacologic doses of an $A_{2a}$ receptor agonist tolerance could thus be induced.

The role of endogenous tissue-derived adenosine on the induction of tolerance, in vivo was analyzed. To this end, we transferred 6.5+ T cells from either $A_{2a}$ receptor KO or Wt control mice into $A_{2a}$ receptor Wt C3HA recipients. The dose of adoptively transferred T cells was titrated such that 100% of the mice survived the transfer of the Wt control T cells. In contrast, only 20% of the mice receiving the T cells from the $A_{2a}$ receptor null mice survived (FIG. 4d). CGS fails to protect the mice given $A_{2a}$ receptor KO T cells once again confirming that CGS acts specifically on the $A_{2a}$ receptor.

Example 4

$A_{2a}$ Receptor Engagement Promotes $T_{reg}$ in Vivo

A role for inducible regulatory T cells has been demonstrated in a number of in vivo models of tolerance. Recently, it has been shown both that the CD4 homologue LAG-3 is expressed on inducible regulatory T cells, in vivo, and that anti-LAG-3 antibodies have the ability to hasten the development of autoimmunity in the C3HA model. Alternatively, these LAG-3+ regulatory T cells have the ability to protect mice against subsequent rechallenge with normally lethal doses of clonotypic cells.

Figure 5:
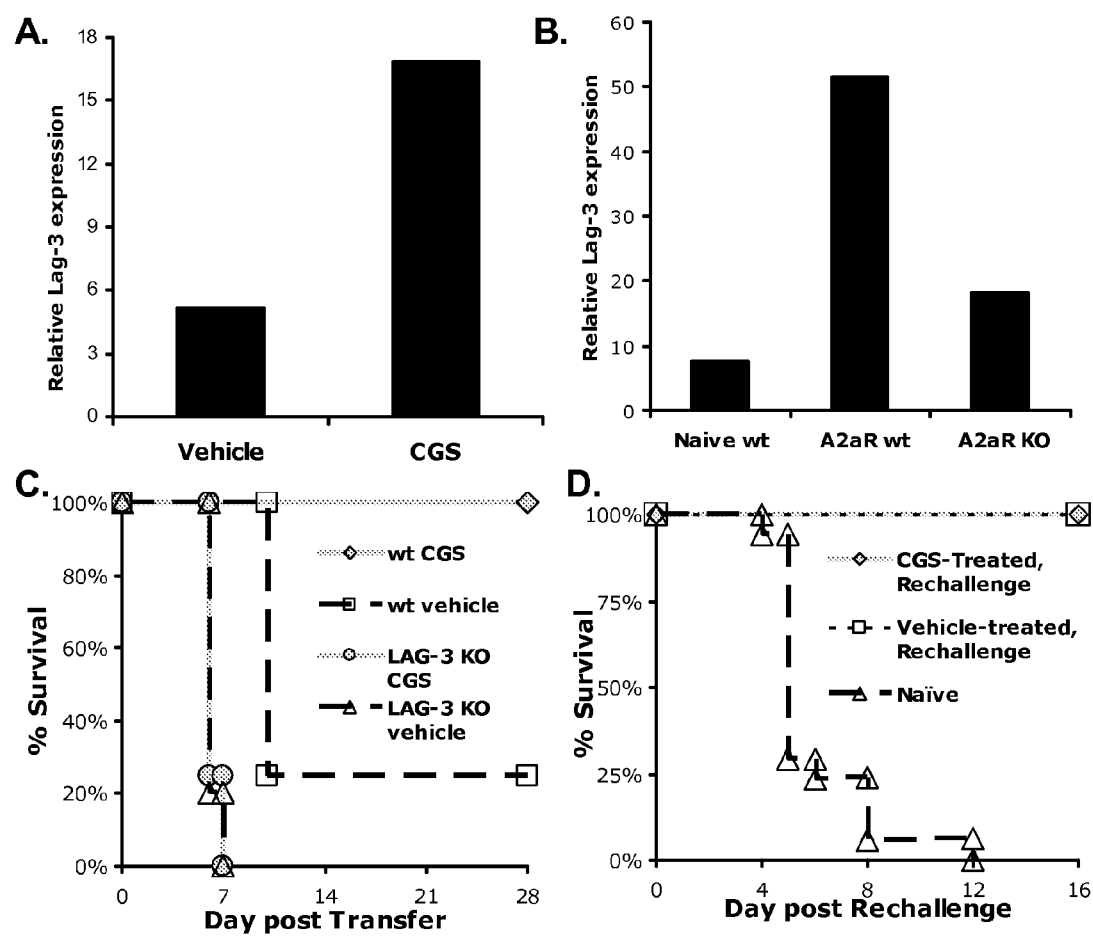
FIGS. 5(a)-(d) are graphs showing that $A_{2a}$ receptor signaling, in vivo, promotes regulatory T cells.

Tests were conducted to determine the effect of $A_{2a}$ receptor engagement on the induction of these regulatory T cells, in vivo. We found that the kinetics of LAG-3 expression were quicker and more robust in T cells from the CGS-treated mice when compared with vehicle treated mice (FIG. 5a). Likewise, there was less LAG-3 expression on T cells from $A_{2a}$ receptor KO mice (FIG. 5b).

Tests were conducted to determine if the ability of CGS to promote tolerance, in vivo, was in part related to the induction of LAG-3+ regulatory T cells. The ability of CGS to promote tolerance and prevent death was analyzed when LAG-3 null clonotypic T cells were adoptively transferred into C3HA mice (FIG. 5c). The adoptive transfer of LAG-3 KO T cells led to the rapid death of 100% of the C3HA hosts. In contrast, the adoptive transfer of Wt T cells led to delayed death and 25% survival. CGS was able to prevent death in 100% of the mice receiving Wt T cells but had no affect on the mice receiving LAG-3 null T cells. Thus, $A_{2a}$ receptor signaling appears to promote tolerance in part by promoting the generation of LAG-3− T regulatory cells.

Tests were conducted to determine if the CGS-induced clonotypic regulatory cells could protect the mice upon subsequent rechallenge with a second injection of clonotypic cells. An in vivo suppression assay was performed by adoptively transferring uniformly lethal numbers of clonotypic 6.5+ T cells ($2.5 \times 10^6$) into mice that had survived the initial adoptive transfer (and developed regulatory T cells) (FIG. 5d). As has been previously shown, the mice that survived the initial adoptive transfer (the 20% of the mice from FIG. 4a) all survive the second transfer while the transfer of cells into naïve C3HA mice resulted in 100% mortality. 100% of the mice that survived as a result of CGS treatment also survived the second adoptive transfer. Thus a short course of CGS treatment not only prevented acute autoimmunity and induced anergy, but it also promoted the induction of regulatory T cells, such that these mice were protected from a subsequent lethal challenge of autoreactive T cells over a month later.

Example 5

Tumors Evade the Immune System by Inducing Tolerance to Tumor Antigens

The microenvironment surrounding tumors contains high levels of adenosine (Spychala, J. Tumor-promoting functions of adenosine. *Pharmacol Ther* 87, 161-173 (2000)). Tests were conducted to analyze if tumor vaccines would be more effective in $A_{2a}$ receptor null mice. WT and $A_{2a}$ null mice were vaccinated in a model of metastatic cervical cancer.

Figure 6:
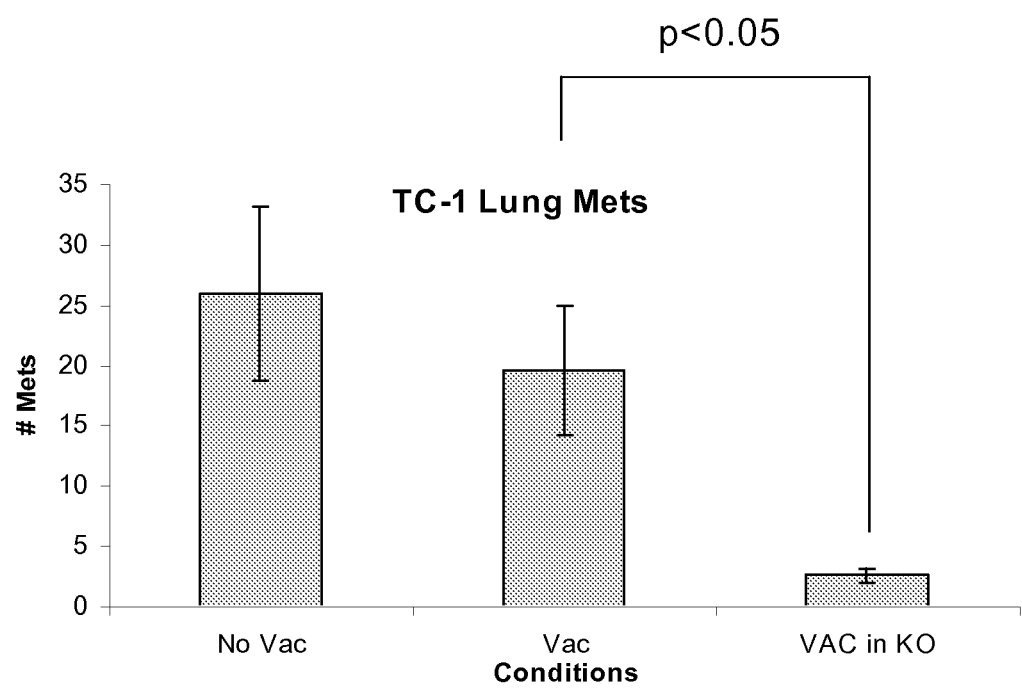
FIG. 6 is a graph of the number of lung metastases in either control mice injected with TC-1 tumor cells as a model of metastatic breast cancer, or $A_{2a}$ receptor knockout mice, which were either vaccinated with a single vaccinia tumor vaccine or not. C57B6 mice were inoculated with $10^4$ TC-1 tumor cells via tail vein. Mice were sacrificed 30+ days later and the lungs were analyzed for the number of lung metastases under a dissection microscope.
Figure 7:
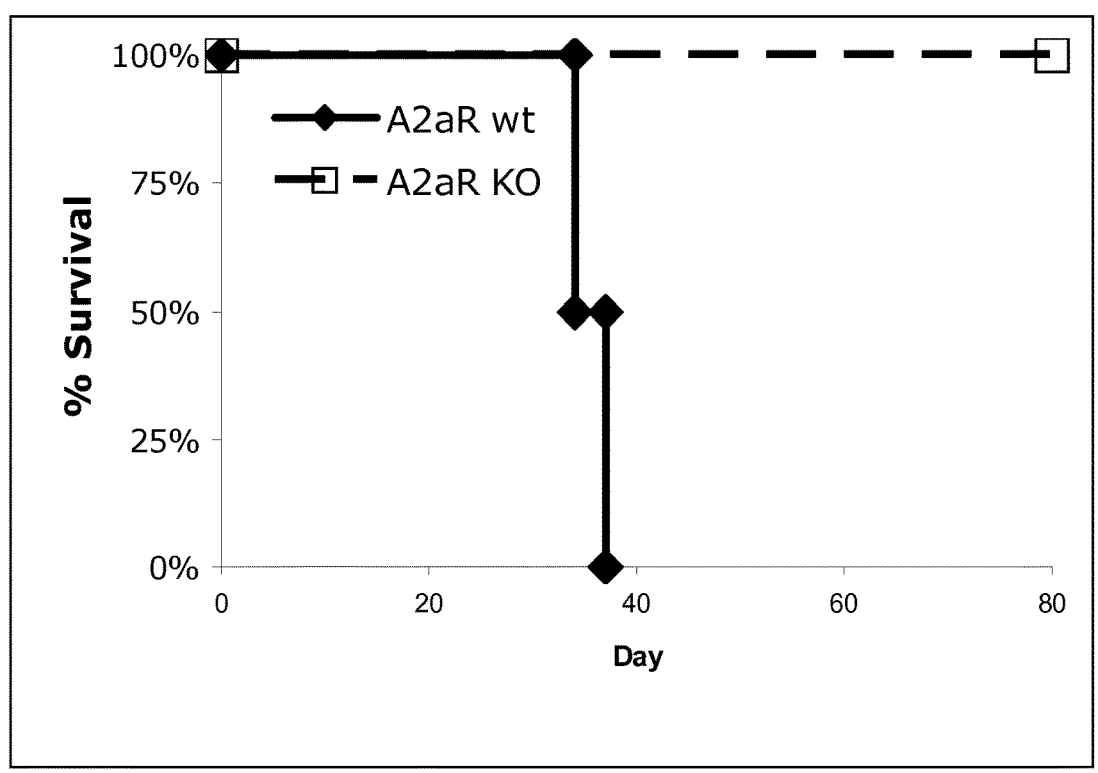
FIG. 7 is a graph of the percent survival between $A_{2a}$ receptor wild type or null mice that were given $5\times10^4$ TC-1 cells, a murine cervical cancer cell line. Mice were followed for survival for greater than 10 weeks.

As seen in FIG. 6, in this model vaccination of WT mice had no effect in preventing lung metastasis. On the other hand, vaccination of $A_{2a}$ receptor null mice markedly inhibited lung metastasis in the vaccinated mice. The further clinical implications of this model are seen in FIG. 7 demonstrating that at tumor doses that normally lead to death, $A_{2a}$ receptor$^{-/-}$ mice do not succumb.

Figure 8:
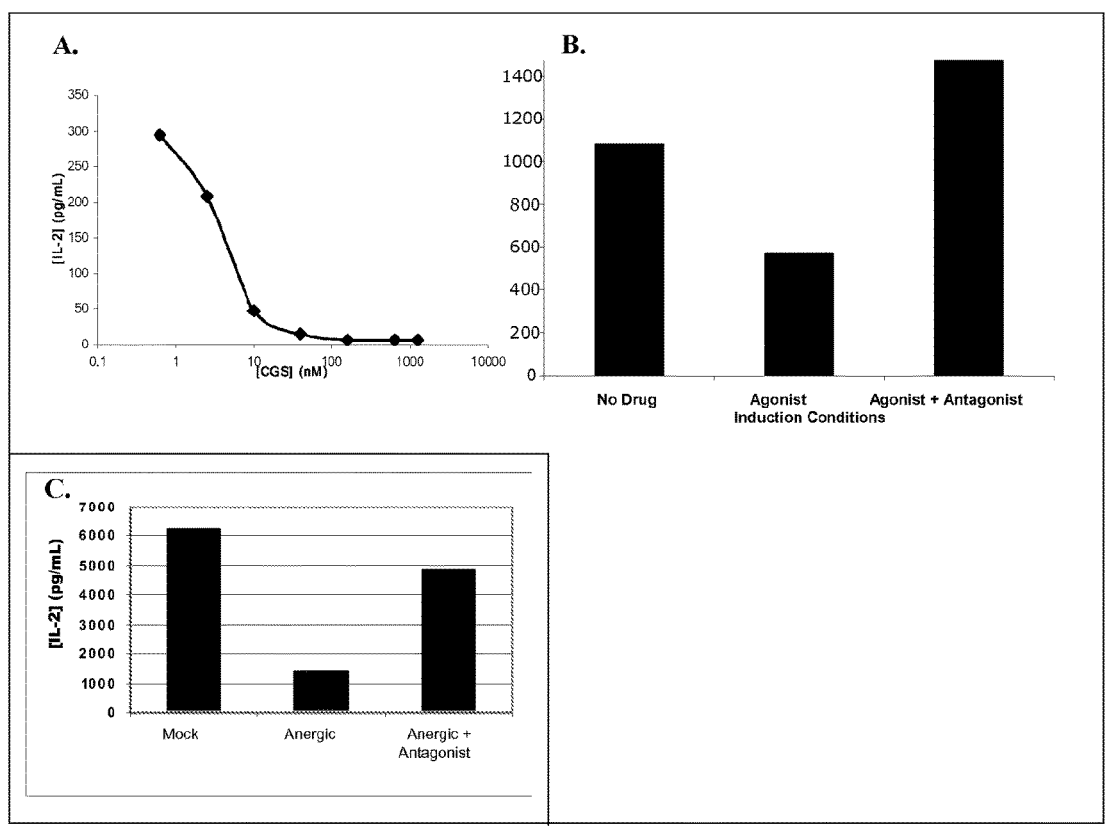
FIGS. 8(a)-(c) shows $A_{2a}$ receptor engagement during either the induction or the effector phase of the T cell response leads to tolerance. (A) T cells were activated with varying doses of $A_{2a}$ receptor specific agonist CGS-21680 (CGS), and IL-2 production measured; (B) T cells stimulated with APCs and peptide +/-$A_{2a}$ agonist CGS-21680 (CGS) and specific $A_{2a}$ receptor antagonist ZM-241385 (ZM; 4-(2-[7-amino-2-(2-furyl)[1,2,4]triazolo[2,3-a][1,3,5] triazin-5-ylamino]ethyl)phenol), T cells were harvested, washed and rechallenged with APCs and peptide in absence of drug; (C) T cells were rendered tolerant, rested then rechallenged in presence or absence of $A_{2a}$ antagonist.

The ability of the A2 antagonist ATL-264 to prevent tumor induced tolerance in vivo was tested. As seen in FIG. 8, $A_{2a}$ receptor engagement during either the induction or the effector phase of the T cell response leads to tolerance. $A_{2a}$ receptor engagement with CGS-21680 (CGS), an $A_{2a}$ receptor-specific agonist, markedly inhibits T cell activation (FIG. 8A). In addition, signaling through the $A_{2a}$ receptor during antigen recognition renders the T cells hyporesponsive upon subsequent rechallenge (FIG. 8B). That is $A_{2a}$ receptor engagement during T cell activation can render T cells tolerant such that they are anergic upon rechallenge even in the absence of adenosine or $A_{2a}$ agonists. Importantly, the $A_{2a}$ receptor antagonist, ZM-241385 (ZM), can block the induction of this tolerance, such that upon rechallenge, the T cells that were incubated with both CGS and ZM were actually hyper-responsive (FIG. 8B). Furthermore, $A_{2a}$ receptor antagonism can actually enhance the activity of previously tolerized T cells (FIG. 8C). Thus, $A_{2a}$ receptor engagement inhibits T cell activation and promotes tolerance while $A_{2a}$ receptor antagonism increases T cell activate and prevents the induction of tolerance.

Example 6

Memory T Cell Responses

Figure 9:
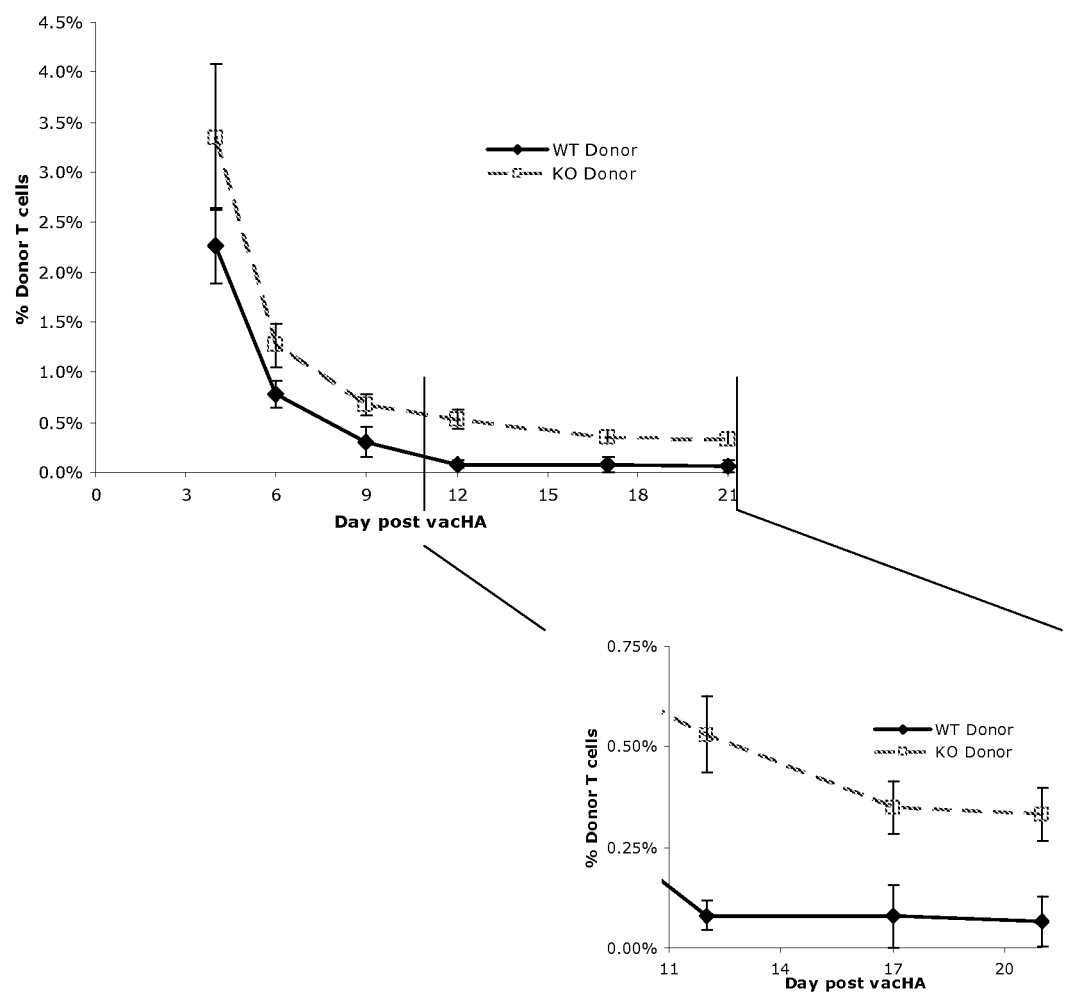
FIG. 9 is a graph displaying the percentage of donor T cells after vaccinia infection in either wild type (WT) or $A_{2a}$ receptor knock-out (KO) mice. Non-transgenic B10.D2 mice were vaccinated with $10^6$ pfu VacHA. $1\times10^6$ CD4-enriched 6.5+ T cells were transferred into the host mice by tail vein injection. Antigen specific memory T cells were determined in the peripheral blood by assaying for Thy 1.1+ (donor) CD4+ T cells.
Figure 10:
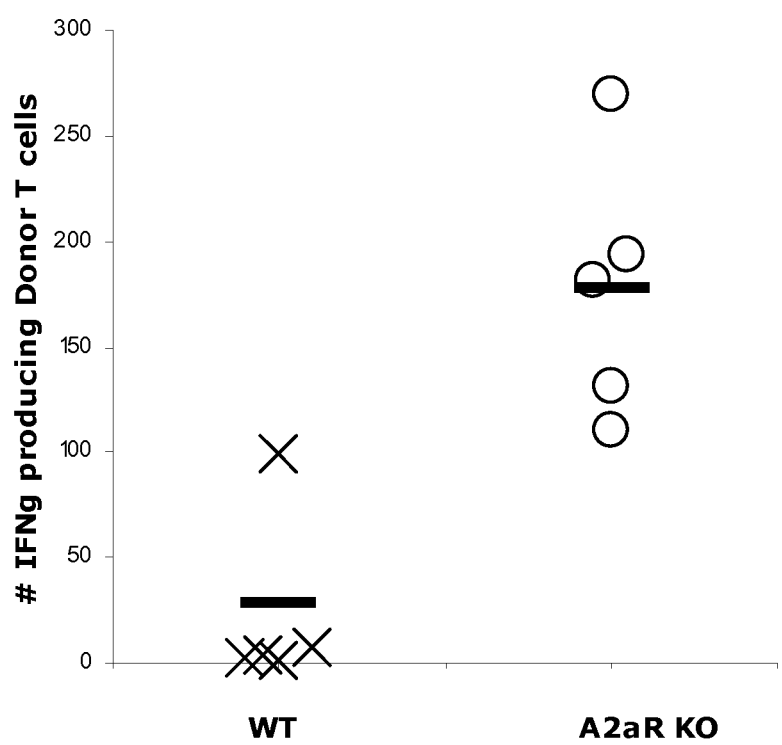
FIG. 10 is a graph of the number of IFN-γ-producing donor T cells in either wild type or $A_{2a}$ receptor null mice derived splenocytes from mice infected with vaccinia infection after rechallenge. Non-transgenic B10.D2 mice were vaccinated and given $1\times10^6$ 6.5+ T cells as in FIG. 9. On Day 20, the mice were sacrificed and splenocytes were assayed for IFN-γ production by in vitro stimulation with HA peptide.
Figure 11:
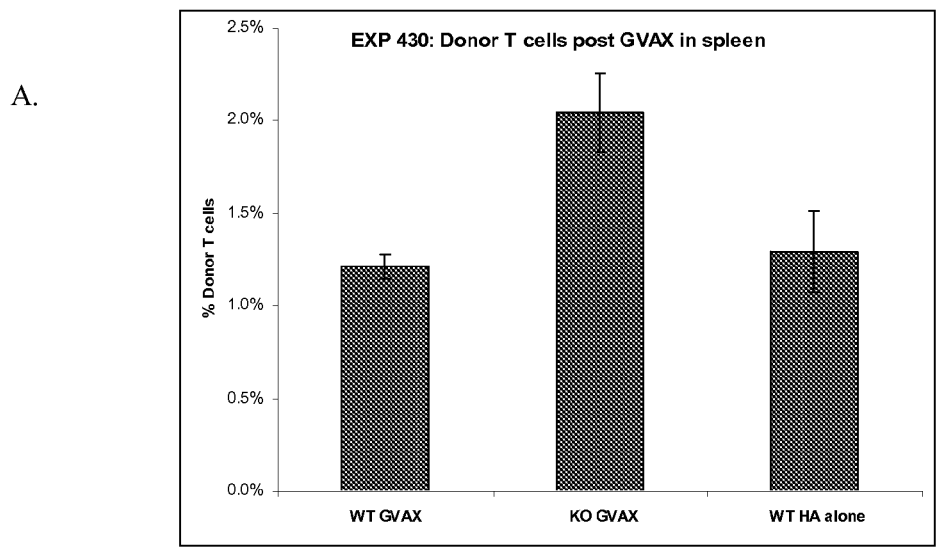
FIGS. 11(a)-(b) shows the percentage of donor cells from either wild type or $A_{2a}$ receptor knock out in mice vaccinated with GVAX. (A) Non-transgenic B10.D2 mice were given a dose of irradiated GM-CSF-secreting cells that produce 300 ng of GM-CSF per $1\times10^6$ cells per 24 hour time period. Typically, this results in about 0.6-1.0×$10^6$ GVAX cells per mouse. The mice also received $1\times10^6$ irradiated HA-expressing A20 lymphoma cells. The following day the mice receive $1\times10^6$ 6.5- T cells. On Day 8, the mice were sacrificed and splenocytes were analyzed for the percentage of donor T cells. (B) displays the percentage of IFN-g producing, tumor-specific donor T cells T cells from wild type or $A_{2a}$ receptor knock out mice after GVAX vaccination (as above) when cells were rechallenged in vitro with HA.
Figure 11:
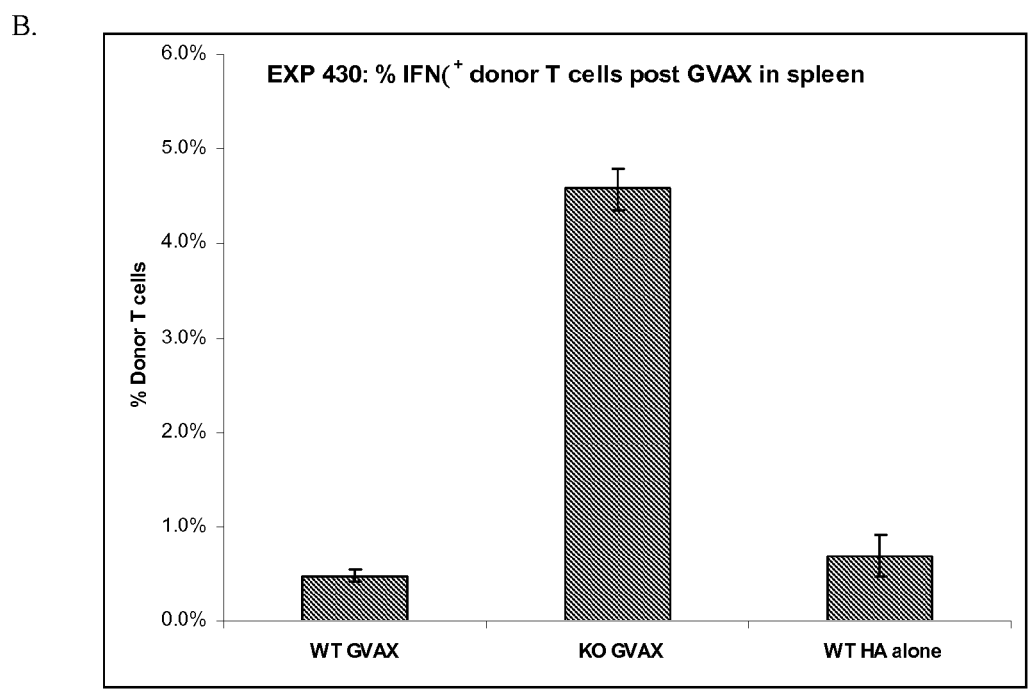
Figure 12:
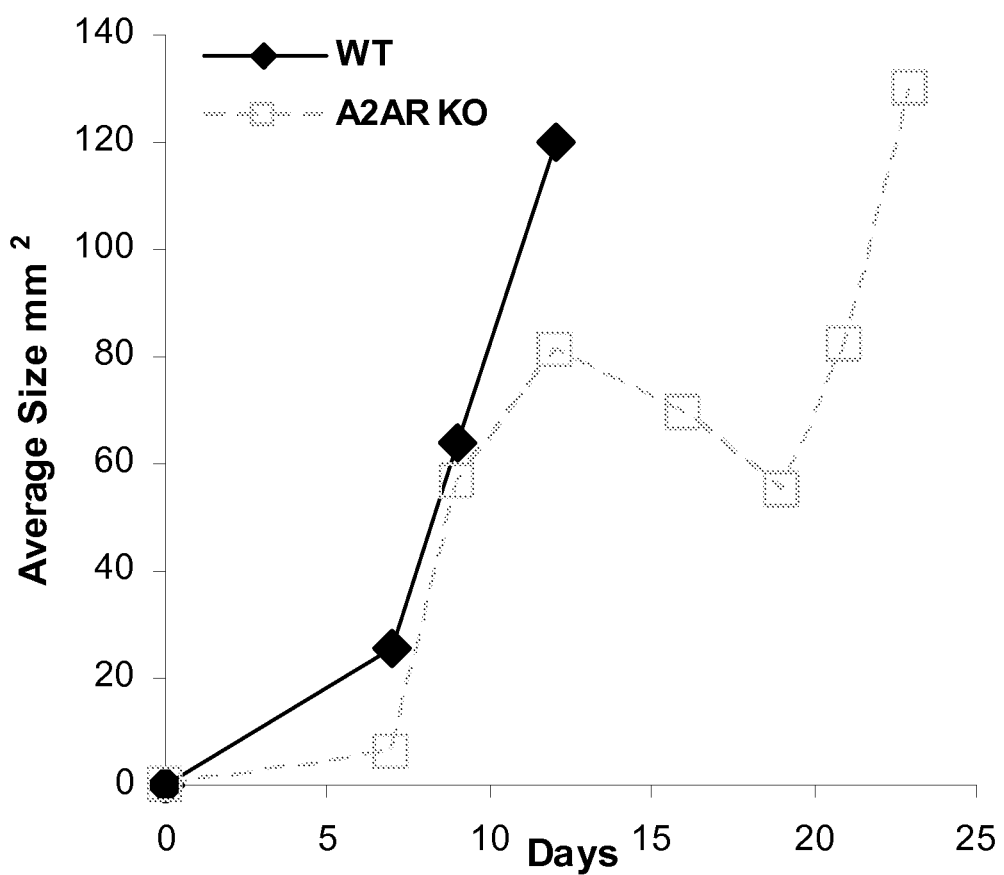
FIG. 12 is a graph of the average size in $mm^2$ of tumor size over time in wild type (WT) and $A_{2a}$ receptor null ($A_{2a}$ receptor KO) mice after treatment with the whole cell GVAX vaccine.

FIG. 9 demonstrates that antigen specific T cells from $A_{2a}$ receptor null mice expand to a greater extent after infection with vaccinia virus. This expansion leads to the generation of more IFN-γ producing effector cells (FIG. 10). Similarly there is an increase in expansion and generation of functional antigen specific effector T cells in $A_{2a}$ receptor null mice when these are vaccinated with a whole cell GVAX vaccine (FIGS. 11a & 11b). $A_{2a}$ receptor null mice also have an increased response to the whole cell GVAX vaccine when measured by average tumor size over time (see FIG. 12).

Figure 13:
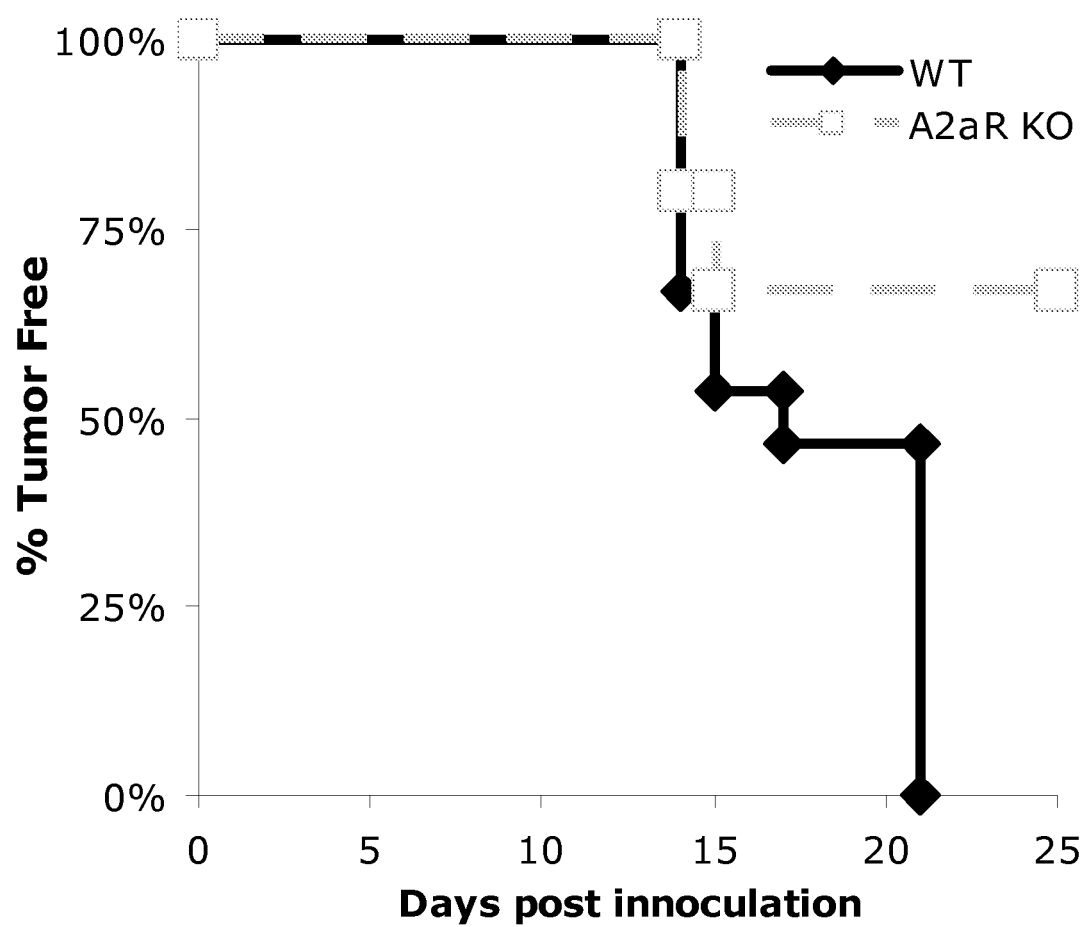
FIG. 13 is a graph of the percent tumor free survival of wild type and $A_{2a}$ receptor knock out mice challenged with $1\times10^5$ EL-4 lymphoma cells over 30 days.
Figure 14:
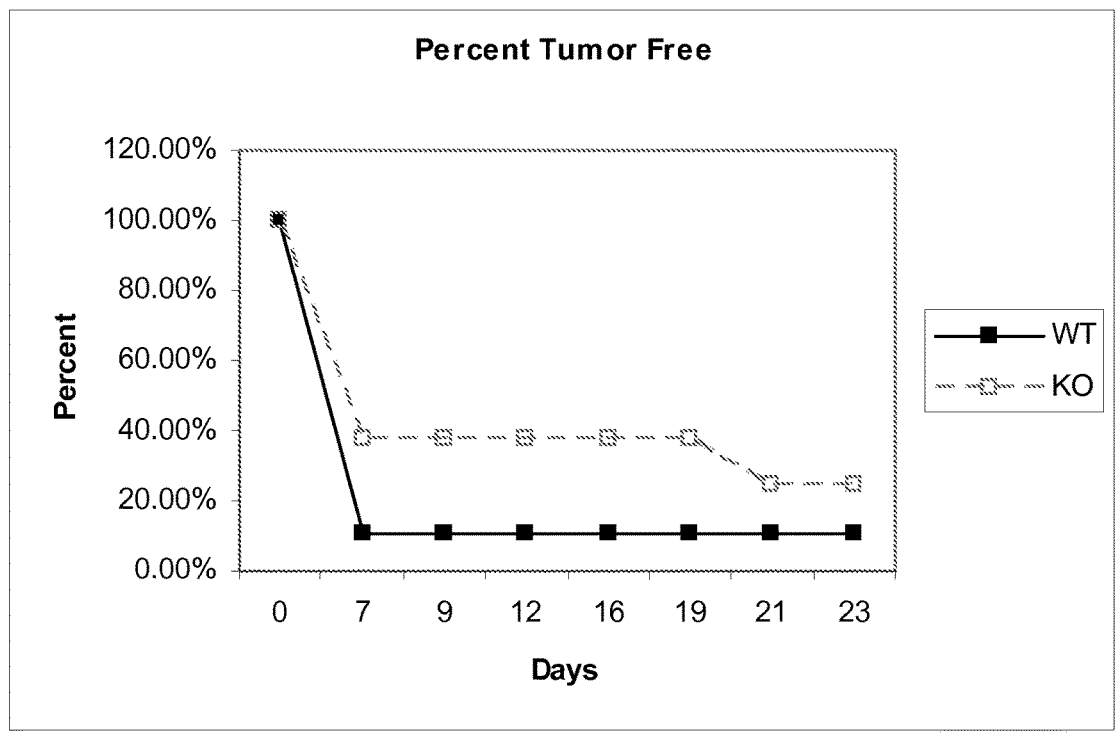
FIG. 14 is a graph of percent disease free survival over time in wild type or $A_{2a}$ receptor knock out mice vaccinated with GVAX and challenged with $1\times10^6$ EL-4 lymphoma cells.
Figure 15:
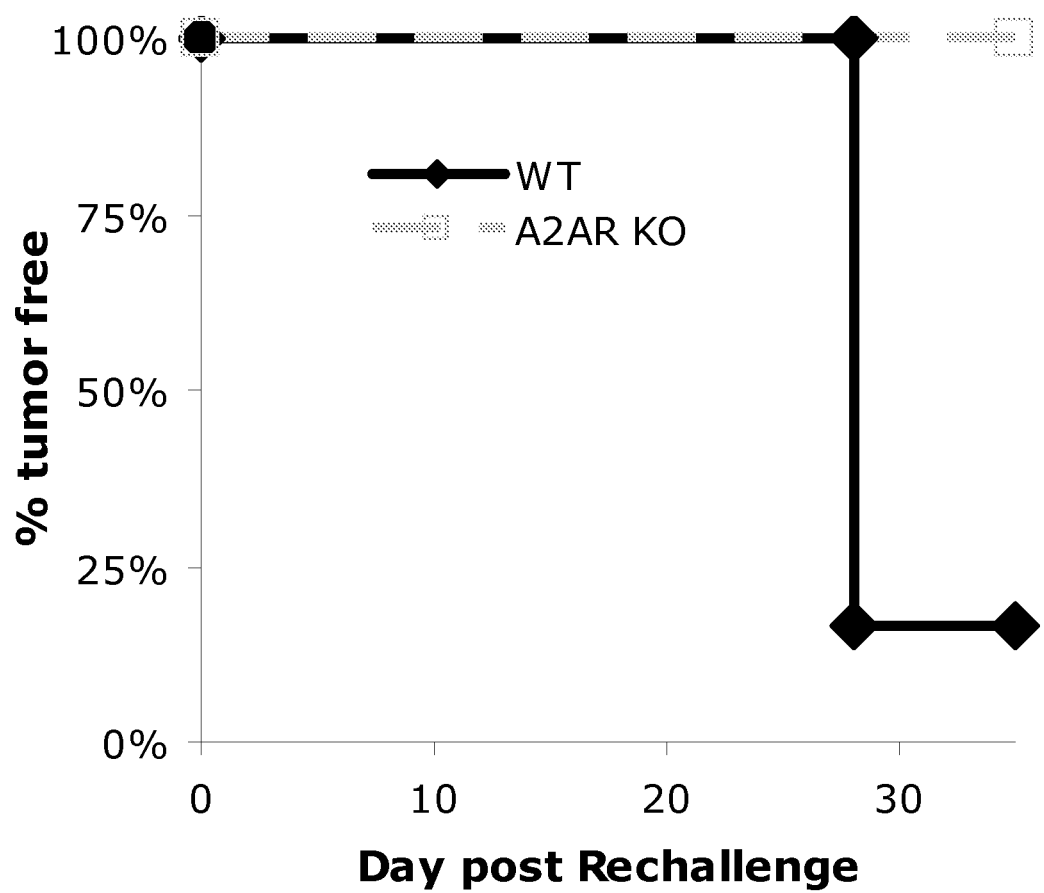
FIG. 15 shows the percent of tumor free survival over time in wild type or $A_{2a}$ receptor knock out mice that had been previously challenged with EL-4 lymphoma cells. Wt or KO mice were initially inoculated subcutaneously with $1\times10^4$ EL-4 cells in the left flank on Day −30. No tumor developed. On Day 0, the mice received $1\times10^6$ EL-4 cells in the right flank. The graph follows the development of palpable tumor following the second tumor ($1\times10^6$) challenge.

During an infection, T cells respond to antigens from the pathogen either presented by the infected cells or cross presented by professional antigen presenting cells. Experiments were designed to test whether an endogenous immune response of $A_{2a}$ receptor null mice would be more robust than that of Wt mice. As seen in FIG. 13, when give $10^5$ lymphoma cells, $A_{2a}$ receptor null mice reject the tumor and remain essentially tumor free while WT mice develop tumor and die. Finally, when the mice are given $10^6$ lymphoma cells, there is a delay in death in the $A_{2a}$ receptor null mice compared with the Wt mice (data not shown). Therefore we gave Wt and $A_{2a}$ receptor null mice GVAX, challenged them with $10^6$ tumor cells and then followed them for disease free survival. As seen in FIG. 14, with 1 vaccination a greater percentage of $A_{2a}$ receptor null mice achieved disease free survival when compared with the Wt mice. FIG. 15 shows the percent of tumor free survival over time in wild type or $A_{2a}$ receptor knock out mice that had been previously challenged with EL-4 lymphoma cells. Wt or KO mice were initially inoculated subcutaneously with $1 \times 10^4$ EL-4 cells in the left flank on Day −30. No tumor developed. On Day 0, the mice received $1 \times 10^6$ EL-4 cells in the right flank. The graph follows the development of palpable tumor following the second tumor ($1 \times 10^6$) challenge.

Example 7

Figure 16:
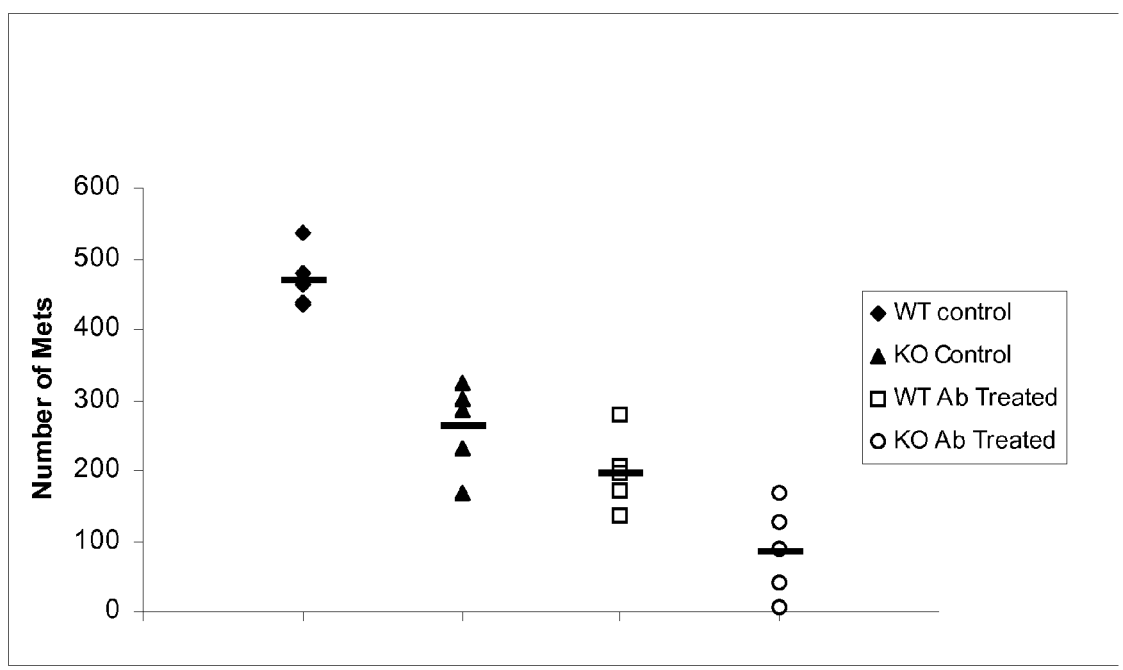
FIG. 16 is a graph demonstrating enhanced activity of the anti-melanoma antibody TA99 in $A_{2a}$ receptor null mice. Wt and $A_{2a}$ receptor null mice received 1 million B16 melanoma cells IV on day 0. Control mice received not treatment. Treated mice received 200 ug IP of TA99 antibody on days 0, 2, 5. The mice were sacrificed on Day 15 and lung mets were counted.

$A_{2a}$ Receptor Antagonists Enhanced Antibody Mediated Anti-Melanoma Therapy Antibody therapy is more effective in $A_{2a}$ receptor KO mice. Wt and $A_{2a}$ receptor null mice received 1 million B16 melanoma cells IV on day 0. Control mice received not treatment. Treated mice received 200 ug IP of TA99 antibody on days 0, 2, 5. The mice were sacrificed on Day 15 and lung metastases were counted. As shown in FIG. 16, $A_{2a}$ receptor knock out animals have melanoma metastases at similar levels to mice treated with antibody. Eliminating $A_{2a}$ receptor activity in the mice reduced melanoma metastases by approximately 50% and treatment with the antibody reduced metastases by approximately 60%. However, when knock out mice are treated with the antibody, the level of tumor metastases dropped by approximately 80% when compared to untreated wild type, and by 50% or more when compared to either the knock out or antibody treated wild type mice.

Figure 17:
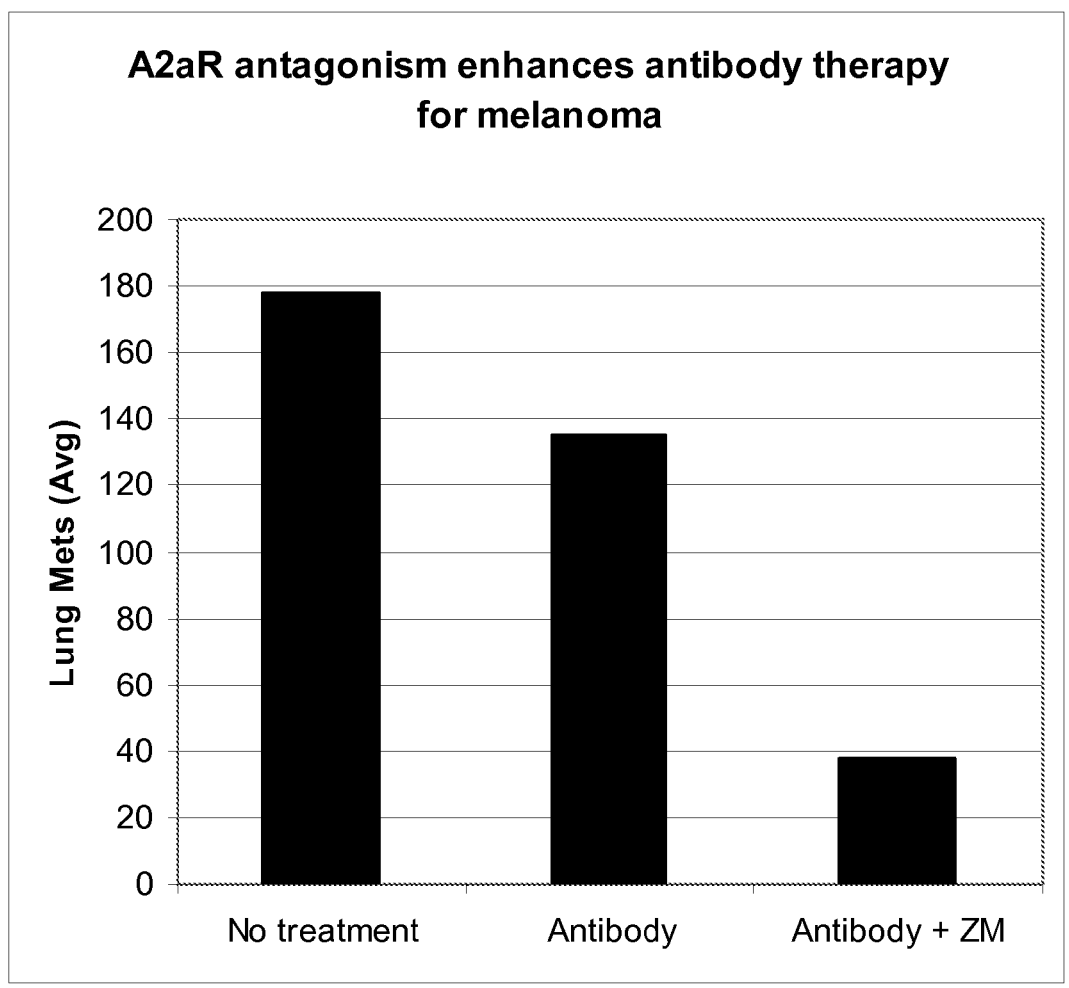
FIG. 17 is a graph demonstrating the ability of the $A_{2a}$ receptor antagonist ZM241385 (ZM) to enhance the activity of the anti-melanoma antibody TA99. Wt mice received 1 million B16 melanoma cells on Day 0. On day +1 they received either no treatment or 200 ug of TA99 antibody. Zm treated mice received 10 mg/kg IP of ZM twice a day beginning on Day 0 and continuing for the remainder of the experiment. The mice were evaluated on Day +15.

Similarly, as seen in FIG. 17, treatment with a pharmacological $A_{2a}$ receptor antagonist (ZM 241385; "ZM") showed enhanced reduction in melanoma metastases in the B16 tumor model tumor model. Wt mice received 1 million B16 melanoma cells on Day 0. On day +1 they received either no treatment or 200 ug of TA99 antibody. Zm treated mice received 10 mg/kg IP of ZM twice a day beginning on Day 0 and continuing for the remainder of the experiment. The mice were evaluated on Day +15. The average lung metastases in animals treated only with antibody treatment reduced by approximately 25%, however when in combination with ZM, the average lung metastases reduced by approximately 80%.

The invention claimed is:

1. A method of treating or preventing abnormal cell proliferation in a host, comprising administering to said host an $A_{2a}$ receptor antagonist in combination or alternation with a mammalian cell based vaccine, wherein the mammalian cell is genetically modified.

2. The method of claim 1, wherein the mammalian cell based vaccine constitutively secretes a colony stimulating factor.

3. The method of claim 1, wherein the $A_{2a}$ receptor antagonist is administered before administration of the mammalian cell based vaccine.

4. The method of claim 1, wherein the $A_{2a}$ receptor antagonist is administered in conjunction with the administration of the mammalian cell based vaccine.

5. The method of claim 1, wherein the $A_{2a}$ receptor antagonist is administered in combination with the mammalian cell based vaccine and further comprising administering an anti-cancer agent to the host.

* * * * *

SEQUENCE LISTING

<160> NUMBER OF SEQ ID NOS: 6

<210> SEQ ID NO 1
<211> LENGTH: 21
<212> TYPE: DNA

```
<213> ORGANISM: Artificial Sequence
<220> FEATURE:
<223> OTHER INFORMATION: LAG-3 primer

<400> SEQUENCE: 1
acatcaacca gacagtggcc a                                              21

<210> SEQ ID NO 2
<211> LENGTH: 19
<212> TYPE: DNA
<213> ORGANISM: Artificial Sequence
<220> FEATURE:
<223> OTHER INFORMATION: LAG-3 primer

<400> SEQUENCE: 2
gcatcccctg gtgaaggtc                                                 19

<210> SEQ ID NO 3
<211> LENGTH: 19
<212> TYPE: DNA
<213> ORGANISM: Artificial Sequence
<220> FEATURE:
<223> OTHER INFORMATION: LAG-3 probe

<400> SEQUENCE: 3
cccactccca tcccggccc                                                 19

<210> SEQ ID NO 4
<211> LENGTH: 19
<212> TYPE: DNA
<213> ORGANISM: Artificial Sequence
<220> FEATURE:
<223> OTHER INFORMATION: FoxP3 primer

<400> SEQUENCE: 4
ggcccttctc caggacaga                                                 19

<210> SEQ ID NO 5
<211> LENGTH: 20
<212> TYPE: DNA
<213> ORGANISM: Artificial Sequence
<220> FEATURE:
<223> OTHER INFORMATION: FoxP3 primer

<400> SEQUENCE: 5
gctgatcatg gctgggttgt                                                20

<210> SEQ ID NO 6
<211> LENGTH: 32
<212> TYPE: DNA
<213> ORGANISM: Artificial Sequence
<220> FEATURE:
<223> OTHER INFORMATION: FoxP3 probe

<400> SEQUENCE: 6
acttcatgca tcagctctcc actgtggatt at                                  32
```